US010689400B2

(12) United States Patent
Cui et al.

(10) Patent No.: US 10,689,400 B2
(45) Date of Patent: Jun. 23, 2020

(54) MACROCYCLE KINASE INHIBITORS

(71) Applicant: Turning Point Therapeutics, Inc., San Diego, CA (US)

(72) Inventors: Jingrong Jean Cui, San Diego, CA (US); Yishan Li, San Diego, CA (US); Evan W. Rogers, San Diego, CA (US); Dayong Zhai, San Diego, CA (US); Jane Ung, San Diego, CA (US)

(73) Assignee: Turning Point Therapeutics, Inc., San Diego, CA (US)

( * ) Notice: Subject to any disclaimer, the term of this patent is extended or adjusted under 35 U.S.C. 154(b) by 0 days.

(21) Appl. No.: 16/320,589

(22) PCT Filed: Jul. 27, 2017

(86) PCT No.: PCT/US2017/044214
§ 371 (c)(1),
(2) Date: Jan. 25, 2019

(87) PCT Pub. No.: WO2018/022911
PCT Pub. Date: Feb. 1, 2018

(65) Prior Publication Data
US 2019/0169208 A1  Jun. 6, 2019

Related U.S. Application Data

(60) Provisional application No. 62/367,886, filed on Jul. 28, 2016.

(51) Int. Cl.
*C07D 498/18* (2006.01)
*A61K 45/06* (2006.01)

(52) U.S. Cl.
CPC ............ *C07D 498/18* (2013.01); *A61K 45/06* (2013.01)

(58) Field of Classification Search
CPC .............................. C07D 498/18; A61K 45/06
See application file for complete search history.

(56) References Cited

U.S. PATENT DOCUMENTS

| | | | |
|---|---|---|---|
| 5,639,778 A | 6/1997 | Andersson | |
| 8,680,111 B2 | 3/2014 | Bailey | |
| 8,815,872 B2 | 8/2014 | Yu | |
| 8,933,084 B2 * | 1/2015 | Andrews | A61K 31/519 514/258.1 |
| 9,714,258 B2 | 7/2017 | Cui | |
| 10,246,466 B2 | 4/2019 | Cui | |
| 10,294,242 B2 | 5/2019 | Cui | |
| 10,316,044 B2 | 6/2019 | Cui | |
| 2011/0294801 A1 | 12/2011 | Yu | |
| 2013/0203776 A1 | 8/2013 | Andrews | |
| 2013/0245021 A1 | 9/2013 | Bi | |
| 2013/0252961 A1 | 9/2013 | Bailey | |
| 2014/0107099 A1 | 4/2014 | Blaney | |
| 2014/0206605 A1 | 7/2014 | Beutner | |
| 2016/0339027 A1 | 11/2016 | Carter | |
| 2017/0002023 A1 | 1/2017 | Cui | |
| 2017/0334929 A1 | 11/2017 | Cui | |
| 2018/0186813 A1 | 7/2018 | Cui | |
| 2018/0194777 A1 | 7/2018 | Cui | |
| 2018/0325901 A1 | 11/2018 | Cui | |

FOREIGN PATENT DOCUMENTS

| | | |
|---|---|---|
| CL | 2012003227 | 2/2013 |
| CN | 102143750 | 8/2011 |
| CN | 102971322 | 3/2013 |
| JP | 2012502043 | 1/2012 |
| WO | 2010028116 | 3/2010 |
| WO | 2010033941 | 3/2010 |
| WO | 2010048314 | 4/2010 |
| WO | 2010051549 | 5/2010 |
| WO | 2011146336 | 11/2011 |
| WO | 2012034091 | 3/2012 |
| WO | 2012136859 | 10/2012 |
| WO | 2013001310 | 1/2013 |
| WO | 2013028465 | 2/2013 |
| WO | 2013045653 | 4/2013 |
| WO | 2013132376 | 9/2013 |
| WO | 2013134219 | 9/2013 |
| WO | 2013134228 | 9/2013 |
| WO | 2013147711 | 10/2013 |
| WO | 2015112806 | 7/2015 |
| WO | WO2015/112806 | 7/2015 |
| WO | 2017004342 | 1/2017 |
| WO | 2017007759 | 1/2017 |
| WO | 2017015367 | 1/2017 |
| WO | 2018022911 | 2/2018 |
| WO | 2018140554 | 8/2018 |
| WO | 2019023417 | 1/2019 |

OTHER PUBLICATIONS

Xie, Q., et al. Hepatocyte growth factor (HGF) autocrine activation predicts sensitivity to MET inhibition in alioblastoma. Proc. Natl. Acad. Sci. U.S. A. 2012, 109, 570-575.
International Search Report and Written Opinion prepared for PCT/US2016/043132, dated Sep. 28, 2016, 8 pages.
International Search Report and Written Opinion prepared for PCT /US2016/040329, dated Sep. 7, 2016, 13 pages.
International Search Report and Written Opinion prepared for PCT /US2016/040972, dated Sep. 13, 2016, 8 pages.
Liu L, et al. Nature, 2012, 483, 608-612.
PubChem-CID98009788,Create Date: Dec. 11, 2015 (Dec. 11, 2015).
Buchert M, et al. Oncogene, 2016, 25, 939-951; published May 18, 2015.
Johnson et al., "Discovery of (10R)-7-Amino-12-fluoro-2,10,16-trimethyl-15-oxo-10,15,16,17-tetrahydro-2H-8,4-(methano)pyrazolo[4,3-h][2,5,11]-benzoxadiazacyclotetradecine-3-carbonitrile (PF-06463922), a Macrocyclic Inhibitor of Anaplastic Lymphoma Kinase (ALK) and c-ros Oncogene 1 (ROS1) with Preclinical Brain Exposure and Broad-Spectrum Potency against ALK-Resistant Mutations", J. Med. Chem., Jun. 12, 2014, 57, 4720-4744.

(Continued)

*Primary Examiner* — Erich A Leeser
(74) *Attorney, Agent, or Firm* — Barnes & Thornburg LLP

(57) ABSTRACT

The present disclosure relates to certain macrocyclic kinase inhibitors, pharmaceutical compositions containing the same, and methods of using the same to treat disease.

19 Claims, No Drawings

(56) References Cited

OTHER PUBLICATIONS

Zou et al., "PF-06463922 is a potent and selective next-generation ROS1/ALK inhibitor capable of blocking crizotinib-resistant ROS1 mutations", PNAS, Mar. 17, 2015, vol. 112, No. 11, 3493-3498.
Peterson et al., "Expanding the Scope of Crystal Form Evaluation in Parmaceutical Science" Journal of Pharmacy & Pharmaceutical Science 2006 9(3):317-326.
Miller et al., "Solvent Systems for Crystallization and Polymorph Selection" Chapter 3 in Solvent Systems and Their Selection in Pharmaceutics and Biopharmaceutics Series Biotechnology: Pharmaceutical Aspects vol. VI Augustijns, Patrick; Brewster, Marcus (Eds.) 2007.
International Search Report and Written Opinion prepared for PCT/US2015/012597, dated Aug. 28, 2015, 11 pages.
European Search Report issued in EP 16828471, completed Mar. 15, 2019.
European Search Report issued in EP 16818768, completed Jan. 22, 2019.
Wiesner T, et al Nature 2015, 526, 453-457.
Voena C, et al. Oncotarget, Apr. 23, 2016, 8955.
Uquen A, et al Future Oncol. Jun. 3, 2016, Epub ahead of print.
Gao SP, et al. Sci Signal. 206, 9 (421):ra33: published online Mar. 29, 2016.
Balko JM, et al. Sci Transl Med. 2016, 8 (334):ra53, published Apr. 13, 2016.
Liu W, et al. Oncotarget. 2015, 6: 35522-35541.
Serrels A, et al, Cells 2015, 163, 160-173.
Shi L, et al. Br J Cancer. 2014, 111(12): 2316-27.
Xu T, et al. Cancer Lett. 2016, 377(2): 140-8, published online Apr. 25, 2016.
Elias D., et al Pharmacological Research 2015, 100, 250-254.
Ambrogia C, et al, Nature Medicine, 2016, 22, 270-277, published Feb. 8, 2016.
Bender AT, et al. Clinical Immunology 2016, 164, 65-77, available online Jan. 25, 2016.
Morgillo F, Della Corte CM, Fasano M. et al. Mechanisms of resistance to EGFR-targeted drugs: lunch cancer. ESMO Open 2016;1: e000060, published online May 11, 2016.
Pubchem, Compound Summary for SID 252159180, available date; Aug. 10, 2015, retrieved Aug. 31, 2017, retrieved from: https://pubchem.ncbi.nlm.nih.gov/substance/252159180.
Rahal, "The development of Potent and Selective RET inhibitors", Presentation at Annual AACR Meeting, Apr. 18, 2016.
Toso, A. et al., Cell Reports 2014, 9, 75-89.
Shaw, A. T. et al., N Engl J Med. 2014, 371(21):1963-1971.
Politi K, Clin Cancer Res. 2014, 20, 5576.
Crystal AS, Science. 2014, 346, 1480.
Vaishnavi A, et al Cancer Discov. 2015, 5, 25.
Park, K-S, et al. J Clin Invest. 2014, 124(7):3003-3015.
Golubovskaya VM, Front Biosci (Landmark Ed). ; 19: 687-706.
Stransky N, et al. Nature Communications 2014, 5, 4846.
Schwarz LJ, et al. J Clin Invest. 2014, 124, 5490-5502.
Zardan A., et al. Oncogenesis 2014, 3, e 115.
Rudd ML, et al. BMC Cancer 2014, 14, 884.
Furman RR, et al. New England Journal of Medicine, 2014, 370, 2352-2354.
Chiron D, et al. Cancer Discovery, 2014, 4, 1022-1035.
Woyach JA, el al. New England Journal of Medicine, 2014, 370, 2286-2294.
Gunderson AJ, et al. Cancer Discov. 2016, 6, 270-285, published online Dec. 29, 2015.
Mulligan, LM. Nat Rev Cancer. 2014, 14(3):173-86.
Fujita-Sato, S., et al. Enhanced MET Translation and Signaling Sustains K-Ras-Driven Proliferation under Anchorage-Independent Growth Conditions. Cancer Res. 2015, 75, 2851-2862.
Song N, et al. Cetuximab-induced MET activation acts as a novel resistance mechanism in colon cancer cells. Int J Mol Sci. 2014, 15, 5838-5851.

Ries CH, et al. Targeting tumor-associated macrophages with anti-CSFIR antibody reveals a strategy for cancer therapy. Cancer Cell. 2014, 25, 846-859.
Jiang H, et al. Nat Med. Jul. 4, 2016, [Epub ahead of print].
Hackam et al., "Translation of Research evidence From Animals to Humans", JAMA, 2006; 296(14): 1731-1732.
European Search Report issued in EP 1156696, completed Jan. 30, 2019.
Lim et al., "Discovery of 5-Amino-N-(1H-pyrazol-4-yl)pyrazolo[1,5-a]pyrimidine-3-carboxamide Inhibitors of IRAK4," ACS Medicinal Chemistry Letters (2015), 6(6), 683-688.
PCT Search Report and Written Opinion prepared for PCT/US2017/044214, completed Nov. 10, 2017.
Publication info: XP055459702, "Substance Record for SID 252159180," Aug. 10, 2015, PubChem, pp. 1-5.
Gargalionis et al., "The molecular rationale of Src inhibition in colorectal carcinomas", Int. J. Cancer: 134, 2019-2029 (2014). Published online Jun. 21, 2013.
Okamoto et al., "Identification of c-Src as a Potential Activation as a Cause of Resistance to c-Src Published online Apr. 20, 2010 Inhibition", Therapeutic Target for Gastric Cancer and of MET Mol Cancer Ther., May 2010; 9(5): 1188-97.
Vergani et al., "Identification of MET and SRC Activation in Melanoma Cell Lines Showing Primary Resistance to PLX4032", Neoplasia. Dec. 2011; 13(12): 1132-42.
Pachter et al., "The Chemistry of Hortiamine and 6-Methoxyrhetsinine," J. Am. Chem. Soc., 1961, 83, 635-642.
Kiselyov, Alexander S., "Solid support synthesis of 15-membered macrocycles containing a serotonin unit," Tetrahedron Letters 46 (2005) 3007-3010.
Halland et al. "Small Macrocycles As Highly Active Integrin 0131 Antagonists," ACS Medicinal Chemistry Letters, Jan. 10, 5, 2014, 193-198.
Couronne L, et al. Blood 2013, 122, 811.
Takahashi, M. et al. Cell. 1985, 42:581-588.
Schiller J H et al., N Engl J Med, 346: 92-98, 2002.
Pachnis, V., et al. Development 1993, 119, 1005-1017.
Schuchardt, A. et al. Nature 1994, 367:380-383.
Grieco, M. et al. Cell. 1990, 23; 60 (4):557-63.
Gainor JF, Shaw AT. Oncologist. 2013, 18(7):865-75.
Kentsis, A., et al. Autocrine activation of the MET receptor tyrosine kinase in acute myeloid leukemia. Nat. Medd. 2012, 18, 1118-1122.
Yano, S., et al. Hepatocyte growth factor induces gefitinib resistance of lung adenocarcinoma with epidermal growth factor receptor-activating mutations. Cancer Res. 2008, 68, 9479-9487.
Bardelli, A., et al. Amplification of the Mli'T Receptor Drives Resistance to Anti-EGFR Therapies in Colorectal Cancer. Cancer Discov. 2013, 3, 658-673.
Straussman, R., et al. Tumour micro-environment elicits innate resistance to RAF inhibitors through HGF secretion. Nature 2012, 487, 500-504.
Harbinski, F., et al. Rescue screens with secreted proteins reveal compensatory potential of receptor tyrosine kinases in driving cancer growth. Cancer Discov. 2012, 2, 948-959.
Parsons, S. J., et al. SRC family kinases, key regulators of signal transduction. Oncogene, 2004, 23, 7906-7909.
Wojcik, E. J., et al. A novel activating function of SRC and STAT3 on HGF transcription in mammary carcinoma cells. Oncogene. 2006, 25, 2773-84.
Dulak AM et al. HGF-independent potentiation of EGFR action by Mli'l'. Oncogene. 2011, 30, 3625-3635.
Stabile, L. P., et al. c-SRC activation mediates erlotinib resistance in head and neck cancer by stimulating MET. Clin Cancer Res. 2012, 19, 1-13.
Bertotti, A., et al. Inhibition of SRC impairs the growth of MET-addicted gastric tumors. Clin Cancer Res. 2010, 16,3933-3943.
Wrobel CN, et al. Autocrine CSFIR activation promotes SRC-dependent disruption of mammary epithelial architecture. J Cell Biol. 2004, 165, 263-273.
Ravi V, et al. Treatment of tenosynovial giant cell tumor and pigmented villonodular synovitis. Curr Opin Oncol. 2011, 23, 361-366.
Gridelli, C. et al., Cancer Treat Rev. 2014, 40, 300-306.
Liu Z, et al. J. Clin. Endocrinol. Metab. 2004, 89, 3503-3509.

(56) References Cited

OTHER PUBLICATIONS

Cooper, C. S., et al Molecular cloning of a new transforming gene from a chemically transformed human cell line. Nature 1984, 311, 29-33.
Boccaccio, C.; Comoglio, P. M. Invasive growth: a MET-driven generic programme for cancer and stem cells. Nat. Rev. Cancer 2006, 6, 637-645.
Ma, PC et al. Expression and mutational analysis of MET in human solid cancers. Genes Chromosomes Cancer 2008, 47, 1025-1037.
Maulik, G., et al. Role of the hepatocyte growth factor receptor, MET, in oncogenesis and potential for therapeutic inhibition. Cytokine Growth Factor Rev. 2002, 13, 41-59.
Smolen, G. A., et al. Amplification of MET may identify a subset of cancers with extreme sensitivity to the selective tyrosine kinase inhibitor PHA-665752. Proc. Natl. Acad. Sci. U.S. A. 2006, 103, 2316-2321.
Ghiso, E.; Giordano, S. Targeting MET: why, where and how? Curr. Opin. Pharmacol. 2013, 13, 511-518.
Otsuka, T., et al. MET autocrine activation induces development of malignant melanoma and acquisition of the metastatic phenotype. Cancer Res. 1998, 58, 5157-5167.
Sawyers, C., Nature 2004, 432, 294-297.
Bottaro, D. P. etal., Science 1991, 251, 802-804.
Gherardi, E. et al., Nature Rev. Cancer 2012, 12, 89-103.
Engelman, J. A. et al., Science 2007, 316, 1039-1043.
Wilson, T.R. et al., Nature 2012, 487, 505-509.
Pulford, K. et al., Cell Mol. Life Sci. 2004, 61, 2939.
Manning, G. et al., Science 2002, 298, 1912-1934.
Morris, S.W. et al., Science 1994, 263, 1281.
Bischof, D. et al., Mol. Cell Biol., 1997, 17, 2312-2325.
Soda, M. et al., Nature 2007, 448, 561-566.
Mosse, Y. P. et al., Nature 2008, 455, 930-935.
Thiele, C. J. et al., Clin. Cancer Res. 2009, 15, 5962-5967.
Pierotti, M.A. et al., Cancer Lett. 2006, 232, 90-98.
Vaishnavi, A. et al., Nat. Med. 2013, 19, 1469-1472.
Verma, A. etal., Mol. CancerTher. 2011, JO, 1763-1773.
Zhang, Z. et al., Nat. Genet. 2012, 44, 852-860.
Cui, J. J. et al., J. Med. Chem. 2011, 54, 6342-6363.
Katayama, R. et al., Sci. Transl. Med. 2012, 4, 120ra17.
Quintas-Cardama, A. et al., Nat. Rev. Drug Discov. 2011, 10(2), 127-40.
Pesu, M. et al., Immunol. Rev. 2008, 223, 132-142.
Murray, P.J., J. Immunol. 2007, 178(5), 2623-2329.
Muller, M. et al., Nature 1993, 366(6451), 129-135.
Neubauer, H. et al., Cell 1998 93(3), 397-409.
Nosaka, T. et al., Science 1995, 270(5237), 800-802.
Vainchenker, W. et al., Semin. Cell. Dev. Biol. 2008, 19(4), 385-393.
Levine, R.L. etal., Cancer Cell 2005, 7(4), 387-397.
Kralovics, R. et al., N. Engl. J. Med. 2005, 253(17), 1779-1790.
James, C. et al., Nature 2005, 434(7037), 1144-1148.
Baxter, E.J. et al. Lancet 2005, 365(9464), 1054-1061.
LaFave, L.M. et al., Trends Pharmacol. Sci. 2012, 33(11), 574-582.
Verstovsek, S. et al., N. Engl. J. Med. 2012, 366(9), 799-807.
Quintas-Cardama, A. et al., Blood 2010, 115(15), 3109-3117.
Nefedova, Y. et al., Cancer Res 2005; 65(20): 9525-35.
Davies, K. D. et al., Clin Cancer Res 2013, 19 (15): 4040-4045.
Awad, M. M. et al., N Engl J Med. 2013, 368(25):2396-2401.
Charest A, et al Genes Chromosomes Cancer 2003, 37, 58.
Takeuchi K, et al Nat. Med. 2012, 18, 378.
Gu TL, et al PLoS One. 2011, 6, e15640.
Lacronique V, et al. Science 1997, 278, 5341, 1309-12.
Zhang S, et al Trends Pharmacol Sci. 2012, 33, 122.
Bromann PA, Oncogene 2004, 23, 7957-7968.
Summy JM, et al. Cancer Metastasis Rev. 2003, 22, 337-358.
Scancier F. et al. PLoS One. 2011, 6(2): el 7237.
Ongusaha PP, et al. EMBO J. 2003, 22, 1289-1301.
Hammerman PS, et al. Cancer Discov. 2011, 1, 78-89.
Tomasson MH, et al. Blood 2008, 111:4797-4808.
Yu J. et al., Cancer Cell, 2010, 17, 5, 443-54.
Advani, A.S. et al. Leukemia Research, 2002, 26, 8, 713-720.
Gottesman, M.M., Annu. Rev. Med., 2002, 53, 615-627.
Anastassiadis T, et al Nat Biotechnol. 2011, 29, 1039.
Vetrie D. et al. Nature 1993, 361, 226-233.
Mohamed AJ et al, immunological Reviews, 2009, 228, 58-73.
Grande, E. et al., Mol. Cancer Ther. 2011, 10, 569-579.
Monti, E. 2007. Molecular Determinants of Intrinsic Multidrug Resistance in Cancer Cells and Tumors in B. Teicher (Ed.), Cancer Drug Resistance (pp. 241-260).
McCarthy et al. "Tropomyosin receptor kinase inhibitors: a patent update 2009-2013," Expert Opinions 2014, pp. 731-744.
Di Paolo JA, et al. Nature Chemical Bioloav 2011, 7, 41-50.
Park, M. et al., Cell 1986, 45, 895-904.
Trusolino, L. et al., Nature Rev. Mol. Cell Biol. 2010, 11, 834-848.
Sonbol, M.B. et al., Ther. Adv. Hematol. 2013, 4(1), 15-35.
Reiter A, et al. Cancer Res. 2005, 65, 7, 2662-7.
Sen, B., et al. Distinct interactions between SRC and MET in mediating resistance to SRC inhibition in head and neck cancer. Clin Cancer Res. 2010, 17, 1-11.
Yu, Helena A., et al. Analysis of tumor specimens at the time of acquired resistance to EGFR-TKI therapy in 155 patients with EGFR-mutant lung cancers. Clin. Cancer Res. 2013, 19, 2240-2247.
Baldanzi et al., "Physiological Signaling and Structure of the HGF Receptor MET", Biomedicines 2015, 3, 1-31. First published Dec. 31, 2014.
Heynen et al., "Resistance to targeted cancer drugs through hepatocyte growth factor signaling", Cell Cycle, 2014, 13:24, 3808-3817. Accepted Nov. 11, 2014.
Pennacchietti et al., "Microenvironment-Derived HGF Overcomes Genetically Determined Sensitivity Anti-MET Drugs", Cancer Res. Nov. 15, 2014; 74(22): 6598-609. Published online Sep. 12, 2014.
Lim et al.,"Discovery of 5-Amino-N-(IH-pyrazol-4-yl)pyrazolo[I,5-a]pyrimidine-3-carboxamide Inhibitors of IRAK4," ACS Medicinal Chemistry Letters (2015), 6(6), 683-688.

* cited by examiner

MACROCYCLE KINASE INHIBITORS

CROSS-REFERENCE TO RELATED APPLICATIONS

This application is a national stage entry under 35 USC § 371 of PCT International Application Number PCT/US2017/044214, filed Jul. 27, 2017, which claims priority under 35 U.S.C. § 119(e) to U.S. Provisional Application Ser. No, 62/367,886 filed on Jul. 28, 2016, the entire disclosures of which are incorporated herein by reference.

TECHNICAL FIELD

The present disclosure relates to certain macrocyclic kinase inhibitors, pharmaceutical compositions containing the same, and methods of using the same to treat disease.

BACKGROUND

Protein kinases are key regulators for cell growth, proliferation and survival. Genetic and epigenetic alterations accumulate in cancer cells leading to abnormal activation of signal transduction pathways which drive malignant processes. (Manning, G.; Whyte, D. B.; Martinez, R.; Hunter, T.; Sudarsanam, S. The protein kinase complement of the human genome. *Science* 2002, 298, 1912-1934). Pharmacological inhibition of these signaling pathways presents promising intervention opportunities for targeted cancer therapies. (Sawyers, C. Targeted cancer therapy. *Nature* 2004, 432, 294-297).

The tropomyosin-related receptor tyrosine kinases (Trks) are high-affinity receptors for neurotrophins (NTs), a nerve growth factor (NGF) family. Trk was originally cloned as an oncogene fused with the tropomyosin gene in the extracellular domain. The activating mutations caused by chromosomal rearrangements or mutations in TRK family have been reported in many cancers. (Vaishnavi A, et al *Cancer Discov.* 2015, 5, 25) Because Trks play important roles in pain sensation as well as tumor cell growth and survival signaling, inhibitors of Trk receptor kinases might provide benefit for pain and cancer treatment.

The Janus family of kinases (JAKs) include JAK1, JAK2, JAK3 and TYK2, and are cytoplastic non-receptor tyrosine kinases required for the physiologic signaling of cytokines and growth factors. (Quintas-Cardama A, et al., *Nat. Rev. Drug Discov.* 2011, 10(2), 127) Aberrant regulation of JAK/STAT pathways has been implicated in multiple human pathological diseases, including cancer (JAK2) and rheumatoid arthritis (JAK1, JAK3). A gain-of-function mutation of JAK2 (JAK2V617F) has been discovered with high frequency in patients having myeloproliferative neoplasms (MPN). (Levine R L, et al. *Cancer Cell* 2005, 7, 387) The mutation in the JH2 pseudokinase domain of JAK2 leads to constitutively kinase activity. Cells containing the JAK2V617F mutation acquire cytokine-independent growth ability and often become tumor, providing strong rationale for the development of JAK inhibitors as a targeted therapy. In addition, hyperactivation of the JAK2/signal transducers and activators of transcription 3 (JAK2/STAT3) is responsible for abnormal dendritic cell differentiation leading to abnormal dendritic cell differentiation and accumulation of immunosuppressive myeloid cells in cancer (Nefedova Y, et al. *Cancer Res* 2005, 65, 9525). In Pten-null senescent tumors, activation of the JAK2/STAT3 pathway establishes an immunosuppressive tumor microenvironment that contributes to tumor growth and chemoresistance (Toso A, et al. *Cell Reports* 2014, 9, 75). JAK2 gene fusions with the TEL(ETV6) (TEL-JAK2) and PCM1 genes have been found in leukemia patients. (Lacronique V, et al. *Science* 1997, 278, 5341, 1309-12. Reiter A, et al. *Cancer Res.* 2005, 65, 7, 2662-7.) It was reported that JAK/STAT3 signaling pathway was aberrantly increased in EGFR inhibitor-resistant EGFR-mutant non-small cell lung cancer (NSCLC) cells, and JAK2 inhibition overcomes acquired resistance to EGFR inhibitors that support the use of combination therapy with JAK and EGFR inhibitors for the treatment of EGFR-dependent NSCLC. (Gao S P, et al. *Sci Signal.* 2016, 9 (421):ra33) JAKiSTAT3 signaling promotes cancer hallmarks in the tumor and its environment, including proliferation, survival, angiogenesis, tumor metabolism while suppressing antitumor immunity. (Buchert M. et al. *Oncogene,* 2016, 35, 939-951) Inhibition of cytokine-dependent activation of the JAK/STAT3 pathway with JAK inhibitors may also afford orthogonal treatment opportunities for other oncogene-addicted cancer cells that have gained drug resistance. Focal amplification of JAK2 gene was observed in postchemotherapy triple-negative breast cancers (TNBCs) in a group of 9p24-amplified tumors, suggesting a role in tumorigenicity and chemoresistance. (Balko J M, et al. *Sci Transl Med.* 2016, 8(334):ra53) Therefore, pharmacologic inhibition of the JAK2 signaling pathway can be an important new therapeutic strategy to enhance antitumor activity.

Bruton's tyrosine kinase (BTK) was originally identified in 1993 as a non-receptor protein tyrosine kinase that is defective in the inherited immunodeficiency disease X-linked agammaglobulinaemia (XLA). (Vetrie D. et al. *Nature* 1993, 361, 226-233) BTK functions downstream of the B cell receptor, and is a mediator of B-cell receptor (BCR) signaling. BTK plays a critical role in the development, activation and differentiation of B cells (Mohamed A J et al, *Immunological Reviews,* 2009, 228, 58-73). Abnormal activation of BTK is responsible for aberrant proliferation and homing of various malignant B cells. The irreversible BTK inhibitor ibrutinib was approved for relapsed/refractory chronic lymphocytic leukemia (CLL) & mantle cell lymphoma (MCL), CLL with p17 del and Waldenstrim's macroglobulinemia (WM). Acquired resistance to ibrutinib has been observed in CLL (Furman R R, et al. *New England Journal of Medicine,* 2014, 370, 2352-2354) and MCL (Chiron D, et al. *Cancer Discovery,* 2014, 4, 1022-1035) patients due to mutation of C481S required for covalent binding of ibrutinib to the kinase active site. Ibrutinib inhibited the recombinant BTK C481S 25-fold less potently than WT. (Woyach J A, et al. *New England Journal of Medicine,* 2014, 370, 2286-2294) The loss of covalent binding cysteine leads to ineffective BTK inhibition and ultimately results in ibrutinib resistance. Therefore, the development of reversible ATP competitive BTK inhibitors with comparable activity towards wild type BTK and mutated C481S BTK is necessary to provide an alternative treatment option for patients with acquired resistance to ibrutinib. It was reported that BTK regulates B-cell and macrophage-mediated T-cell suppression in pancreas adenocarcinomas. (Gunderson A J, et al. *Cancer Discov.* 2016, 6, 270-285) The BTK inhibitor ibrutinib restored T cell-dependent antitumor immune responses to inhibit PDAC growth and improved responsiveness to chemotherapy. In addition to its critical roles in B cell development, Btk also contributes to the activation of the FcγR and FcεR signalling pathways in macrophages, neutrophils and mast cells. Btk is a promising target for therapeutic intervention in autoimmune and inflammatory disease, e. g. rheumatoid arthritis (RA) (Di Paolo J A, et al. *Nature Chemical Biology* 2011, 7, 41-50) and systemic lupus erythematosus (SLE). (Bender A T, et al. Clinical Immunology 2016, 164, 65-77) The development of reversible and highly selective BTK inhibitors is highly desired for chronic disease treatment.

SUMMARY

In one aspect, the disclosure relates to of the formula I

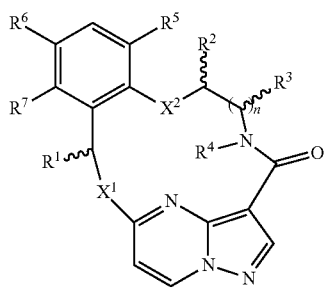

or a pharmaceutically acceptable salt thereof, wherein $X^1$ and $X^2$ are independently S, S(O), S(O)$_2$, O or N(R$^{10}$);

$R^1$ is H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^8$ or —C(O)NR$^8$R$^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-$C_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^8$ or —C(O)NR$^8$R$^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-$C_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^6$ taken together with the atoms to which they are attached optionally form a 5- to 7-membered heterocycloalkyl;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —OC$_1$-$C_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, $C_3$-$C_6$ cycloalkyl, or monocyclic 5- to 7-membered heterocycloalkyl;

$R^5$, $R^6$ and $R^7$ are each independently selected from the group consisting of H, fluoro, chloro, bromo, $C_1$-$C_6$ alkyl, —OH, —CN, —OC$_1$-$C_6$ alkyl, —NHC$_1$-$C_6$ alkyl, —N(C$_1$-C$_6$ alkyl)$_2$, $C_3$-$C_6$ cycloalkyl, 3- to 7-membered heterocycloalkyl, —O—(C$_3$-$C_6$ cycloalkyl), —O-(3- to 7-membered heterocycloalkyl), 5- to 7-membered heteroaryl, $C_6$-$C_{10}$ aryl, and —CF$_3$; wherein each hydrogen atom in $C_1$-$C_6$ alkyl, —OC$_1$-$C_6$ alkyl, —NHC$_1$-$C_6$ alkyl, —N(C$_1$-C$_6$ alkyl)$_2$, $C_3$-$C_6$ cycloalkyl, 3- to 7-membered heterocycloalkyl, —O—(C$_3$-$C_6$ cycloalkyl), —O-(3- to 7-membered heterocycloalkyl), 5- to 7-membered heteroaryl and $C_6$-$C_{10}$ aryl is independently optionally substituted by fluoro, chloro, bromo, —OH, —CN, —OC$_1$-$C_6$ alkyl, —NH$_2$, —NH(C$_1$-C$_6$ alkyl), —N(C$_1$-C$_6$ alkyl)$_2$, $C_3$-$C_7$ cycloalkyl, 3- to 7-membered heterocycloalkyl, $C_6$-$C_{10}$ aryl, 5- to 7-membered heteroaryl, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$;

each $R^8$ and $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^{10}$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —OR$^8$;

n is 1 or 2; and provided that at least one of $R^5$ or $R^7$ is not H.

In some embodiments, the compound of the formula I is not of the formula

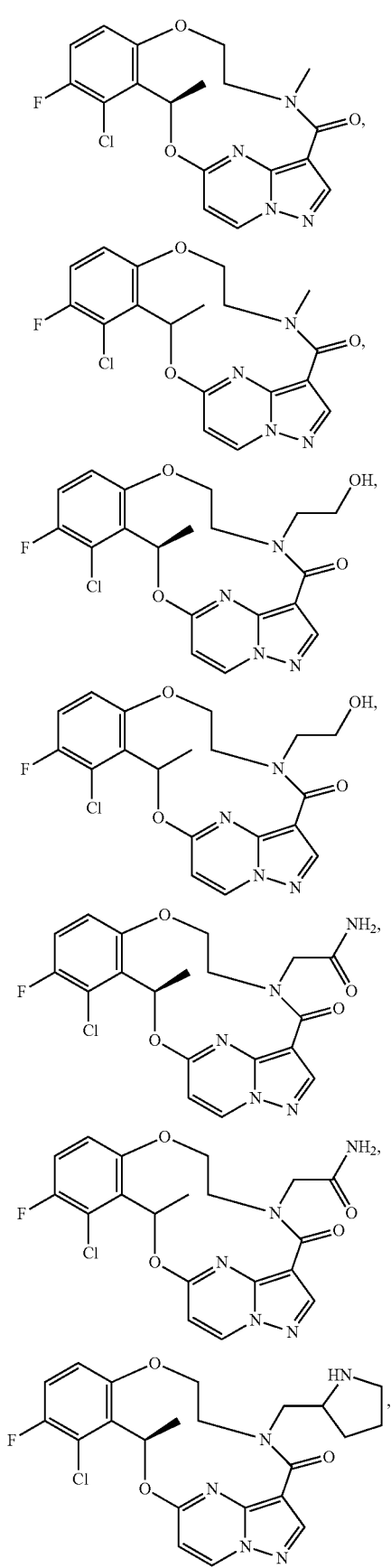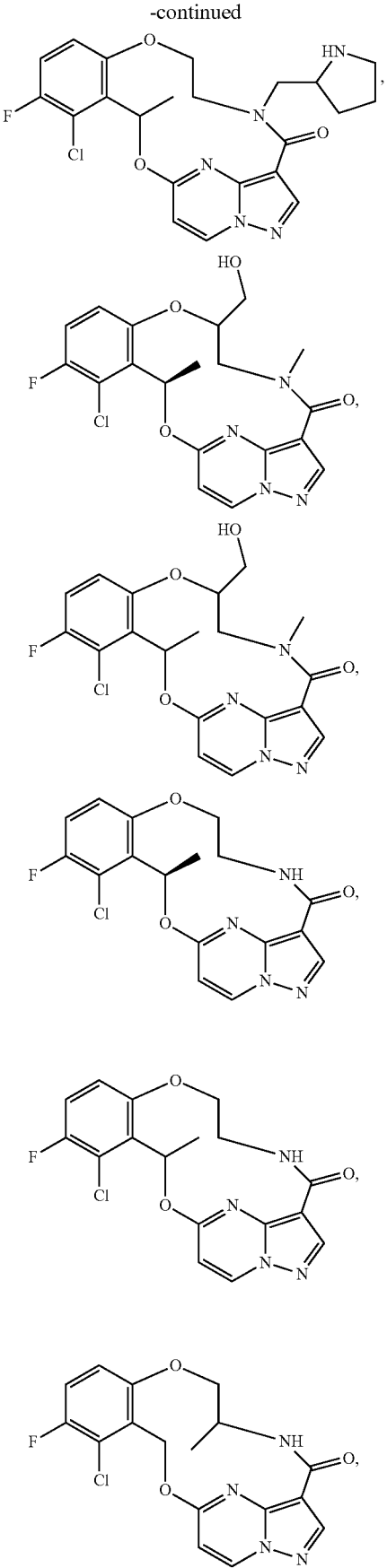

-continued

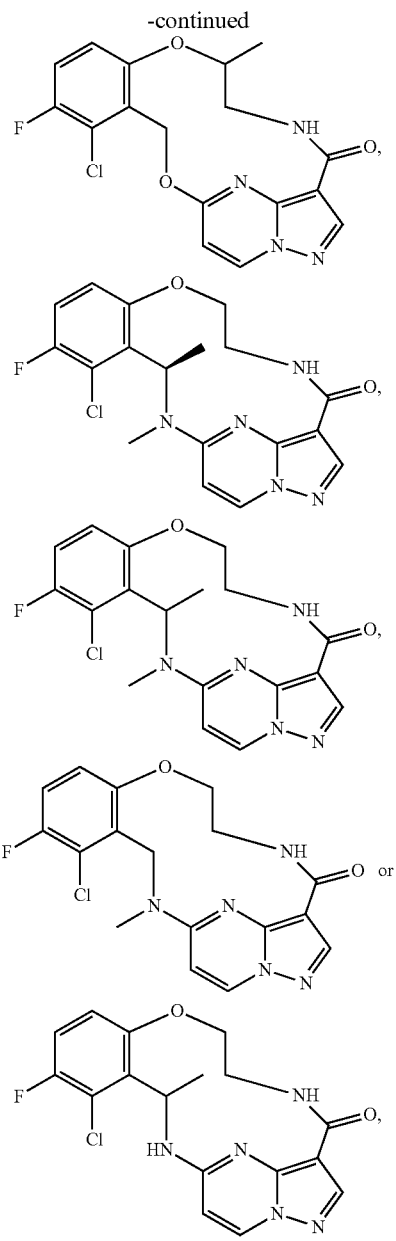

or a pharmaceutically acceptable salt thereof.

In another aspect, the disclosure relates to a compound of the formula Ia

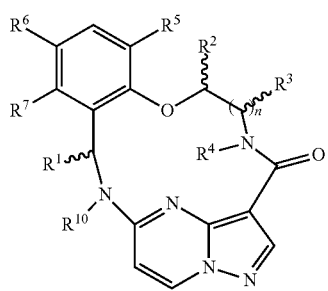

or a pharmaceutically acceptable salt thereof, wherein $R^1$ is H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^8$ or —C(O)N$R^8R^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_0$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^8$ or —C(O)N$R^8R^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^6$ taken together with the atoms to which they are attached optionally form a 5- to 7-membered heterocycloalkyl;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N(C₁-C₆ alkyl)₂, C₃-C₆ cycloalkyl, or monocyclic 5- to 7-membered heterocycloalkyl;

R⁵, R⁶ and R⁷ are each independently selected from the group consisting of H, fluoro, chloro, bromo, C₁-C₆ alkyl, —OH, —CN, —OC₁-C₆ alkyl, —NHC₁-C₆ alkyl, —N(C₁-C₆ alkyl)₂, C₃-C₆ cycloalkyl, 3- to 7-membered heterocycloalkyl, —O—(C₃-C₆ cycloalkyl), —O-(3- to 7-membered heterocycloalkyl), 5- to 7-membered heteroaryl, C₆-C₁₀ aryl, and —CF₃; wherein each hydrogen atom in C₁-C₆ alkyl, —OC₁-C₆ alkyl, —NHC₁-C₆ alkyl, —N(C₁-C₆ alkyl)₂, C₃-C₆ cycloalkyl, 3- to 7-membered heterocycloalkyl, —O—(C₃-C₆ cycloalkyl), —O-(3- to 7-membered heterocycloalkyl), 5- to 7-membered heteroaryl and C₆-C₁₀ aryl is independently optionally substituted by fluoro, chloro, bromo, —OH, —CN, —OC₁-C₆ alkyl, —NH₂, —NH(C₁-C₆ alkyl), —N(C₁-C₆ alkyl)₂, C₃-C₇ cycloalkyl, 3- to 7-membered heterocycloalkyl, C₆-C₁₀ aryl, 5- to 7-membered heteroaryl, —CO₂H, —C(O)OC₁-C₆ alkyl, —C(O)NH₂, —C(O)NH(C₁-C₆ alkyl) and —C(O)N(C₁-C₆ alkyl)₂;

each R⁸ and R⁹ is independently H, deuterium, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl or heteroaryl;

each R¹⁰ is independently H, deuterium, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, or mono- or bicyclic heteroaryl; wherein each hydrogen atom in C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, or mono- or bicyclic heteroaryl is independently optionally substituted by deuterium, halogen, C₁-C₆ alkyl, C₁-C₆ haloalkyl or —OR⁸;

n is 1 or 2;

provided that at least one of R⁵ or R⁷ is not H; and provided that the compound is not of the formula

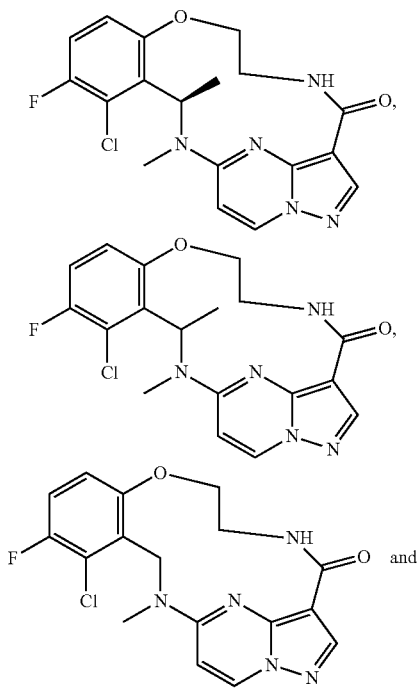

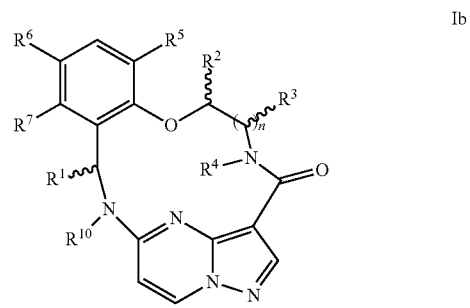

In another aspect, the disclosure relates to a compound of the formula Ib or a pharmaceutically acceptable salt thereof, wherein R¹ is H, deuterium, C₁-C₆ alkyl, C₂-C₆ alkenyl, C₂-C₆ alkynyl, C₃-C₆ cycloalkyl, C₆-C₁₀ aryl, —C(O)OR⁸ or —C(O)NR⁸R⁹; wherein each hydrogen atom in C₁-C₆ alkyl, C₂-C₆ alkenyl, C₂-C₆ alkynyl, C₃-C₆ cycloalkyl and C₆-C₁₀ aryl is independently optionally substituted by deuterium, halogen, —OH, —CN, —OC₁-C₆ alkyl, —NH₂, —NH(C₁-C₆ alkyl), —N(C₁-C₆ alkyl)₂, —NHC(O)C₁-C₆ alkyl, —N(C₁-C₆ alkyl)C(O)C₁-C₆ alkyl, —NHC(O)NH₂, —NHC(O)NHC₁-C₆ alkyl, —N(C₁-C₆ alkyl)C(O)NH₂, —N(C₁-C₆ alkyl)C(O)NHC₁-C₆ alkyl, —NHC(O)N(C₁-C₆ alkyl)₂, —N(C₁-C₆ alkyl)C(O)N(C₁-C₆ alkyl)₂, —NHC(O)OC₁-C₆ alkyl, —N(C₁-C₆ alkyl)C(O)OC₁-C₆ alkyl, —NHS(O)(C₁-C₆ alkyl), —NHS(O)₂(C₁-C₆ alkyl), —N(C₁-C₆ alkyl)S(O)(C₁-C₆ alkyl), —N(C₁-C₆ alkyl)S(O)₂(C₁-C₆ alkyl), —NHS(O)NH₂, —NHS(O)₂NH₂, —N(C₁-C₆ alkyl)S(O)NH₂, —N(C₁-C₆ alkyl)S(O)₂NH₂, —NHS(O)NH(C₁-C₆ alkyl), —NHS(O)₂NH(C₁-C₆ alkyl), —NHS(O)N(C₁-C₆ alkyl)₂, —NHS(O)₂N(C₁-C₆ alkyl)₂, —N(C₁-C₆ alkyl)S(O)NH(C₁-C₆ alkyl), —N(C₁-C₆ alkyl)S(O)₂NH(C₁-C₆ alkyl), —N(C₁-C₆ alkyl)S(O)N(C₁-C₆ alkyl)₂, —N(C₁-C₆ alkyl)S(O)₂N(C₁-C₆ alkyl)₂, —CO₂H, —C(O)OC₁-C₆ alkyl, —C(O)NH₂, —C(O)NH(C₁-C₆ alkyl), —C(O)N(C₁-C₆ alkyl)₂, —SC₁-C₆ alkyl, —S(O)C₁-C₆ alkyl, —S(O)₂C₁-C₆ alkyl, —S(O)NH(C₁-C₆ alkyl), —S(O)₂NH(C₁-C₆ alkyl), —S(O)N(C₁-C₆ alkyl)₂, —S(O)₂N(C₁-C₆ alkyl)₂, —P(C₁-C₆ alkyl)₂, —P(O)(C₁-C₆ alkyl)₂, C₃-C₆ cycloalkyl, or 3- to 7-membered heterocycloalkyl;

each R² and R³ is independently H, deuterium, C₁-C₆ alkyl, C₂-C₆ alkenyl, C₂-C₆ alkynyl, C₃-C₆ cycloalkyl, C₆-C₁₀ aryl, —C(O)OR⁸ or —C(O)NR⁸R⁹; wherein each hydrogen atom in C₁-C₆ alkyl, C₂-C₆ alkenyl, C₂-C₆ alkynyl, C₃-C₆ cycloalkyl and C₆-C₁₀ aryl is independently optionally substituted by deuterium, halogen, —OH, —CN, —OC₁-C₆ alkyl, —NH₂, —NH(C₁-C₆ alkyl), —N(C₁-C₆ alkyl)₂, —NHC(O)C₁-C₆ alkyl, —N(C₁-C₆ alkyl)C(O)C₁-C₆ alkyl, —NHC(O)NH₂, —NHC(O)NHC₁-C₆ alkyl, —N(C₁-C₆ alkyl)C(O)NH₂, —N(C₁-C₆ alkyl)C(O)NHC₁-C₆ alkyl, —NHC(O)N(C₁-C₆ alkyl)₂, —N(C₁-C₆ alkyl)C (O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl; or R$^2$ and R$^3$ taken together with the carbon atoms to which they are attached optionally form a C$_5$-C$_7$ cycloalkyl or a 5- to 7-membered heterocycloalkyl; or R$^2$ and R$^6$ taken together with the atoms to which they are attached optionally form a 5- to 7-membered heterocycloalkyl;

R$^4$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

R$^5$ and R$^6$ are each independently selected from the group consisting of H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, C$_3$-C$_6$ cycloalkyl, 3- to 7-membered heterocycloalkyl, —O—(C$_3$-C$_6$ cycloalkyl), —O-(3- to 7-membered heterocycloalkyl), 5- to 7-membered heteroaryl, C$_6$-C$_{10}$ aryl, and —CF$_3$; wherein each hydrogen atom in C$_1$-C$_6$ alkyl, —OC$_1$-C$_6$ alkyl, —NHC$_1$-C$_6$ alkyl, —N(C$_1$-C$_6$ alkyl)$_2$, C$_3$-C$_6$ cycloalkyl, 3- to 7-membered heterocycloalkyl, —O—(C$_3$-C$_6$ cycloalkyl), —O-(3- to 7-membered heterocycloalkyl), 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, C$_3$-C$_7$ cycloalkyl, 3- to 7-membered heterocycloalkyl, C$_6$-C$_{10}$ aryl, 5- to 7-membered heteroaryl, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$;

R$^7$ is selected from the group consisting of fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, 5- to 7-membered heteroaryl, C$_6$-C$_{10}$ aryl, and —CF$_3$; wherein each hydrogen atom in C$_1$-C$_6$ alkyl, 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$;

each R$^8$ and R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^{10}$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^8$;

n is 1 or 2; and provided that the compound is not of the formula

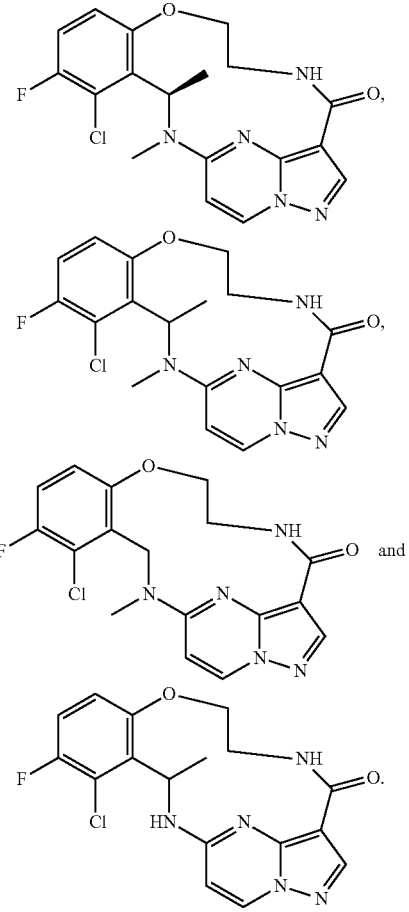

In another aspect, the disclosure relates to a compound of the formula Ic

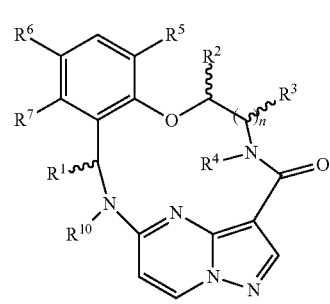

or a pharmaceutically acceptable salt thereof, wherein

R$^1$ is H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^8$ or —C(O)NR$^8$R$^9$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-

$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NHC$_1$-$C_6$ alkyl, —N($C_1$-$C_6$ alkyl)C(O)NH$_2$, —N($C_1$-$C_6$ alkyl)C(O)NHC$_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^8$ or —C(O)NR$^8$R$^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^6$ taken together with the atoms to which they are attached optionally form a 5- to 7-membered heterocycloalkyl;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

$R^5$ is selected from the group consisting of fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl, $C_6$-$C_{10}$ aryl, and —CF$_3$; wherein each hydrogen atom in $C_1$-$C_6$ alkyl, —O$C_1$-$C_6$ alkyl, —NH$C_1$-$C_6$ alkyl, —N($C_1$-$C_6$ alkyl)$_2$, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl and $C_6$-$C_{10}$ aryl is independently optionally substituted by fluoro, chloro, bromo, —OH, —CN, —O$C_1$-$C_6$ alkyl, —NH$_2$, —NH($C_1$-$C_6$ alkyl), —N($C_1$-$C_6$ alkyl)$_2$, $C_3$-$C_7$ cycloalkyl, 3- to 7-membered heterocycloalkyl, $C_6$-$C_{10}$ aryl, 5- to 7-membered heteroaryl, —CO$_2$H, —C(O)O$C_1$-$C_6$ alkyl, —C(O)NH$_2$, —C(O)NH($C_1$-$C_6$ alkyl) and —C(O)N($C_1$-$C_6$ alkyl)$_2$;

$R^6$ and $R^7$ are each independently selected from the group consisting of H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$, 5- to 7-membered heteroaryl, $C_6$-$C_{10}$ aryl, and —CF$_3$; wherein each hydrogen atom in $C_1$-$C_6$ alkyl, 5- to 7-membered heteroaryl and $C_6$-$C_{10}$ aryl is independently optionally substituted by fluoro, chloro, bromo, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl) and —C(O)N($C_1$-$C_6$ alkyl)$_2$;

each $R^8$ and $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^{10}$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —OR; and n is 1 or 2.

In another aspect, the disclosure relates to a pharmaceutical composition comprising a compound of the formula I, Ia, Ib or Ic, or a pharmaceutically acceptable salt thereof, and optionally at least one diluent, carrier or excipient.

In another aspect, the disclosure is directed to a method of treating cancer, pain, neurological diseases, autoimmune diseases, or inflammation comprising administering to a subject in need of such treatment an effective amount of at least one compound of formula I, Ia, Ib or Ic, or a pharmaceutically acceptable salt thereof. cancer, pain, neurological diseases, autoimmune diseases, or inflammation.

In another aspect, the disclosure is directed to use of a compound of formula I, Ia, Ib or Ic, or a pharmaceutically acceptable salt thereof, in the preparation of a medicament for the treatment of cancer, pain, neurological diseases, autoimmune diseases, or inflammation. In some embodiments, the disease is a cancer. In some embodiments, the disease is an autoimmune disease. In some embodiments, the disease is inflammation.

In another aspect, the disclosure is directed to use of a compound of formula I, Ia, Ib or Ic, or a pharmaceutically acceptable salt thereof, for treating cancer, pain, neurological diseases, autoimmune diseases, or inflammation. In some embodiments, the disease is a cancer. In some embodiments, the disease is an autoimmune disease. In some embodiments, the disease is inflammation.

In another aspect, the disclosure is directed to use of a compound of formula I, Ia, Ib or Ic, or a pharmaceutically acceptable salt thereof, in the preparation of a medicament for the treatment of cancer, pain, neurological diseases, autoimmune diseases, or inflammation, and the use of such compounds and salts for treatment of cancer, pain, neurological diseases, autoimmune diseases, or inflammation. In some embodiments, the disease is a cancer. In some embodiments, the disease is an autoimmune disease. In some embodiments, the disease is inflammation.

In yet another aspect, the disclosure relates to a method of inhibiting non-receptor tyrosine kinases, including one or more of JAK2 or BTK, comprising contacting a cell comprising one or more of such kinases with an effective amount of at least one compound of formula I, Ia, Ib or Ic, or a pharmaceutically acceptable salt thereof, and/or with at least one pharmaceutical composition of the disclosure, wherein the contacting is in vitro, ex vivo, or in vivo.

Additional embodiments, features, and advantages of the disclosure will be apparent from the following detailed description and through practice of the disclosure. The compounds of the present disclosure can be described as embodiments in any of the following enumerated clauses. It will be understood that any of the embodiments described herein can be used in connection with any other embodiments described herein to the extent that the embodiments do not contradict one another.

1. A compound of the formula I

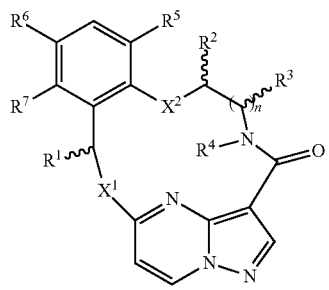

I or a pharmaceutically acceptable salt thereof, wherein $X^1$ and $X^2$ are independently S, S(O), S(O)$_2$, O or N(R$^{10}$);

$R^1$ is H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^8$ or —C(O)NR$^8$R$^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-$C_6$ alkyl, —NH$_2$, —NH(C$_1$-$C_6$ alkyl), —N(C$_1$-$C_6$ alkyl)$_2$, —NHC(O)C$_1$-$C_6$ alkyl, —N(C$_1$-$C_6$ alkyl)C(O)C$_1$-$C_6$ alkyl, —NHC(O)NH$_2$, —NHC(O)NHC$_1$-$C_6$ alkyl, —N(C$_1$-$C_6$ alkyl)C(O)NH$_2$, —N(C$_1$-$C_6$ alkyl)C(O)NHC$_1$-$C_6$ alkyl, —NHC(O)N(C$_1$-$C_6$ alkyl)$_2$, —N(C$_1$-$C_6$ alkyl)C(O)N(C$_1$-$C_6$ alkyl)$_2$, —NHC(O)OC$_1$-$C_6$ alkyl, —N(C$_1$-$C_6$ alkyl)C(O)OC$_1$-$C_6$ alkyl, —NHS(O)(C$_1$-$C_6$ alkyl), —NHS(O)$_2$(C$_1$-$C_6$ alkyl), —N(C$_1$-$C_6$ alkyl)S(O)(C$_1$-$C_6$ alkyl), —N(C$_1$-$C_6$ alkyl)S(O)$_2$(C$_1$-$C_6$ alkyl), —NHS(O)NH$_2$, —NHS(O)$_2$NH$_2$, —N(C$_1$-$C_6$ alkyl)S(O)NH$_2$, —N(C$_1$-$C_6$ alkyl)S(O)$_2$NH$_2$, —NHS(O)NH(C$_1$-$C_6$ alkyl), —NHS(O)$_2$NH(C$_1$-$C_6$ alkyl), —NHS(O)N(C$_1$-$C_6$ alkyl)$_2$, —NHS(O)$_2$N(C$_1$-$C_6$ alkyl)$_2$, —N(C$_1$-$C_6$ alkyl)S(O)NH(C$_1$-$C_6$ alkyl), —N(C$_1$-$C_6$ alkyl)S(O)$_2$NH(C$_1$-$C_6$ alkyl), —N(C$_1$-$C_6$ alkyl)S(O)N(C$_1$-$C_6$ alkyl)$_2$, —N(C$_1$-$C_6$ alkyl)S(O)$_2$N(C$_1$-$C_6$ alkyl)$_2$, —CO$_2$H, —C(O)OC$_1$-$C_6$ alkyl, —C(O)NH$_2$, —C(O)NH(C$_1$-$C_6$ alkyl), —C(O)N(C$_1$-$C_6$ alkyl)$_2$, —SC$_1$-$C_6$ alkyl, —S(O)C$_1$-$C_6$ alkyl, —S(O)$_2$C$_1$-$C_6$ alkyl, —S(O)NH(C$_1$-$C_6$ alkyl), —S(O)$_2$NH(C$_1$-$C_6$ alkyl), —S(O)N(C$_1$-$C_6$ alkyl)$_2$, —S(O)$_2$N(C$_1$-$C_6$ alkyl)$_2$, —P(C$_1$-$C_6$ alkyl)$_2$, —P(O)(C$_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)OR$^8$ or —C(O)NR$^8$R$^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —OC$_1$-$C_6$ alkyl, —NH$_2$, —NH(C$_1$-$C_6$ alkyl), —N(C$_1$-$C_6$ alkyl)$_2$, —NHC(O)C$_1$-$C_6$ alkyl, —N(C$_1$-$C_6$ alkyl)C(O)C$_1$-$C_6$ alkyl, —NHC(O)NH$_2$, —NHC(O)NHC$_1$-$C_6$ alkyl, —N(C$_1$-$C_6$ alkyl)C(O)NH$_2$, —N(C$_1$-$C_6$ alkyl)C(O)NHC$_1$-$C_6$ alkyl, —NHC(O)N(C$_1$-$C_6$ alkyl)$_2$, —N(C$_1$-$C_6$ alkyl)C(O)N(C$_1$-$C_6$ alkyl)$_2$, —NHC(O)OC$_1$-$C_6$ alkyl, —N(C$_1$-$C_6$ alkyl)C(O)OC$_1$-$C_6$ alkyl, —NHS(O)(C$_1$-$C_6$ alkyl), —NHS(O)$_2$(C$_1$-$C_6$ alkyl), —N(C$_1$-$C_6$ alkyl)S(O)(C$_1$-$C_6$ alkyl), —N(C$_1$-$C_6$ alkyl)S(O)$_2$(C$_1$-$C_6$ alkyl), —NHS(O)NH$_2$, —NHS(O)$_2$NH$_2$, —N(C$_1$-$C_6$ alkyl)S(O)NH$_2$, —N(C$_1$-$C_6$ alkyl)S(O)$_2$NH$_2$, —NHS(O)NH(C$_1$-$C_6$ alkyl), —NHS(O)$_2$NH(C$_1$-$C_6$ alkyl), —NHS(O)N(C$_1$-$C_6$ alkyl)$_2$, —NHS(O)$_2$N(C$_1$-$C_6$ alkyl)$_2$, —N(C$_1$-$C_6$ alkyl)S(O)NH(C$_1$-$C_6$ alkyl), —N(C$_1$-$C_6$ alkyl)S(O)$_2$NH(C$_1$-$C_6$ alkyl), —N(C$_1$-$C_6$ alkyl)S(O)N(C$_1$-$C_6$ alkyl)$_2$, —N(C$_1$-$C_6$ alkyl)S(O)$_2$N(C$_1$-$C_6$ alkyl)$_2$, —CO$_2$H, —C(O)OC$_1$-$C_6$ alkyl, —C(O)NH$_2$, —C(O)NH(C$_1$-$C_6$ alkyl), —C(O)N(C$_1$-$C_6$ alkyl)$_2$, —SC$_1$-$C_6$ alkyl, —S(O)C$_1$-$C_6$ alkyl, —S(O)$_2$C$_1$-$C_6$ alkyl, —S(O)NH(C$_1$-$C_6$ alkyl), —S(O)$_2$NH(C$_1$-$C_6$ alkyl), —S(O)N(C$_1$-$C_6$ alkyl)$_2$, —S(O)$_2$N(C$_1$-$C_6$ alkyl)$_2$, —P(C$_1$-$C_6$ alkyl)$_2$, —P(O)(C$_1$-$C_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^6$ taken together with the atoms to which they are attached optionally form a 5- to 7-membered heterocycloalkyl;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —OC$_1$-$C_6$ alkyl, —NH$_2$, —NH(C$_1$-$C_6$ alkyl), —N(C$_1$-$C_6$ alkyl)$_2$, —CO$_2$H, —C(O)OC$_1$-$C_6$ alkyl, —C(O)NH$_2$, —C(O)NH(C$_1$-$C_6$ alkyl), —C(O)N(C$_1$-$C_6$ alkyl)$_2$, $C_3$-$C_6$ cycloalkyl, or monocyclic 5- to 7-membered heterocycloalkyl;

$R^5$, $R^6$ and $R^7$ are each independently selected from the group consisting of H, fluoro, chloro, bromo, $C_1$-$C_6$ alkyl, —OH, —CN, —OC$_1$-$C_6$ alkyl, —NHC$_1$-$C_6$ alkyl, —N(C$_1$-$C_6$ alkyl)$_2$, $C_3$-$C_6$ cycloalkyl, 3- to 7-membered heterocycloalkyl, —O—(C$_3$-$C_6$ cycloalkyl), —O-(3- to 7-membered heterocycloalkyl), 5- to 7-membered heteroaryl, $C_6$-$C_{10}$ aryl, and —CF$_3$; wherein each hydrogen atom in $C_1$-$C_6$ alkyl, —OC$_1$-$C_6$ alkyl, —NHC$_1$-$C_6$ alkyl, —N(C$_1$-$C_6$ alkyl)$_2$, $C_3$-$C_6$ cycloalkyl, 3- to 7-membered heterocycloalkyl, —O—(C$_3$-$C_6$ cycloalkyl), —O-(3- to 7-membered heterocycloalkyl), 5- to 7-membered heteroaryl and $C_6$-$C_{10}$ aryl is independently optionally substituted by fluoro, chloro, bromo, —OH, —CN, —OC$_1$-$C_6$ alkyl, —NH$_2$, —NH(C$_1$-$C_6$ alkyl), —N(C$_1$-$C_6$ alkyl)$_2$, $C_3$-$C_7$ cycloalkyl, 3- to 7-membered heterocycloalkyl, $C_6$-$C_{10}$ aryl, 5- to 7-membered heteroaryl, —CO$_2$H, —C(O)OC$_1$-$C_6$ alkyl, —C(O)NH$_2$, —C(O)NH(C$_1$-$C_6$ alkyl) and —C(O)N(C$_1$-$C_6$ alkyl)$_2$;

each $R^8$ and $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^{10}$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, C$_1$-C$_6$ alkyl, C$_1$-C$_6$ haloalkyl or —OR$^8$;

n is 1 or 2; and provided that at least one of R$^5$ or R$^7$ is not H.

2. The compound of clause 1, or a pharmaceutically acceptable salt thereof, wherein X$^1$ is N(R$^{10}$).

3. The compound of any one of the preceding clauses, or a pharmaceutically acceptable salt thereof, wherein X$^2$ is O.

4. A compound of the formula Ia

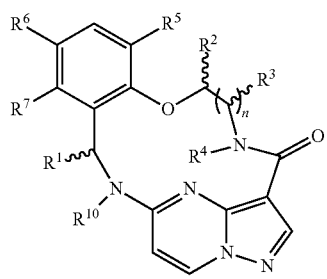

Ia or a pharmaceutically acceptable salt thereof, wherein

R$^1$ is H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^8$ or —C(O)NR$^8$R$^9$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^8$ or —C(O)NR$^8$R$^9$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl; or R$^2$ and R$^3$ taken together with the carbon atoms to which they are attached optionally form a C$_5$-C$_7$ cycloalkyl or a 5- to 7-membered heterocycloalkyl; or R$^2$ and R$^6$ taken together with the atoms to which they are attached optionally form a 5- to 7-membered heterocycloalkyl;

R$^4$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

R$^5$, R$^6$ and R$^7$ are each independently selected from the group consisting of H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, C$_3$-C$_6$ cycloalkyl, 3- to 7-membered heterocycloalkyl, —O—(C$_3$-C$_6$ cycloalkyl), —O-(3- to 7-membered heterocycloalkyl), 5- to 7-membered heteroaryl, C$_6$-C$_{10}$ aryl, and —CF$_3$; wherein each hydrogen atom in C$_1$-C$_6$ alkyl, —OC$_1$-C$_6$ alkyl, —NHC$_1$-C$_6$ alkyl, —N(C$_1$-C$_6$ alkyl)$_2$, C$_3$-C$_6$ cycloalkyl, 3- to 7-membered heterocycloalkyl, —O—(C$_3$-C$_6$ cycloalkyl), —O-(3- to 7-membered heterocycloalkyl), 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, C$_3$-C$_7$ cycloalkyl, 3- to 7-membered heterocycloalkyl, C$_6$-C$_{10}$ aryl, 5- to 7-membered heteroaryl, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$;

each R$^8$ and R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^{10}$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^8$;

n is 1 or 2;

provided that at least one of R$^5$ or R$^7$ is not H; and provided that the compound is not of

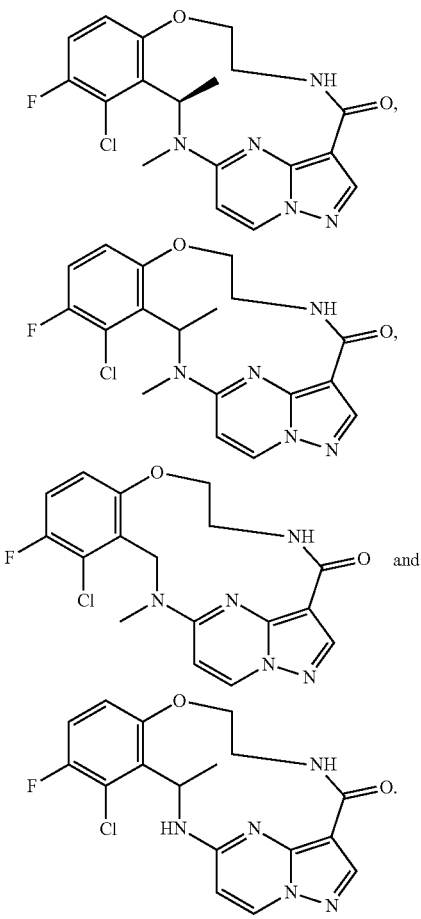

5. The compound of any one of the preceding clauses, or a pharmaceutically acceptable salt thereof, wherein $R^7$ is selected from the group consisting of fluoro, chloro, bromo, $C_1$-$C_6$ alkyl, —OH, —CN, —$OC_1$-$C_6$ alkyl, —$NHC_1$-$C_6$ alkyl, —$N(C_1$-$C_6$ alkyl$)_2$, 5- to 7-membered heteroaryl, $C_6$-$C_{10}$ aryl, and —$CF_3$; wherein each hydrogen atom in $C_1$-$C_6$ alkyl, 5- to 7-membered heteroaryl and $C_6$-$C_{10}$ aryl is independently optionally substituted by fluoro, chloro, bromo, —OH, —CN, —$OC_1$-$C_6$ alkyl, —$NH_2$, —$NH(C_1$-$C_6$ alkyl), —$N(C_1$-$C_6$ alkyl$)_2$, —$CO_2H$, —$C(O)OC_1$-$C_6$ alkyl, —$C(O)NH_2$, —$C(O)NH(C_1$-$C_6$ alkyl) and —$C(O)N(C_1$-$C_6$ alkyl$)_2$.

6. The compound of any one of the preceding clauses, or a pharmaceutically acceptable salt thereof, wherein $R^7$ is selected from the group consisting of fluoro, chloro, bromo, $C_1$-$C_6$ alkyl, —OH, —CN, —$OC_1$-$C_6$ alkyl, 5- to 7-membered heteroaryl, and —$CF_3$.

7. The compound of any one of the preceding clauses, or a pharmaceutically acceptable salt thereof, wherein $R^7$ is fluoro.

8. The compound of any one of clauses 1 to 6, or a pharmaceutically acceptable salt thereof, wherein $R^7$ is chloro.

9. The compound of any one of clauses 1 to 6, or a pharmaceutically acceptable salt thereof, wherein $R^7$ is —CN.

10. The compound of any one of clauses 1 to 6, or a pharmaceutically acceptable salt thereof, wherein $R^7$ is —$CF_3$.

11. The compound of any one clauses 1 to 4, or a pharmaceutically acceptable salt thereof, wherein $R^5$ is selected from the group consisting of fluoro, chloro, bromo, $C_1$-$C_6$ alkyl, —OH, —CN, —$OC_1$-$C_6$ alkyl, —$NHC_1$-$C_6$ alkyl, —$N(C_1$-$C_6$ alkyl$)_2$, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl, $C_6$-$C_{10}$ aryl, and —$CF_3$; wherein each hydrogen atom in $C_1$-$C_6$ alkyl, —$OC_1$-$C_6$ alkyl, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl and $C_6$-$C_{10}$ aryl is independently optionally substituted by fluoro, chloro, bromo, —OH, —CN, —$OC_1$-$C_6$ alkyl, —$NH_2$, —$NH(C_1$-$C_6$ alkyl), —$N(C_1$-$C_6$ alkyl$)_2$, $C_3$-$C_7$ cycloalkyl, 3- to 7-membered heterocycloalkyl, $C_6$-$C_{10}$ aryl, 5- to 7-membered heteroaryl, —$CO_2H$, —$C(O)OC_1$-$C_6$ alkyl, —$C(O)NH_2$, —$C(O)NH(C_1$-$C_6$ alkyl) and —$C(O)N(C_1$-$C_6$ alkyl$)_2$.

12. The compound of any one clauses 1 to 4 or 11, or a pharmaceutically acceptable salt thereof, wherein $R^5$ is selected from the group consisting of fluoro, chloro, bromo, $C_1$-$C_6$ alkyl, —OH, —CN, —$OC_1$-$C_6$ alkyl, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl, $C_6$-$C_{10}$ aryl and —$CF_3$, wherein each hydrogen atom in $C_1$-$C_6$ alkyl, —$OC_1$-$C_6$ alkyl, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl and $C_6$-$C_{10}$ aryl is independently optionally substituted by fluoro, chloro, bromo, —OH, —CN, —$OC_1$-$C_6$ alkyl, —$NH_2$, —$NH(C_1$-$C_6$ alkyl), —$N(C_1$-$C_6$ alkyl$)_2$, $C_3$-$C_7$ cycloalkyl, 3- to 7-membered heterocycloalkyl, $C_6$-$C_{10}$ aryl, 5- to 7-membered heteroaryl, —$CO_2H$, —$C(O)OC_1$-$C_6$ alkyl, —$C(O)NH_2$, —$C(O)NH(C_1$-$C_6$ alkyl) and —$C(O)N(C_1$-$C_6$ alkyl$)_2$.

13. The compound of any one clauses 1 to 4, 11 or 12, or a pharmaceutically acceptable salt thereof, wherein $R^5$ is fluoro.

14. The compound of any one clauses 1 to 4, 11 or 12, or a pharmaceutically acceptable salt thereof, wherein $R^5$ is chloro.

15. The compound of any one clauses 1 to 4, 11 or 12, or a pharmaceutically acceptable salt thereof, wherein $R^5$ is bromo.

16. The compound of any one clauses 1 to 4, 11 or 12, or a pharmaceutically acceptable salt thereof, wherein $R^5$ is —$OC_1$-$C_6$ alkyl.

17. The compound of clause 16, wherein $R^5$ is methoxy, ethoxy, iso-propoxy, or n-propoxy.

18. The compound of any one clauses 1 to 4, 11 or 12, or a pharmaceutically acceptable salt thereof, wherein $R^5$ is —OH.

19. The compound of any one clauses 1 to 4, 11 or 12, or a pharmaceutically acceptable salt thereof, wherein $R^5$ is —CN.

20. The compound of any one clauses 1 to 4, 11 or 12, or a pharmaceutically acceptable salt thereof, wherein $R^5$ is —$CF_3$.

21. The compound of any one clauses 1 to 4, 11 or 12, or a pharmaceutically acceptable salt thereof, wherein $R^5$ is 5- to 7-membered heteroaryl; wherein each hydrogen atom in 5- to 7-membered heteroaryl is independently optionally substituted by fluoro, chloro, bromo, —OH, —CN, —$OC_1$-$C_6$ alkyl, —$NH_2$, —$NH(C_1$-$C_6$ alkyl), —$N(C_1$-$C_6$ alkyl$)_2$, —$CO_2H$, —$C(O)OC_1$-$C_6$ alkyl, —$C(O)NH_2$, —$C(O)NH(C_1$-$C_6$ alkyl) and —$C(O)N(C_1$-$C_6$ alkyl$)_2$.

22. The compound of clause 21, or a pharmaceutically acceptable salt thereof, wherein 5- to 7-membered heteroaryl is pyrrolyl, furanyl, thiophenyl, imidazolyl, pyrazolyl, pyridinyl, pyrimidinyl, quinolinyl, isoquinolinyl, purinyl, tetrazolyl, triazinyl or pyrazinyl, optionally substituted with one or more substituents selected from the group consisting of fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$.

23. The compound of clause 21, or a pharmaceutically acceptable salt thereof, wherein 5- to 7-membered heteroaryl is pyrazolyl substituted with one or more substituents selected from the group consisting of fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$.

24. The compound of clause 21, or a pharmaceutically acceptable salt thereof, wherein 5- to 7-membered heteroaryl is pyridinyl substituted with one or more substituents selected from the group consisting of fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$.

25. The compound of clause 21, or a pharmaceutically acceptable salt thereof, wherein 5- to 7-membered heteroaryl is

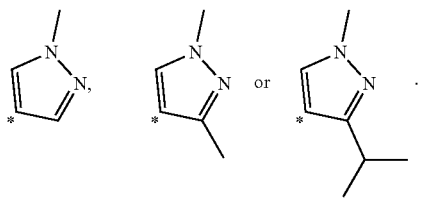

26. The compound of any one clauses 1 to 4, 11 or 12, or a pharmaceutically acceptable salt thereof, wherein R$^5$ is C$_6$-C$_{10}$ aryl, wherein each hydrogen atom in C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$.

27. A compound of the formula Ib

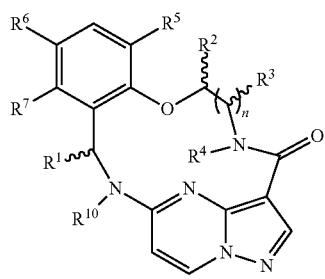

or a pharmaceutically acceptable salt thereof, wherein

R$^1$ is H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^8$ or —C(O)NR$^8$R$^9$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^8$ or —C(O)NR$^8$R$^9$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl; or R$^2$ and R$^3$ taken together with the carbon atoms to which they are attached optionally form a C$_5$-C$_7$ cycloalkyl or a 5- to 7-membered heterocycloalkyl; or R$^2$ and R$^6$ taken together with the atoms to which they are attached optionally form a 5- to 7-membered heterocycloalkyl;

R$^4$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

R$^5$ and R$^6$ are each independently selected from the group consisting of H, fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, C$_3$-C$_6$ cycloalkyl, 3- to 7-membered heterocycloalkyl, —O—(C$_3$-C$_6$ cycloalkyl), —O-(3- to 7-membered heterocycloalkyl), 5- to 7-membered heteroaryl, C$_6$-C$_{10}$ aryl, and —CF$_3$; wherein each hydrogen atom in C$_1$-C$_6$ alkyl, —OC$_1$-C$_6$ alkyl, —NHC$_1$-C$_6$ alkyl, —N(C$_1$-C$_6$ alkyl)$_2$, C$_3$-C$_6$ cycloalkyl, 3- to 7-membered heterocycloalkyl, —O—(C$_3$-C$_6$ cycloalkyl), —O-(3- to 7-membered heterocycloalkyl), 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NHC$_1$-C$_6$ alkyl), —N(C$_1$-C$_6$ alkyl)$_2$, C$_3$-C$_7$ cycloalkyl, 3- to 7-membered heterocycloalkyl, C$_6$-C$_{10}$ aryl, 5- to 7-membered heteroaryl, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$;

R$^7$ is selected from the group consisting of fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, 5- to 7-membered heteroaryl, C$_6$-C$_{10}$ aryl, and —CF$_3$; wherein each hydrogen atom in C$_1$-C$_6$ alkyl, 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$;

each R$^8$ and R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl or heteroaryl;

each R$^{10}$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl; wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^8$;

n is 1 or 2; and provided that the compound is not of the formula

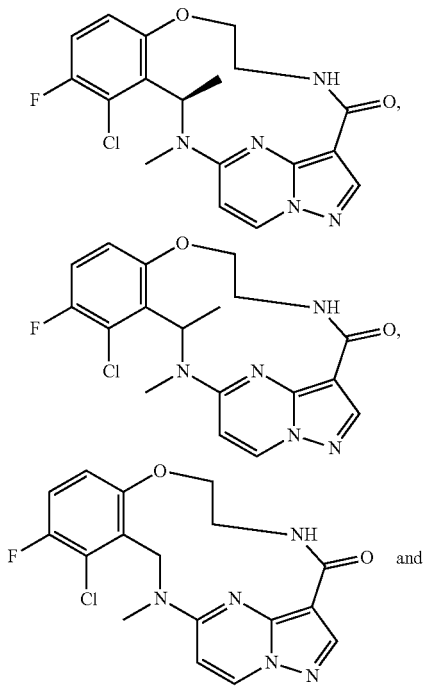

-continued

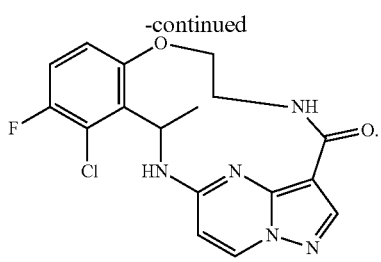

28. The compound of clause 27, or a pharmaceutically acceptable salt thereof, wherein R$^7$ is selected from the group consisting of fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, 5- to 7-membered heteroaryl, C$_6$-C$_{10}$ aryl, and —CF$_3$; wherein each hydrogen atom in C$_1$-C$_6$ alkyl, 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$.

29. The compound of clause 27 or 28, or a pharmaceutically acceptable salt thereof, wherein R$^7$ is selected from the group consisting of fluoro, chloro, bromo, C$_1$-C$_6$ alkyl, —OH, —CN, —OC$_1$-C$_6$ alkyl, 5- to 7-membered heteroaryl, and —CF$_3$.

30. The compound of any one of clauses 27 to 29, or a pharmaceutically acceptable salt thereof, wherein R$^7$ is fluoro.

31. The compound of any one of clauses 27 to 29, or a pharmaceutically acceptable salt thereof, wherein R$^7$ is chloro.

32. The compound of any one of clauses 27 to 29, or a pharmaceutically acceptable salt thereof, wherein R$^7$ is —CN.

33. The compound of any one of clauses 27 to 29, or a pharmaceutically acceptable salt thereof, wherein R$^7$ is —CF$_3$.

34. A compound of the formula Ic

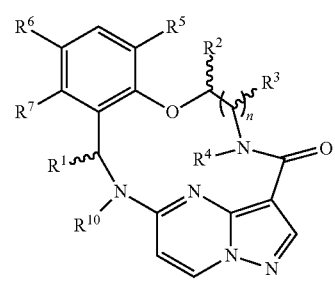

or a pharmaceutically acceptable salt thereof, wherein
R$^1$ is H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^8$ or —C(O)NR$^8$R$^9$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl;

each $R^2$ and $R^3$ is independently H, deuterium, $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, —C(O)O$R^8$ or —C(O)N$R^8R^9$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, —OH, —CN, —O$C_1$-$C_6$ alkyl, —NH$_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)NH$_2$, —NHC(O)NH$C_1$-$C_6$ alkyl, —N($C_1$-$C_6$ alkyl)C(O)NH$_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)O$C_1$-$C_6$ alkyl, —N($C_1$-$C_6$ alkyl)C(O)O$C_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)NH$_2$, —NHS(O)$_2$NH$_2$, —N($C_1$-$C_6$ alkyl)S(O)NH$_2$, —N($C_1$-$C_6$ alkyl)S(O)$_2$NH$_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, —S$C_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl; or $R^2$ and $R^3$ taken together with the carbon atoms to which they are attached optionally form a $C_5$-$C_7$ cycloalkyl or a 5- to 7-membered heterocycloalkyl; or $R^2$ and $R^6$ taken together with the atoms to which they are attached optionally form a 5- to 7-membered heterocycloalkyl;

$R^4$ is H, $C_1$-$C_6$ alkyl or 3- to 7-membered heterocycloalkyl, wherein each hydrogen atom in $C_1$-$C_6$ alkyl or 3- to 7-membered heterocycloalkyl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl), —C(O)N($C_1$-$C_6$ alkyl)$_2$, $C_3$-$C_6$ cycloalkyl, or monocyclic 5- to 7-membered heterocycloalkyl;

$R^5$ is selected from the group consisting of fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl, $C_6$-$C_{10}$ aryl, and —CF$_3$; wherein each hydrogen atom in $C_1$-$C_6$ alkyl, —O$C_1$-$C_6$ alkyl, —NH$C_1$-$C_6$ alkyl, —N($C_1$-$C_6$ alkyl)$_2$, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl and $C_6$-$C_{10}$ aryl is independently optionally substituted by fluoro, chloro, bromo, —OH, —CN, —O$C_1$-$C_6$ alkyl, —NH$_2$, —NH($C_1$-$C_6$ alkyl), —N($C_1$-$C_6$ alkyl)$_2$, $C_3$-$C_7$ cycloalkyl, 3- to 7-membered heterocycloalkyl, $C_6$-$C_{10}$ aryl, 5- to 7-membered heteroaryl, —CO$_2$H, —C(O)O$C_1$-$C_6$ alkyl, —C(O)NH$_2$, —C(O)NH($C_1$-$C_6$ alkyl) and —C(O)N($C_1$-$C_6$ alkyl)$_2$;

$R^6$ and $R^7$ are each independently selected from the group consisting of H, fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$, 5- to 7-membered heteroaryl, $C_6$-$C_{10}$ aryl, and —CF$_3$; wherein each hydrogen atom in $C_1$-$C_6$ alkyl, 5- to 7-membered heteroaryl and $C_6$-$C_{10}$ aryl is independently optionally substituted by fluoro, chloro, bromo, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl) and —C(O)N($C_1$-$C_6$ alkyl)$_2$;

each $R^8$ and $R^9$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl or heteroaryl;

each $R^{10}$ is independently H, deuterium, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl; wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by deuterium, halogen, $C_1$-$C_6$ alkyl, $C_1$-$C_6$ haloalkyl or —OR; and n is 1 or 2.

35. The compound of clauses 34, or a pharmaceutically acceptable salt thereof, wherein $R^5$ is selected from the group consisting of fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl, $C_6$-$C_{10}$ aryl, and —CF$_3$; wherein each hydrogen atom in $C_1$-$C_6$ alkyl, —O$C_1$-$C_6$ alkyl, —NH$C_1$-$C_6$ alkyl, —N($C_1$-$C_6$ alkyl)$_2$, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl and $C_6$-$C_{10}$ aryl is independently optionally substituted by fluoro, chloro, bromo, —OH, —CN, —O$C_1$-$C_6$ alkyl, —NH$_2$, —NH($C_1$-$C_6$ alkyl), —N($C_1$-$C_6$ alkyl)$_2$, $C_3$-$C_7$ cycloalkyl, 3- to 7-membered heterocycloalkyl, $C_6$-$C_{10}$ aryl, 5- to 7-membered heteroaryl, —CO$_2$H, —C(O)O$C_1$-$C_6$ alkyl, —C(O)NH$_2$, —C(O)NH($C_1$-$C_6$ alkyl) and —C(O)N($C_1$-$C_6$ alkyl)$_2$.

36. The compound of clause 34 or 35, or a pharmaceutically acceptable salt thereof, wherein $R^5$ is selected from the group consisting of fluoro, chloro, bromo, $C_1$-$C_6$ alkyl, —OH, —CN, —O$C_1$-$C_6$ alkyl, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl, $C_6$-$C_{10}$ aryl and —CF$_3$, wherein each hydrogen atom in $C_1$-$C_6$ alkyl, —O$C_1$-$C_6$ alkyl, $C_3$-$C_6$ cycloalkyl, 3- to 7-membered heterocycloalkyl, —O—($C_3$-$C_6$ cycloalkyl), —O-(3- to 7-membered heterocycloalkyl), 5- to 7-membered heteroaryl and $C_6$-$C_{10}$ aryl is independently optionally substituted by fluoro, chloro, bromo, —OH, —CN, —O$C_1$-$C_6$ alkyl, —NH$_2$, —NH($C_1$-$C_6$ alkyl), —N($C_1$-$C_6$ alkyl)$_2$, $C_3$-$C_7$ cycloalkyl, 3- to 7-membered heterocycloalkyl, $C_6$-$C_{10}$ aryl, 5- to 7-membered heteroaryl, —CO$_2$H, —C(O)O$C_1$-$C_6$ alkyl, —C(O)NH$_2$, —C(O)NH($C_1$-$C_6$ alkyl) and —C(O)N($C_1$-$C_6$ alkyl)$_2$.

37. The compound of any one clauses 34 to 36, or a pharmaceutically acceptable salt thereof, wherein $R^5$ is fluoro.

38. The compound of any one clauses 34 to 36, or a pharmaceutically acceptable salt thereof, wherein $R^5$ is chloro.

39. The compound of any one clauses 34 to 36, or a pharmaceutically acceptable salt thereof, wherein $R^5$ is bromo.

40. The compound of any one clauses 34 to 36, or a pharmaceutically acceptable salt thereof, wherein $R^5$ is —$OC_1$-$C_6$ alkyl.

41. The compound of clause 40, wherein $R^5$ is methoxy, ethoxy, iso-propoxy, or n-propoxy.

42. The compound of any one clauses 34 to 36, or a pharmaceutically acceptable salt thereof, wherein $R^5$ is —OH.

43. The compound of any one clauses 34 to 36, or a pharmaceutically acceptable salt thereof, wherein $R^5$ is —CN.

44. The compound of any one clauses 34 to 36, or a pharmaceutically acceptable salt thereof, wherein $R^5$ is —$CF_3$.

45. The compound of any one clauses 34 to 36, or a pharmaceutically acceptable salt thereof, wherein $R^5$ is 5- to 7-membered heteroaryl; wherein each hydrogen atom in 5- to 7-membered heteroaryl is independently optionally substituted by fluoro, chloro, bromo, —OH, —CN, —$OC_1$-$C_6$ alkyl, —$NH_2$, —NH($C_1$-$C_6$ alkyl), —N($C_1$-$C_6$ alkyl)$_2$, —$CO_2$H, —C(O)$OC_1$-$C_6$ alkyl, —C(O)$NH_2$, —C(O)NH($C_1$-$C_6$ alkyl) and —C(O)N($C_1$-$C_6$ alkyl)$_2$.

46. The compound of clause 45, or a pharmaceutically acceptable salt thereof, wherein 5- to 7-membered heteroaryl is pyrrolyl, furanyl, thiophenyl, imidazolyl, pyrazolyl, pyridinyl, pyrimidinyl, quinolinyl, isoquinolinyl, purinyl, tetrazolyl, triazinyl or pyrazinyl, optionally substituted with one or more substituents selected from the group consisting of fluoro, chloro, bromo, —OH, —CN, —$OC_1$-$C_6$ alkyl, —$NH_2$, —NH($C_1$-$C_6$ alkyl), —N($C_1$-$C_6$ alkyl)$_2$, —$CO_2$H, —C(O)$OC_1$-$C_6$ alkyl, —C(O)$NH_2$, —C(O)NH($C_1$-$C_6$ alkyl) and —C(O)N($C_1$-$C_6$ alkyl)$_2$.

47. The compound of clause 45, or a pharmaceutically acceptable salt thereof, wherein 5- to 7-membered heteroaryl is pyrazolyl substituted with one or more substituents selected from the group consisting of fluoro, chloro, bromo, —OH, —CN, —$OC_1$-$C_6$ alkyl, —$NH_2$, —NH($C_1$-$C_6$ alkyl), —N($C_1$-$C_6$ alkyl)$_2$, —$CO_2$H, —C(O)$OC_1$-$C_6$ alkyl, —C(O)$NH_2$, —C(O)NH($C_1$-$C_6$ alkyl) and —C(O)N($C_1$-$C_6$ alkyl)$_2$.

48. The compound of clause 45, or a pharmaceutically acceptable salt thereof, wherein 5- to 7-membered heteroaryl is pyridinyl substituted with one or more substituents selected from the group consisting of fluoro, chloro, bromo, —OH, —CN, —$OC_1$-$C_6$ alkyl, —$NH_2$, —NH($C_1$-$C_6$ alkyl), —N($C_1$-$C_6$ alkyl)$_2$, —$CO_2$H, —C(O)$OC_1$-$C_6$ alkyl, —C(O)$NH_2$, —C(O)NH($C_1$-$C_6$ alkyl) and —C(O)N($C_1$-$C_6$ alkyl)$_2$.

49. The compound of clause 45, or a pharmaceutically acceptable salt thereof, wherein 5- to 7-membered heteroaryl is

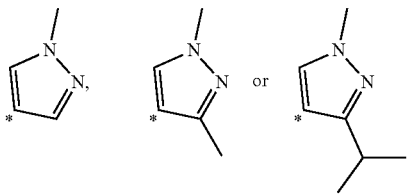

50. The compound of any one clauses 34 to 36, or a pharmaceutically acceptable salt thereof, wherein $R^5$ is $C_6$-$C_{10}$ aryl, wherein each hydrogen atom in $C_6$-$C_{10}$ aryl is independently optionally substituted by fluoro, chloro, bromo, —OH, —CN, —$OC_1$-$C_6$ alkyl, —$NH_2$, —NH($C_1$-$C_6$ alkyl), —N($C_1$-$C_6$ alkyl)$_2$, —$CO_2$H, —C(O)$OC_1$-$C_6$ alkyl, —C(O)$NH_2$, —C(O)NH($C_1$-$C_6$ alkyl) and —C(O)N($C_1$-$C_6$ alkyl)$_2$.

51. The compound of any one of the preceding clauses, or a pharmaceutically acceptable salt thereof, wherein $R^{10}$ is H or $C_1$-$C_6$ alkyl.

52. The compound of any one of the preceding clauses, or a pharmaceutically acceptable salt thereof, wherein $R^{10}$ is H.

53. The compound of any one of clauses 1 to 51, or a pharmaceutically acceptable salt thereof, wherein $R^{10}$ is $C_1$-$C_6$ alkyl.

54. The compound of clause 53, or a pharmaceutically acceptable salt thereof, wherein $R^{10}$ is methyl, ethyl or isopropyl.

55. The compound of any one of the preceding clauses, or a pharmaceutically acceptable salt thereof, wherein $R^2$ is H or $C_1$-$C_6$ alkyl; wherein each hydrogen atom in $C_1$-$C_6$ alkyl is independently optionally substituted by deuterium, halogen, —OH, —CN, —$OC_1$-$C_6$ alkyl, —$NH_2$, —NH($C_1$-$C_6$ alkyl), —N($C_1$-$C_6$ alkyl)$_2$, —NHC(O)$C_1$-$C_6$ alkyl, —N($C_1$-$C_6$ alkyl)C(O)$C_1$-$C_6$ alkyl, —NHC(O)$NH_2$, —NHC(O)NH$C_1$-$C_6$ alkyl, —N($C_1$-$C_6$ alkyl)C(O)$NH_2$, —N($C_1$-$C_6$ alkyl)C(O)NH$C_1$-$C_6$ alkyl, —NHC(O)N($C_1$-$C_6$ alkyl)$_2$, —N($C_1$-$C_6$ alkyl)C(O)N($C_1$-$C_6$ alkyl)$_2$, —NHC(O)$OC_1$-$C_6$ alkyl, —N($C_1$-$C_6$ alkyl)C(O)$OC_1$-$C_6$ alkyl, —NHS(O)($C_1$-$C_6$ alkyl), —NHS(O)$_2$($C_1$-$C_6$ alkyl), —N($C_1$-$C_6$ alkyl)S(O)($C_1$-$C_6$ alkyl), —N($C_1$-$C_6$ alkyl)S(O)$_2$($C_1$-$C_6$ alkyl), —NHS(O)$NH_2$, —NHS(O)$_2$$NH_2$, —N($C_1$-$C_6$ alkyl)S(O)$NH_2$, —N($C_1$-$C_6$ alkyl)S(O)$_2$$NH_2$, —NHS(O)NH($C_1$-$C_6$ alkyl), —NHS(O)$_2$NH($C_1$-$C_6$ alkyl), —NHS(O)N($C_1$-$C_6$ alkyl)$_2$, —NHS(O)$_2$N($C_1$-$C_6$ alkyl)$_2$, —N($C_1$-$C_6$ alkyl)S(O)NH($C_1$-$C_6$ alkyl), —N($C_1$-$C_6$ alkyl)S(O)$_2$NH($C_1$-$C_6$ alkyl), —N($C_1$-$C_6$ alkyl)S(O)N($C_1$-$C_6$ alkyl)$_2$, —N($C_1$-$C_6$ alkyl)S(O)$_2$N($C_1$-$C_6$ alkyl)$_2$, —$CO_2$H, —C(O)$OC_1$-$C_6$ alkyl, —C(O)$NH_2$, —C(O)NH($C_1$-$C_6$ alkyl), —C(O)N($C_1$-$C_6$ alkyl)$_2$, —$SC_1$-$C_6$ alkyl, —S(O)$C_1$-$C_6$ alkyl, —S(O)$_2$$C_1$-$C_6$ alkyl, —S(O)NH($C_1$-$C_6$ alkyl), —S(O)$_2$NH($C_1$-$C_6$ alkyl), —S(O)N($C_1$-$C_6$ alkyl)$_2$, —S(O)$_2$N($C_1$-$C_6$ alkyl)$_2$, —P($C_1$-$C_6$ alkyl)$_2$, —P(O)($C_1$-$C_6$ alkyl)$_2$, $C_3$-$C_6$ cycloalkyl, or 3- to 7-membered heterocycloalkyl.

56. The compound of any one of the preceding clauses, or a pharmaceutically acceptable salt thereof, wherein $R^2$ is $C_1$-$C_6$ alkyl, wherein one hydrogen atom in $C_1$-$C_6$ alkyl substituted by —OH.

57. The compound of any one of the preceding clauses, or a pharmaceutically acceptable salt thereof, wherein $R^2$ is —$CH_2$OH.

58. The compound of any one of the preceding clauses, or a pharmaceutically acceptable salt thereof, wherein n is 1.

59. The compound of any one of the preceding clauses, or a pharmaceutically acceptable salt thereof, wherein n is 2.

60. The compound of any one of the preceding clauses, or a pharmaceutically acceptable salt thereof, wherein each $R^3$ is H.

61. The compound of any one of the preceding clauses, or a pharmaceutically acceptable salt thereof, wherein $R^4$ is H.

62. The compound of any one of the preceding clauses, or a pharmaceutically acceptable salt thereof, wherein $R^6$ is selected from the group consisting of fluoro, chloro, bromo, $C_1$-$C_6$ alkyl, —OH, —CN, —O$C_1$-$C_6$ alkyl, —NH$C_1$-$C_6$ alkyl, —N($C_1$-$C_6$ alkyl)$_2$, 5- to 7-membered heteroaryl, $C_6$-$C_{10}$ aryl, and —CF$_3$; wherein each hydrogen atom in $C_1$-$C_6$ alkyl, 5- to 7-membered heteroaryl and $C_6$-$C_{10}$ aryl is independently optionally substituted by halogen, —OH, —CN, —O$C_1$-$C_6$ alkyl, —NH$_2$, —NH($C_1$-$C_6$ alkyl), —N($C_1$-$C_6$ alkyl)$_2$, —CO$_2$H, —C(O)O$C_1$-$C_6$ alkyl, —C(O)NH$_2$, —C(O)NH($C_1$-$C_6$ alkyl) and —C(O)N($C_1$-$C_6$ alkyl)$_2$.

63. The compound of any one of the preceding clauses, or a pharmaceutically acceptable salt thereof, wherein $R^6$ is fluoro.

64. The compound of clause 1, selected from the group consisting of

-continued

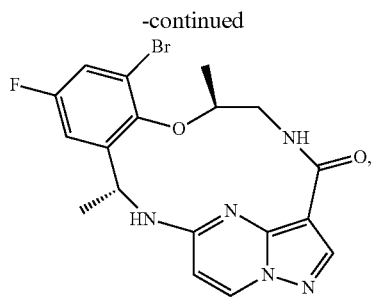

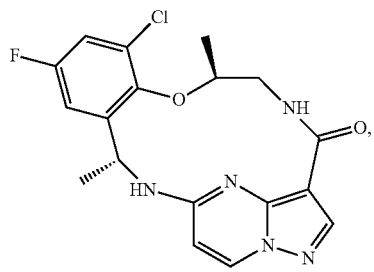

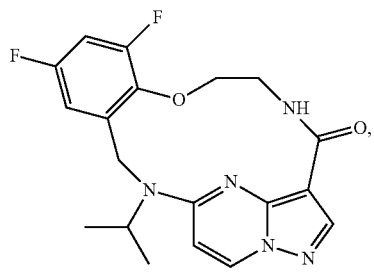

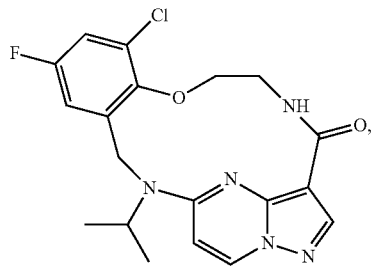

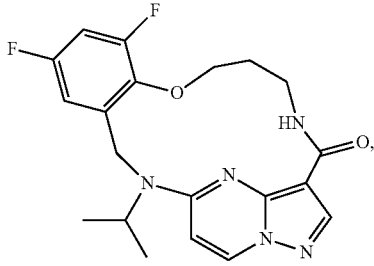

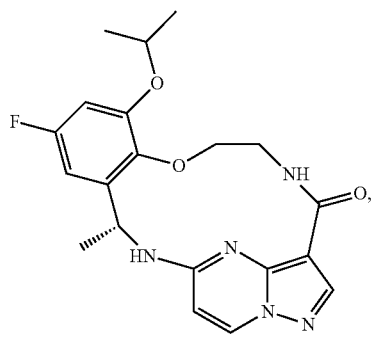

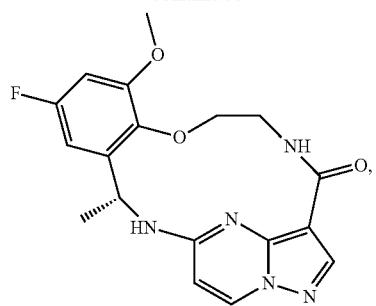
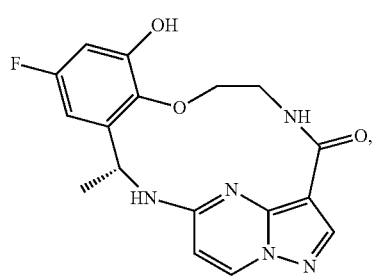
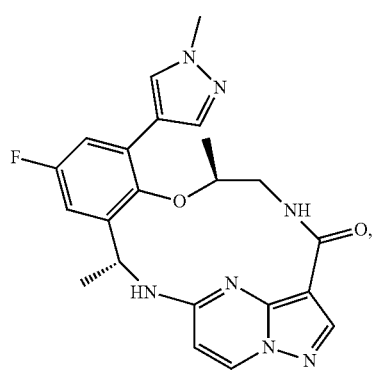
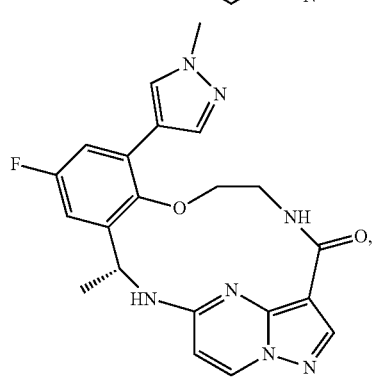
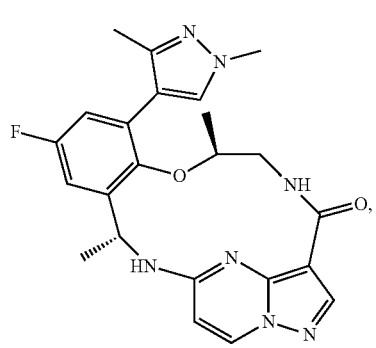
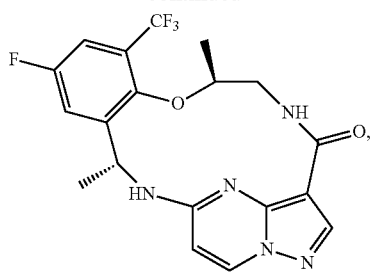
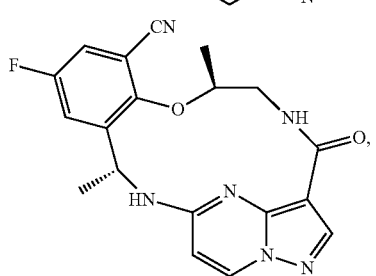
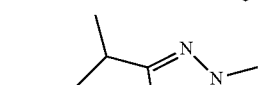
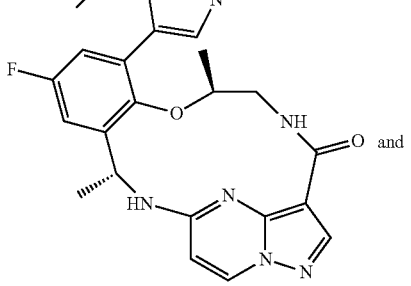
or a pharmaceutically acceptable salt thereof.
65. The compound of clause 1, selected from the group consisting of
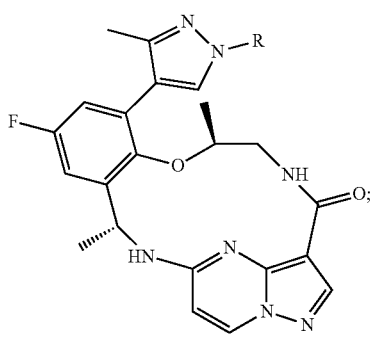

-continued

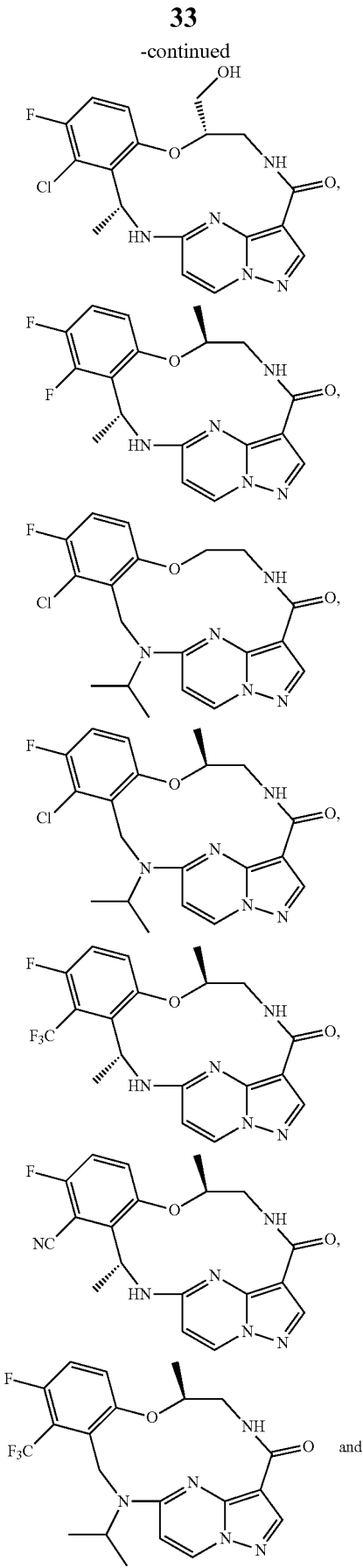

-continued

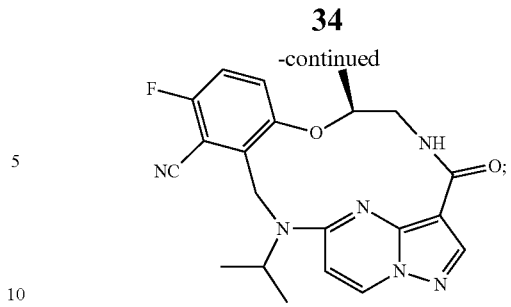

or a pharmaceutically acceptable salt thereof.

66. A pharmaceutical composition comprising a compound of any one of the preceding clauses, or a pharmaceutically acceptable salt thereof, and optionally at least one diluent, carrier or excipient.

67. A method of treating cancer, pain, neurological diseases, autoimmune diseases, or inflammation comprising administering to a subject in need of such treatment an effective amount of at least one compound of any one of clauses 1 to 65, or a pharmaceutically acceptable salt thereof.

68. Use of a compound of any one of clauses 1 to 65, or a pharmaceutically acceptable salt thereof, in the preparation of a medicament for the treatment of cancer, pain, neurological diseases, autoimmune diseases, or inflammation.

69. Use of a compound of any one of clauses 1 to 65, or a pharmaceutically acceptable salt thereof, for treating cancer, pain, neurological diseases, autoimmune diseases, or inflammation.

70. A method of inhibiting a non-receptor tyrosine kinases selected from the group consisting of JAK2 and BTK, comprising contacting a cell comprising one or more of such kinases with an effective amount of at least one compound of any one of clauses 1 to 65, or a pharmaceutically acceptable salt thereof, and/or with at least one pharmaceutical composition of the disclosure, wherein the contacting is in vitro, ex vivo, or in vivo.

71. A compound of any one of clauses 1 to 65 for use in treating cancer in a patient.

72. A compound of any one of clauses 1 to 65 for use in treating inflammation in a patient.

73. A compound of any one of clauses 1 to 65 for use in treating an autoimmune disease in a patient.

74. The method, use or compound of any one of clauses 67 to 71, wherein the cancer is mediated by BTK or JAK2.

75. The method, use or compound of any one of clauses 67 to 73, wherein the cancer is mediated by a genetically altered BTK or genetically altered JAK2.

76. The method, use or compound of clause 75, wherein the genetically altered BTK comprises at least one resistance mutation.

77. The method, use or compound of clause 76, wherein the at least one resistance mutation is C481S.

78. The method, use or compound of clause 75, wherein the cancer is mediated by a fusion protein comprising a fragment of a protein encoded by an JAK2 gene and a fragment of a protein encoded by a TEL or PCM1 gene.

79. The method of clause 75, wherein the genetically altered JAK2 is a TEL-JAK2 fusion protein.

80 The method of clause 75, wherein the genetically altered JAK2 is a PCM1-JAK2 fusion protein.

81. The method of clause 75, wherein the genetically altered JAK2 comprises a V617F point mutation.

82. The method, use or compound of any one of clauses 67 to 70 or 73, wherein the autoimmune disease is rheumatoid arthritis or systemic lupus erythematosus.

83. The method, use or compound of any one of clauses 67 to 71, wherein the cancer is selected from the group consisting of NSCLC, triple negative breast cancer, leukemia, myeloproliferative neoplasms, chronic lymphocytic leukemia, mantle cell leukemia and pancreas adenocarcinoma.

DETAILED DESCRIPTION

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw Ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, and $C_1$-$C_4$. Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments, alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic groups of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, including an all-carbon 5-member/6-member or 6-member/6-member fused bicyclic ring, or a multicyclic fused ring (a "fused" ring system means that each ring in the system shares an adjacent pair of carbon atoms with each other ring in the system) group, where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_9$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like. Illustrative examples of cycloalkyl groups shown in graphical representations include the following entities, in the form of properly bonded moieties:

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1,2,3,4-tetrahydropyridinyl, and the like. Illustrative examples of heterocycloalkyl groups shown in graphical representations include the following entities, in the form of properly bonded moieties:

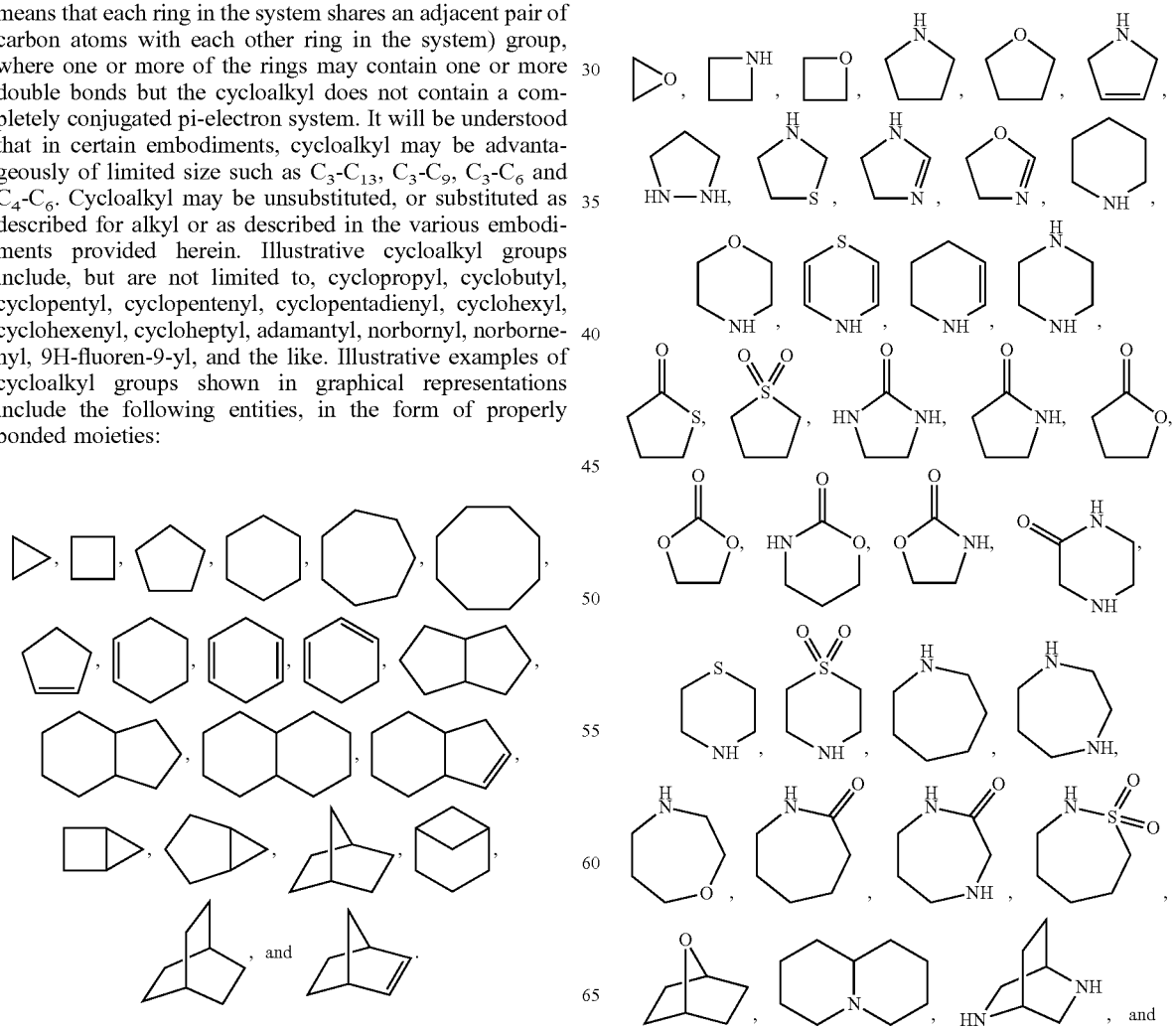

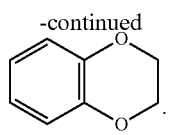

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

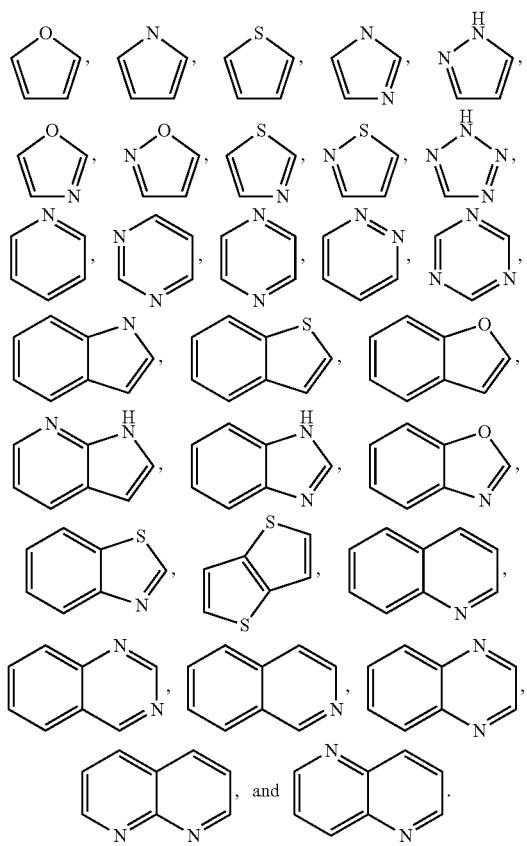

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "cyano" refers to a —CN group.

The term "oxo" represents a carbonyl oxygen. For example, a cyclopentyl substituted with oxo is cyclopentanone.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula I, Ia, Ib or Ic that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The disclosure also relates to pharmaceutically acceptable prodrugs of the compounds of Formula I, Ia, Ib or Ic, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I, Ia, Ib or Ic). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present disclosure also relates to pharmaceutically active metabolites of compounds of Formula I, Ia, Ib or Ic, and uses of such metabolites in the methods of the disclosure. A "pharmaceutically active metabolite" means a pharmacologically active product of metabolism in the body of a compound of Formula I, Ia, Ib or Ic or salt thereof. Prodrugs and active metabolites of a compound may be determined using routine techniques known or available in the art. See, e.g., Bertolini et al., J. Med. Chem. 1997, 40, 2011-2016; Shan et al., J. Pharm. Sci. 1997, 86 (7), 765-767; Bagshawe, Drug Dev. Res. 1995, 34, 220-230; Bodor, Adv. Drug Res. 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol " ⌇ " include both stereoisomers for the carbon atom to which the symbol " ⌇ " is attached, specifically both the bonds "▬" and "⫶⫶⫶⫶⫶" are encompassed by the meaning of " ⌇ ". For example, in some exemplary embodiments, certain compounds provided herein can be described by the formula

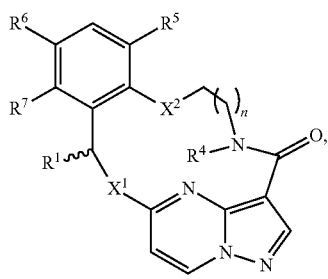

which formula will be understood to encompass compounds having both stereochemical configurations at the relevant carbon atom, specifically in this example

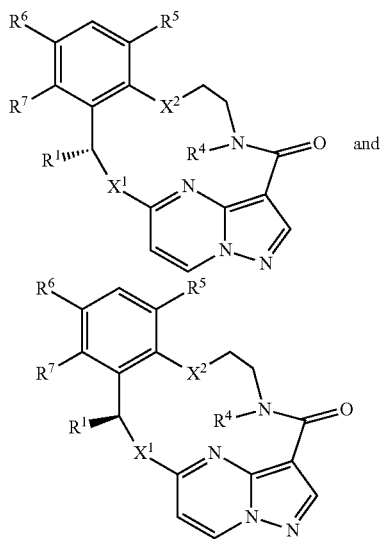

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

Representative Embodiments

In some embodiments, $X^1$ is $-N(R^{10})-$. In some embodiments, $X^2$ is $-O-$. In some embodiments, $X^1$ is $-N(R^{10})-$, and $X^2$ is $-O-$.

In some embodiments, $R^1$ is $C_1$-$C_6$ alkyl, $C_2$-$C_6$ alkenyl, $C_2$-$C_6$ alkynyl, $C_3$-$C_6$ cycloalkyl, $C_6$-$C_{10}$ aryl, $-C(O)OR^7$ or $-C(O)NR^7R^8$; wherein each hydrogen atom in $C_1$-$C_6$ alkyl, $C_2$-$C_6$ alkenyl, $C_2$-$C_6$ alkynyl, $C_3$-$C_6$ cycloalkyl and $C_6$-$C_{10}$ aryl is independently optionally substituted by deuterium, halogen, $-OH$, $-CN$, $-OC_1$-$C_6$ alkyl, $-NH_2$, $-NH(C_1$-$C_6$ alkyl), $-N(C_1$-$C_6$ alkyl)$_2$, $-NHC(O)C_1$-$C_6$ alkyl, $-N(C_1$-$C_6$ alkyl)C(O)C_1$-$C_6$ alkyl, $-NHC(O)NH_2$, $-NHC(O)NHC_1$-$C_6$ alkyl, $-N(C_1$-$C_6$ alkyl)C(O)NH_2$, $-N(C_1$-$C_6$ alkyl)C(O)NHC_1$-$C_6$ alkyl, $-NHC(O)N(C_1$-$C_6$ alkyl)$_2$, $-N(C_1$-$C_6$ alkyl)C(O)N(C_1$-$C_6$ alkyl)$_2$, $-NHC(O)OC_1$-$C_6$ alkyl, $-N(C_1$-$C_6$ alkyl)C(O)OC_1$-$C_6$ alkyl, $-NHS(O)(C_1$-$C_6$ alkyl), $-NHS(O)_2(C_1$-$C_6$ alkyl), $-N(C_1$-$C_6$ alkyl)S(O)(C_1$-$C_6$ alkyl), $-N(C_1$-$C_6$ alkyl)S(O)_2(C_1$-$C_6$ alkyl), $-NHS(O)NH_2$, $NHS(O)_2NH_2$, $-N(C_1$-$C_6$ alkyl)S(O)NH_2$, $-N(C_1$-$C_6$ alkyl)S(O)_2NH_2$, $-NHS(O)NH(C_1$-$C_6$ alkyl), $-NHS(O)_2NH(C_1$-$C_6$ alkyl), $-NHS(O)N(C_1$-$C_6$ alkyl)$_2$, $-NHS(O)_2N(C_1$-$C_6$ alkyl)$_2$, $-N(C_1$-$C_6$ alkyl)S(O)NH(C_1$-$C_6$ alkyl), $-N(C_1$-$C_6$ alkyl)S(O)_2NH(C_1$-$C_6$ alkyl), $-N(C_1$-$C_6$ alkyl)S(O)N(C_1$-$C_6$ alkyl)$_2$, $-N(C_1$-$C_6$ alkyl)S(O)_2N(C_1$-$C_6$ alkyl)$_2$, $-CO_2H$, $-C(O)OC_1$-$C_6$ alkyl, $-C(O)NH_2$, $-C(O)NH(C_1$-$C_6$ alkyl), $-C(O)N(C_1$-$C_6$ alkyl)$_2$, $-SC_1$-$C_6$ alkyl, $-S(O)C_1$-$C_6$ alkyl, $-S(O)_2C_1$-$C_6$ alkyl, $-S(O)NH(C_1$-$C_6$ alkyl), $-S(O)_2NH(C_1$-$C_6$ alkyl), $-S(O)N(C_1$-$C_6$ alkyl)$_2$, $-S(O)_2N(C_1$-$C_6$ alkyl)$_2$, $-P(C_1$-$C_6$ alkyl)$_2$, $-P(O)(C_1$-$C_6$ alkyl)$_2$, $C_3$-$C_6$ cycloalkyl or 3- to 7-membered heterocycloalkyl.

In some embodiments, $R^1$ is $C_1$-$C_6$ alkyl, wherein each hydrogen atom is independently optionally substituted by deuterium, halogen, $-OH$, $-CN$, $-OC_1$-$C_6$ alkyl, $-NH_2$, $-NH(C_1$-$C_6$ alkyl), $-N(C_1$-$C_6$ alkyl)$_2$, $-NHC(O)C_1$-$C_6$ alkyl, $-N(C_1$-$C_6$ alkyl)C(O)C_1$-$C_6$ alkyl, $-NHC(O)NH_2$, $-NHC(O)NHC_1$-$C_6$ alkyl, $-N(C_1$-$C_6$ alkyl)C(O)NH_2$, $-N(C_1$-$C_6$ alkyl)C(O)NHC_1$-$C_6$ alkyl, $-NHC(O)N(C_1$-$C_6$ alkyl)$_2$, $-N(C_1$-$C_6$ alkyl)C(O)N(C_1$-$C_6$ alkyl)$_2$, $-NHC(O)OC_1$-$C_6$ alkyl, $-N(C_1$-$C_6$ alkyl)C(O)OC_1$-$C_6$ alkyl, $-NHS(O)(C_1$-$C_6$ alkyl), $-NHS(O)_2(C_1$-$C_6$ alkyl), $-N(C_1$-$C_6$ alkyl)S(O)(C_1$-$C_6$ alkyl), $-N(C_1$-$C_6$ alkyl)S(O)_2(C_1$-$C_6$ alkyl), $-NHS(O)NH_2$, $-NHS(O)_2NH_2$, $-N(C_1$-$C_6$ alkyl)S(O)NH_2$, $-N(C_1$-$C_6$ alkyl)S(O)_2NH_2$, $-NHS(O)NH(C_1$-$C_6$ alkyl), $-NHS(O)_2NH(C_1$-$C_6$ alkyl), $-NHS(O)N(C_1$-$C_6$ alkyl)$_2$, $-NHS(O)_2N(C_1$-$C_6$ alkyl)$_2$, $-N(C_1$-$C_6$ alkyl)S(O)NH(C_1$-$C_6$ alkyl), $-N(C_1$-$C_6$ alkyl)S(O)_2NH(C_1$-$C_6$ alkyl), $-N(C_1$-$C_6$ alkyl)S(O)N(C_1$-$C_6$ alkyl)$_2$, $-N(C_1$-$C_6$ alkyl)S(O)_2N(C_1$-$C_6$ alkyl)$_2$, $-CO_2H$, $-C(O)OC_1$-$C_6$ alkyl, $-C(O)NH_2$, $-C(O)NH(C_1$-$C_6$ alkyl), $-C(O)N(C_1$-$C_6$ alkyl)$_2$, $-SC_1$-$C_6$ alkyl, $-S(O)C_1$-$C_6$ alkyl, $-S(O)_2C_1$-$C_6$ alkyl, $-S(O)NH(C_1$-$C_6$ alkyl), $-S(O)_2NH(C_1$-$C_6$ alkyl), $-S(O)N(C_1$-$C_6$ alkyl)$_2$, $-S(O)_2N(C_1$-$C_6$ alkyl)$_2$, $-P(C_1$-$C_6$ alkyl)$_2$, $-P(O)(C_1$-$C_6$ alkyl)$_2$, $C_3$-$C_6$ cycloalkyl, or 3- to 7-membered heterocycloalkyl.

In some embodiments, $R^1$ is methyl, ethyl, isopropyl, 2-hydroxy-2-propryl, 2-hydroxyethyl or 2-fluoroethyl. In some embodiments, $R^1$ is methyl. In some embodiments, $R^1$ is ethyl. In some embodiments, $R^1$ is isopropyl. In some embodiments, $R^1$ is 2-hydroxy-2-propyl. In some embodiments, $R^1$ is 2-hydroxyethyl. In some embodiments, $R^1$ is 2-fluoroethyl. In some embodiments, $R^1$ is $D_3C$—. In some embodiments, $R^1$ is —C(O)NH$_2$, —C(O)NH(C$_1$-C$_6$ alkyl) or —C(O)N(C$_1$-C$_6$ alkyl). In some embodiments, $R^1$ is —C(O)NHCH$_3$. In some embodiments, $R^1$ is —C(O)N(CH$_3$)$_2$. In some embodiments, $R^1$ is cyanomethyl.

In some embodiments, $R^2$ is C$_1$-C$_6$ alkyl, wherein each hydrogen atom in C$_1$-C$_6$ alkyl is independently optionally substituted with one or more moieties selected from group consisting of —F, —OH, —OC$_1$-C$_6$ alkyl, —NH$_2$, —NH(C$_1$-C$_6$ alkyl), and —N(C$_1$-C$_6$ alkyl)$_2$. In some embodiments, $R^2$ is C$_1$-C$_6$ alkyl substituted with an —OH. In some embodiments, $R^2$ is —CH$_2$OH. In some embodiments, $R^2$ is C$_1$-C$_6$ alkyl or —C(O)NR$^7$R$^8$, wherein each hydrogen atom in C$_1$-C$_6$ alkyl is independently optionally substituted with one or more moieties selected from group consisting of —F, —OH, —OC$_1$-C$_6$ alkyl, —NH$_2$, —NH(C$_1$-C$_6$ alkyl), and —N(C$_1$-C$_6$ alkyl)$_2$, and $R^3$ is H. In some embodiments, $R^2$ is C$_1$-C$_6$ alkyl substituted with an —OH, and $R^3$ is H. In some embodiments, $R^2$ is —CH$_2$OH, and $R^3$ is H.

In some embodiments, $R^3$ is C$_1$-C$_6$ alkyl or —C(O)NR$^7$R$^8$, wherein each hydrogen atom in C$_1$-C$_6$ alkyl is independently optionally substituted with one or more moieties selected from group consisting of —F, —OH, —OC$_1$-C$_6$ alkyl, —NH$_2$, —NH(C$_1$-C$_6$ alkyl), and —N(C$_1$-C$_6$ alkyl)$_2$. In some embodiments, $R^3$ is C$_1$-C$_6$ alkyl or —C(O)NR$^7$R$^8$, wherein each hydrogen atom in C$_1$-C$_6$ alkyl is independently optionally substituted with one or more moieties selected from group consisting of —F, —OH, —OC$_1$-C$_6$ alkyl, —NH$_2$, —NH(C$_1$-C$_6$ alkyl), and —N(C$_1$-C$_6$ alkyl)$_2$, and $R^2$ is H.

In some embodiments, $R^4$ is H.

In some embodiments, $R^7$ is selected from the group consisting of fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, 5- to 7-membered heteroaryl, C$_6$-C$_{10}$ aryl, and —CF$_3$; wherein each hydrogen atom in C$_1$-C$_6$ alkyl, 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$.

In some embodiments, $R^7$ is selected from the group consisting of fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, 5- to 7-membered heteroaryl, C$_6$-C$_{10}$ aryl, and —CF$_3$; wherein each hydrogen atom in C$_1$-C$_6$ alkyl, 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$, and $R^5$ is H.

In some embodiments, $R^7$ is selected from the group consisting of fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, 5- to 7-membered heteroaryl, C$_6$-C$_{10}$ aryl, and —CF$_3$; wherein each hydrogen atom in C$_1$-C$_6$ alkyl, 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$, $R^5$ is H and $R^6$ is F.

In some embodiments, $R^7$ is selected from the group consisting of fluoro, chloro, bromo, C$_1$-C$_6$ alkyl, —OH, —CN, —OC$_1$-C$_6$ alkyl, 5- to 7-membered heteroaryl, and —CF$_3$. In some embodiments, $R^7$ is selected from the group consisting of fluoro, chloro, bromo, C$_1$-C$_6$ alkyl, —OH, —CN, —OC$_1$-C$_6$ alkyl, 5- to 7-membered heteroaryl, and —CF$_3$, and $R^5$ is H. In some embodiments, $R^7$ is selected from the group consisting of fluoro, chloro, bromo, C$_1$-C$_6$ alkyl, —OH, —CN, —OC$_1$-C$_6$ alkyl, 5- to 7-membered heteroaryl, and —CF$_3$, $R^5$ is H, $R^6$ is F.

In some embodiments, $R^5$ is selected from the group consisting of fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, 5- to 7-membered heteroaryl, C$_6$-C$_{10}$ aryl, and —CF$_3$; wherein each hydrogen atom in C$_1$-C$_6$ alkyl, —OC$_1$-C$_6$ alkyl, —NHC$_1$-C$_6$ alkyl, —N(C$_1$-C$_6$ alkyl)$_2$, 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, C$_3$-C$_7$ cycloalkyl, 3- to 7-membered heterocycloalkyl, C$_6$-C$_{10}$ aryl, 5- to 7-membered heteroaryl, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$.

In some embodiments, $R^5$ is selected from the group consisting of fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, 5- to 7-membered heteroaryl, C$_6$-C$_{10}$ aryl, and —CF$_3$; wherein each hydrogen atom in C$_1$-C$_6$ alkyl, —OC$_1$-C$_6$ alkyl, —NHC$_1$-C$_6$ alkyl, —N(C$_1$-C$_6$ alkyl)$_2$, 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, C$_3$-C$_7$ cycloalkyl, 3- to 7-membered heterocycloalkyl, C$_6$-C$_{10}$ aryl, 5- to 7-membered heteroaryl, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$, and $R^7$ is H.

In some embodiments, $R^5$ is selected from the group consisting of fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, 5- to 7-membered heteroaryl, C$_6$-C$_{10}$ aryl, and —CF$_3$; wherein each hydrogen atom in C$_1$-C$_6$ alkyl, —OC$_1$-C$_6$ alkyl, —NHC$_1$-C$_6$ alkyl, —N(C$_1$-C$_6$ alkyl)$_2$, 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, C$_3$-C$_7$ cycloalkyl, 3- to 7-membered heterocycloalkyl, C$_6$-C$_{10}$ aryl, 5- to 7-membered heteroaryl, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$, $R^6$ is F, and $R^7$ is H.

In some embodiments, $R^5$ is —OC$_1$-C$_6$ alkyl, wherein each hydrogen atom in —OC$_1$-C$_6$ alkyl, is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, C$_3$-C$_7$ cycloalkyl, 3- to 7-membered heterocycloalkyl, C$_6$-C$_{10}$ aryl, 5- to 7-membered heteroaryl, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$. In some embodiments, $R^5$ is —OC$_1$-C$_6$ alkyl substituted with a substituent selected from the group consisting of C$_3$-C$_7$ cycloalkyl, 3- to 7-membered heterocycloalkyl, C$_6$-C$_{10}$ aryl and 5- to 7-membered heteroaryl. In some embodiments, $R^5$ is —OC$_1$-C$_6$ alkyl substituted with phenyl, oxetane or azetidine. In some embodiments, $R^5$ is —O—(C$_3$-C$_6$ cycloalkyl). In some embodiments, $R^5$ is —O-cyclopropyl, —O-cyclobutyl or —O-cyclopentyl. In some embodiments, $R^5$ is —O-(3- to 7-membered heterocycloalkyl). In some embodiments, $R^5$ is —O-oxiranyl, —O-oxetanyl or —O-azetidinyl.

In other embodiments, the compound of Formula I, Ia, Ib or Ic is selected from the group consisting of (7S,13R)-9,11-difluoro-7,13-dimethyl-6,7,13,14-tetrahydro-1,15-ethenopyrazolo[4,3-f][1,4,8,10]benzoxatriazacyclotridecin-4(5H)-one, (7S,13R)-12-chloro-11-fluoro-7,13-dimethyl-6,7,13,14-tetrahydro-1,15-ethenopyrazolo[4,3-f][1,4,8,10]benzoxatriazacyclotridecin-4(5H)-one, (7S,13R)-9,11-difluoro-7-(hydroxymethyl)-13-methyl-6,7,13,14-tetrahydro-1,15-ethenopyrazolo[4,3-f][1,4,8,10]benzoxatriazacyclotridecin-4(5H)-one, (7S,13R)-12-chloro-11-fluoro-7-(hydroxymethyl)-13-methyl-6,7,13,14-tetrahydro-1,15-ethenopyrazolo[4,3-f][1,4,8,10]benzoxatriazacyclotridecin-4(5H)-one, (13R)-9-bromo-11-fluoro-13-methyl-6,7,13,14-tetrahydro-1,15-ethenopyrazolo[4,3-f][1,4,8,10]benzoxatriazacyclotridecin-4(5H)-one, (13R)-9-chloro-11-fluoro-13-methyl-6,7,13,14-tetrahydro-1,15-ethenopyrazolo[4,3-f][1,4,8,10]benzoxatriazacyclotridecin-4(5H)-one, (7S,13R)-9-bromo-11-fluoro-7,13-dimethyl-6,7,13,14-tetrahydro-1,15-ethenopyrazolo[4,3-f][1,4,8,10]benzoxatriazacyclotridecin-4(5H)-one, (7S,13R)-9-chloro-11-fluoro-7,13-dimethyl-6,7,13,14-tetrahydro-1,15-ethenopyrazolo[4,3-f][1,4,8,10]benzoxatriazacyclotridecin-4(5H)-one, 9,11-difluoro-14-(propan-2-yl)-6,7,13,14-tetrahydro-1,15-ethenopyrazolo[4,3-f][1,4,8,10]benzoxatriazacyclotridecin-4(5H)-one, 9-chloro-11-fluoro-14-(propan-2-yl)-6,7,13,14-tetrahydro-1,15-ethenopyrazolo[4,3-f][1,4,8,10]benzoxatriazacyclotridecin-4(5H)-one, (7S,13R)-11,12-difluoro-7,13-dimethyl-6,7,13,14-tetrahydro-1,15-ethenopyrazolo[4,3-f][1,4,8,10]benzoxatriazacyclotridecin-4(5H)-one, 10,12-difluoro-15-(propan-2-yl)-5,6,7,8,14,15-hexahydro-4H-1,16-ethenopyrazolo[4,3-g][1,5,9,11]benzoxatriazacyclotetradecin-4-one, 12-chloro-11-fluoro-14-(propan-2-yl)-6,7,13,14-tetrahydro-1,15-ethenopyrazolo[4,3-f][1,4,8,10]benzoxatriazacyclotridecin-4(5H)-one, (7S)-12-chloro-11-fluoro-7-methyl-14-(propan-2-yl)-6,7,13,14-tetrahydro-1,15-ethenopyrazolo[4,3-f][1,4,8,10]benzoxatriazacyclotridecin-4(5H)-one, (13R)-11-fluoro-13-methyl-9-[(propan-2-yl)oxy]-6,7,13,14-tetrahydro-1,15-ethenopyrazolo[4,3-f][1,4,8,10]benzoxatriazacyclotridecin-4(5H)-one, (13R)-11-fluoro-9-methoxy-13-methyl-6,7,13,14-tetrahydro-1,15-ethenopyrazolo[4,3-f][1,4,8,10]benzoxatriazacyclotridecin-4(5H)-one, (13R)-11-fluoro-9-hydroxy-13-methyl-6,7,13,14-tetrahydro-1,15-ethenopyrazolo[4,3-f][1,4,8,10]benzoxatriazacyclotridecin-4(5H)-one, (7S,13R)-11-fluoro-7,13-dimethyl-9-(1-methyl-1H-pyrazol-4-yl)-6,7,13,14-tetrahydro-1,15-ethenopyrazolo[4,3-f][1,4,8,10]benzoxatriazacyclotridecin-4(5H)-one, (13R)-11-fluoro-13-methyl-9-(1-methyl-1H-pyrazol-4-yl)-6,7,13,14-tetrahydro-1,15-ethenopyrazolo[4,3-f][1,4,8,10]benzoxatriazacyclotridecin-4(5H)-one and (7S,13R)-9-(1,3-dimethyl-1H-pyrazol-4-yl)-11-fluoro-7,13-dimethyl-6,7,13,14-tetrahydro-1,15-ethenopyrazolo[4,3-f][1,4,8,10]benzoxatriazacyclotridecin-4(5H)-one;

or a pharmaceutically acceptable salt thereof.

The following represent illustrative embodiments of compounds of the formula I, Ia, Ib, and Ic:

| Compound | Structure | Name |
|---|---|---|
| 1 | 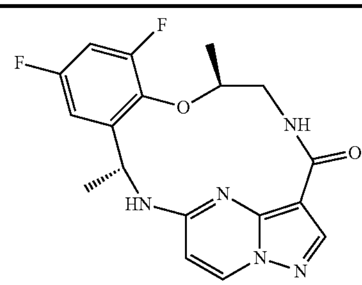 | (7S,13R)-9,11-difluoro-7,13-dimethyl-6,7,13,14-tetrahydro-1,15-ethenopyrazolo[4,3-f][1,4,8,10]benzoxatriazacyclotridecin-4(5H)-one |
| 2 | 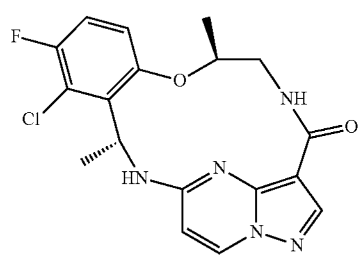 [SMILES: C[C@H]1CNC(=O)c2cnn3ccc(nc23)N[C@H](C)c2c(ccc(F)c2Cl)O1] | (7S,13R)-12-chloro-11-fluoro-7,13-dimethyl-6,7,13,14-tetrahydro-1,15-ethenopyrazolo[4,3-f][1,4,8,10]benzoxatriazacyclotridecin-4(5H)-one |
| 3 | 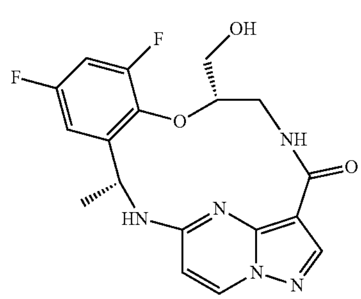 [SMILES: C[C@H]1Nc2ccn3ncc(c3n2)C(=O)NC[C@@H](CO)Oc2c(F)cc(F)cc21] | (7S,13R)-9,11-difluoro-7-(hydroxymethyl)-13-methyl-6,7,13,14-tetrahydro-1,15-ethenopyrazolo[4,3-f][1,4,8,10]benzoxatriazacyclotridecin-4(5H)-one |

-continued

| Compound | Structure | Name |
|---|---|---|
| 4 | 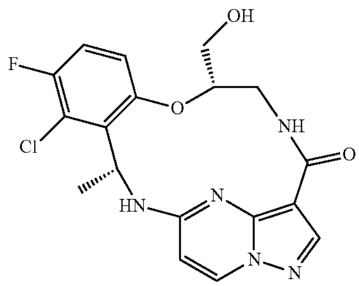 [SMILES: C[C@H]1Nc2ccn3ncc(c3n2)C(=O)NC[C@@H](CO)Oc2ccc(F)c(Cl)c21] | (7S,13R)-12-chloro-11-fluoro-7-(hydroxymethyl)-13-methyl-6,7,13,14-tetrahydro-1,15-ethenopyrazolo[4,3-f][1,4,8,10]benzoxatriazacyclotridecin-4(5H)-one |
| 5 | 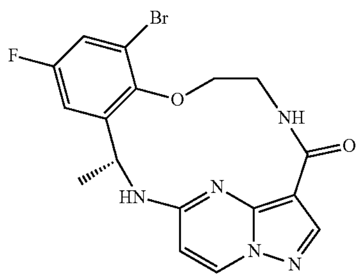 [SMILES: C[C@H]1Nc2ccn3ncc(c3n2)C(=O)NCCOc2c(Br)cc(F)cc21] | (13R)-9-bromo-11-fluoro-13-methyl-6,7,13,14-tetrahydro-1,15-ethenopyrazolo[4,3-f][1,4,8,10]benzoxatriazacyclotridecin-4(5H)-one |
| 6 | 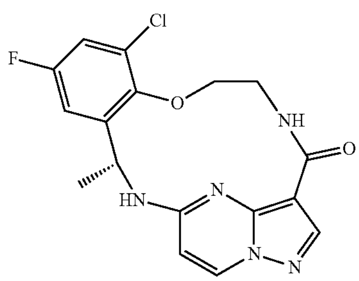 [SMILES: C[C@H]1Nc2ccn3ncc(c3n2)C(=O)NCCOc2c(Cl)cc(F)cc21] | (13R)-9-chloro-11-fluoro-13-methyl-6,7,13,14-tetrahydro-1,15-ethenopyrazolo[4,3-f][1,4,8,10]benzoxatriazacyclotridecin-4(5H)-one |
| 7 | 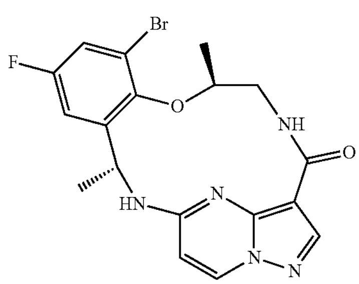 [SMILES: C[C@H]1CNC(=O)c2cnn3ccc(nc23)N[C@H](C)c2cc(F)cc(Br)c2O1] | (7S,13R)-9-bromo-11-fluoro-7,13-dimethyl-6,7,13,14-tetrahydro-1,15-ethenopyrazolo[4,3-f][1,4,8,10]benzoxatriazacyclotridecin-4(5H)-one |
| 8 | 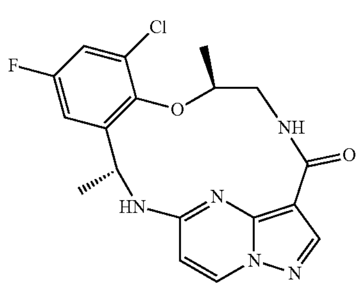 [SMILES: C[C@H]1CNC(=O)c2cnn3ccc(nc23)N[C@H](C)c2cc(F)cc(Cl)c2O1] | (7S,13R)-9-chloro-11-fluoro-7,13-dimethyl-6,7,13,14-tetrahydro-1,15-ethenopyrazolo[4,3-f][1,4,8,10]benzoxatriazacyclotridecin-4(5H)-one |

-continued

| Compound | Structure | Name |
|---|---|---|
| 9 | 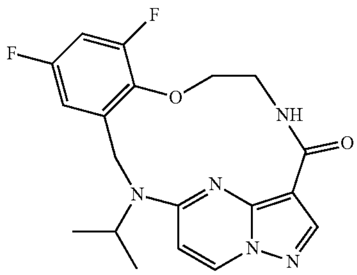 [SMILES: CC(C)N1Cc2cc(F)cc(F)c2OCCNC(=O)c2cnn3ccc1nc23] | 9,11-difluoro-14-(propan-2-yl)-6,7,13,14-tetrahydro-1,15-ethenopyrazolo[4,3-f′][1,4,8,10]benzoxatriazacyclotridecin-4(5H)-one |
| 10 | 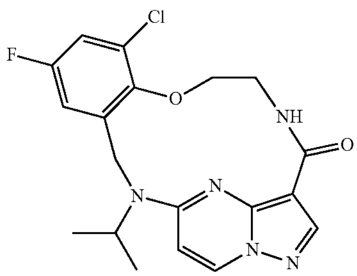 | 9-chloro-11-fluoro-14-(propan-2-yl)-6,7,13,14-tetrahydro-1,15-ethenopyrazolo[4,3-f′][1,4,8,10]benzoxatriazacyclotridecin-4(5H)-one |
| 11 | 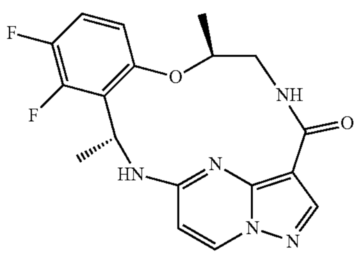 [SMILES: C[C@H]1CNC(=O)c2cnn3ccc(nc23)N[C@H](C)c2c(ccc(F)c2F)O1] | (7S,13R)-11,12-difluoro-7,13-dimethyl-6,7,13,14-tetrahydro-1,15-ethenopyrazolo[4,3-f′][1,4,8,10]benzoxatriazacyclotridecin-4(5H)-one |
| 12 | 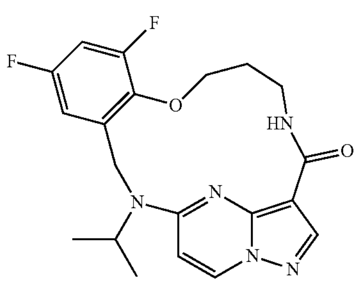 [SMILES: CC(C)N1Cc2cc(F)cc(F)c2OCCCNC(=O)c2cnn3ccc1nc23] | 10,12-difluoro-15-(propan-2-yl)-5,6,7,8,14,15-hexahydro-4H-1,16-ethenopyrazolo[4,3-g][1,5,9,11]benzoxatriazacyclotetradecin-4-one |
| 13 | 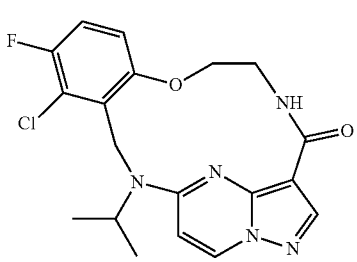 [SMILES: CC(C)N1Cc2c(ccc(F)c2Cl)OCCNC(=O)c2cnn3ccc1nc23] | 12-chloro-11-fluoro-14-(propan-2-yl)-6,7,13,14-tetrahydro-1,15-ethenopyrazolo[4,3-f′][1,4,8,10]benzoxatriazacyclotridecin-4(5H)-one |

| Compound | Structure | Name |
|---|---|---|
| 14 | 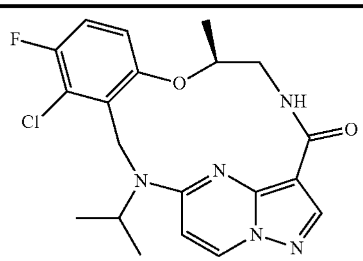 | (7S)-12-chloro-11-fluoro-7-methyl-14-(propan-2-yl)-6,7,13,14-tetrahydro-1,15-ethenopyrazolo[4,3-f][1,4,8,10]benzoxatriazacyclotridecin-4(5H)-one |
| 15 | 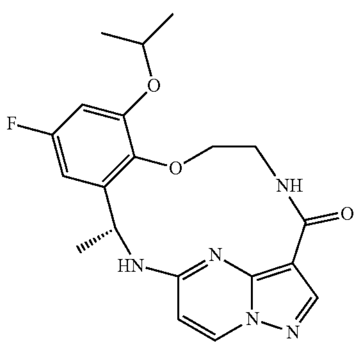 [SMILES: CC(C)Oc1cc(F)cc2c1OCCNC(=O)c1cnn3ccc(nc13)N[C@@H]2C] | (13R)-11-fluoro-13-methyl-9-[(propan-2-yl)oxy]-6,7,13,14-tetrahydro-1,15-ethenopyrazolo[4,3-f][1,4,8,10]benzoxatriazacyclotridecin-4(5H)-one |
| 16 | 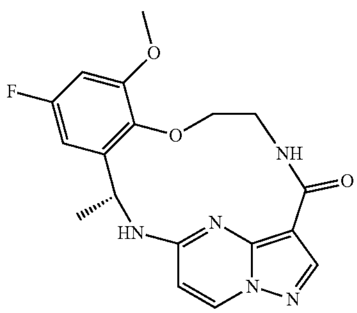 [SMILES: COc1cc(F)cc2c1OCCNC(=O)c1cnn3ccc(nc13)N[C@@H]2C] | (13R)-11-fluoro-9-methoxy-13-methyl-6,7,13,14-tetrahydro-1,15-ethenopyrazolo[4,3-f][1,4,8,10]benzoxatriazacyclotridecin-4(5H)-one |
| 17 | 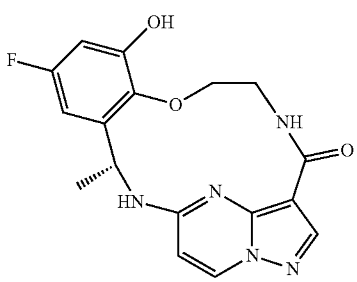 [SMILES: C[C@H]1Nc2ccn3ncc(c3n2)C(=O)NCCOc2c(O)cc(F)cc21] | (13R)-11-fluoro-9-hydroxy-13-methyl-6,7,13,14-tetrahydro-1,15-ethenopyrazolo[4,3-f][1,4,8,10]benzoxatriazacyclotridecin-4(5H)-one |
| 18 | 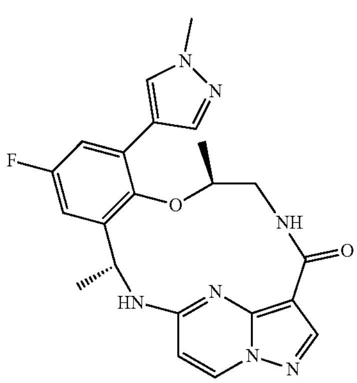 [SMILES: C[C@H]1CNC(=O)c2cnn3ccc(nc23)N[C@H](C)c2cc(F)cc(-c3cnn(C)c3)c2O1] | (7S,13R)-11-fluoro-7,13-dimethyl-9-(1-methyl-1H-pyrazol-4-yl)-6,7,13,14-tetrahydro-1,15-ethenopyrazolo[4,3-f][1,4,8,10]benzoxatriazacyclotridecin-4(5H)-one |

-continued

| Compound | Structure | Name |
|---|---|---|
| 19 | 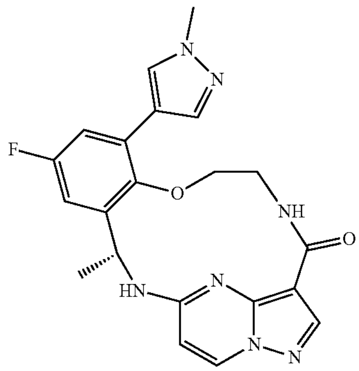 [SMILES: C[C@H]1Nc2ccn3ncc(c3n2)C(=O)NCCOc2c(-c3cnn(C)c3)cc(F)cc21] | (13R)-11-fluoro-13-methyl-9-(1-methyl-1H-pyrazol-4-yl)-6,7,13,14-tetrahydro-1,15-ethenopyrazolo[4,3-*f*][1,4,8,10]benzoxatriazacyclotridecin-4(5H)-one |
| 20 | 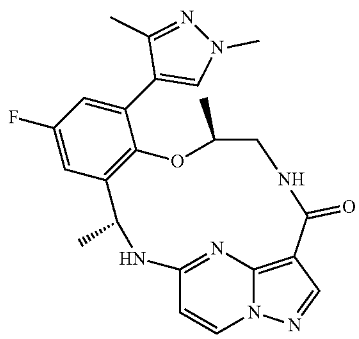 [SMILES: Cc1nn(C)cc1-c1cc(F)cc2c1O[C@@H](C)CNC(=O)c1cnn3ccc(nc13)N[C@@H]2C] | (7S,13R)-9-(1,3-dimethyl-1H-pyrazol-4-yl)-11-fluoro-7,13-dimethyl-6,7,13,14-tetrahydro-1,15-ethenopyrazolo[4,3-*f*][1,4,8,10]benzoxatriazacyclotridecin-4(5H)-one |

Those skilled in the art will recognize that the species listed or illustrated herein are not exhaustive, and that additional species within the scope of these defined terms may also be selected.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

Exemplary diseases include cancer, pain, neurological diseases, autoimmune diseases, and inflammation. Cancer includes, for example, NSCLC, triple negative breast cancer, leukemia, myeloproliferative neoplasms, chronic lymphocytic leukemia, mantle cell leukemia and pancreas adenocarcinoma lung cancer, colon cancer, breast cancer, prostate cancer, hepatocellular carcinoma, renal cell carcinoma, gastric and esophago-gastric cancers, glioblastoma, head and neck cancers, inflammatory myofibroblastic tumors, and anaplastic large cell lymphoma. Pain includes, for example, pain from any source or etiology, including cancer pain, pain from chemotherapeutic treatment, nerve pain, pain from injury, or other sources. Autoimmune diseases include, for example, rheumatoid arthritis, systemic lupus erythematosus, Sjogren syndrome and Type I diabetes. Exemplary neurological diseases include Alzheimer's Disease, Parkinson's Disease, Amyotrophic lateral sclerosis, and Huntington's disease. Exemplary inflammatory diseases include atherosclerosis, allergy, and inflammation from infection or injury.

In one aspect, the compounds and pharmaceutical compositions of the invention specifically target tyrosine non-receptor kinases, in particular JAK2 and BTK. Thus, these compounds and pharmaceutical compositions can be used to prevent, reverse, slow, or inhibit the activity of one or more of these kinases. In preferred embodiments, methods of treatment target cancer. In other embodiments, methods are for treating lung cancer or non-small cell lung cancer.

In the inhibitory methods of the invention, an "effective amount" means an amount sufficient to inhibit the target protein. Measuring such target modulation may be performed by routine analytical methods such as those described below. Such modulation is useful in a variety of settings, including in vitro assays. In such methods, the cell is preferably a cancer cell with abnormal signaling due to upregulation of JAK2 or BTK.

In treatment methods according to the invention, an "effective amount" means an amount or dose sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to 1 g daily, or about 1 mg to 50 mg daily, or about 50 to 250 mg daily, or about 250 mg to 1 g daily. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Combination agents include additional active ingredients are those that are known or discovered to be effective in treating the diseases and disorders described herein, including those active against another target associated with the disease. For example, compositions and formulations of the invention, as well as methods of treatment, can further comprise other drugs or pharmaceuticals, e.g., other active agents useful for treating or palliative for the target diseases or related symptoms or conditions. For cancer indications, additional such agents include, but are not limited to, kinase inhibitors, such as EGFR inhibitors (e.g., erlotinib, gefitinib), Raf inhibitors (e.g., vemurafenib), VEGFR inhibitors (e.g., sunitinib), ALK inhibitors (e.g., crizotinib) standard chemotherapy agents such as alkylating agents, antimetabolites, anti-tumor antibiotics, topoisomerase inhibitors, platinum drugs, mitotic inhibitors, antibodies, hormone therapies, or corticosteroids. For pain indications, suitable combination agents include anti-inflammatories such as NSAIDs. The pharmaceutical compositions of the invention may additional comprise one or more of such active agents, and methods of treatment may additionally comprise administering an effective amount of one or more of such active agents.

Chemical Synthesis

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Abbreviations

The examples described herein use materials, including but not limited to, those described by the following abbreviations known to those skilled in the art:

| | |
|---|---|
| g | grams |
| eq | equivalents |
| mmol | millimoles |
| mL | milliliters |
| EtOAc | ethyl acetate |
| MHz | megahertz |
| ppm | parts per million |
| δ | chemical shift |
| s | singlet |
| d | doublet |
| t | triplet |
| q | quartet |
| quin | quintet |
| br | broad |
| m | multiplet |
| Hz | hertz |
| THF | tetrahydrofuran |
| °C. | degrees Celsius |
| PE | petroleum ether |
| EA | ethyl acetate |
| $R_f$ | retardation factor |
| N | normal |
| J | coupling constant |
| DMSO-$d_6$ | deuterated dimethyl sulfoxide |
| n-BuOH | n-butanol |
| DIEA | n,n-diisopropylethylamine |
| TMSCl | trimethylsilyl chloride |
| min | minutes |
| hr | hours |
| Me | methyl |
| Et | ethyl |
| i-Pr | isopropyl |
| TLC | thin layer chromatography |
| M | molar |
| Compd# | compound number |
| MS | mass spectrum |
| m/z | mass-to-charge ratio |
| Ms | methanesulfonyl |
| FDPP | pentafluorophenyl diphenylphosphinate |
| Boc | tert-butyloxycarbonyl |
| TFA | trifluoroacetic acid |
| Tos | toluenesulfonyl |
| DMAP | 4-(dimethylamino)pyridine |
| μM | micromolar |
| ATP | adenosine triphosphate |
| $IC_{50}$ | half maximal inhibitory concentration |
| U/mL | units of activity per milliliter |
| KHMDS | potassium bis(trimethylsilyl)amide |
| DIAD | diisopropyl azodicarboxylate |
| MeTHF | 2-methyltetrahydrofuran |
| MOM | methoxymethyl |
| DCM | dichloromethane |
| DMF | N,N-dimethylformamide |
| DPPA | diphenyl phosphoryl azide |
| DBU | 1,8-diazabicyclo[5.4.0]undec-7-ene |
| DIPEA | N,N-diisopropylethylamine |
| (A-phos)$_2$Cl$_2$Pd | Bis(di-tert-butyl(4-dimethylaminophenyl)phosphine)dichloropalladium (II) |

General Method A.

Preparation of ethyl (R)-5-((1-(5-fluoro-2-hydroxyphenyl)ethyl)amino)pyrazolo[1,5-a]pyrimidine-3-carboxylate (A-1)

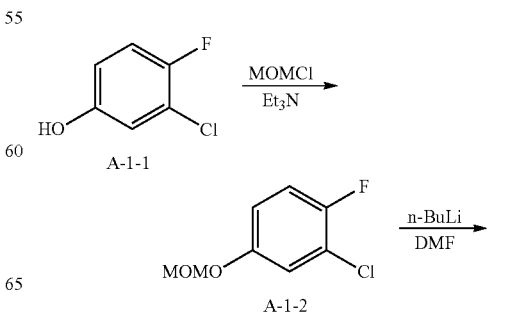

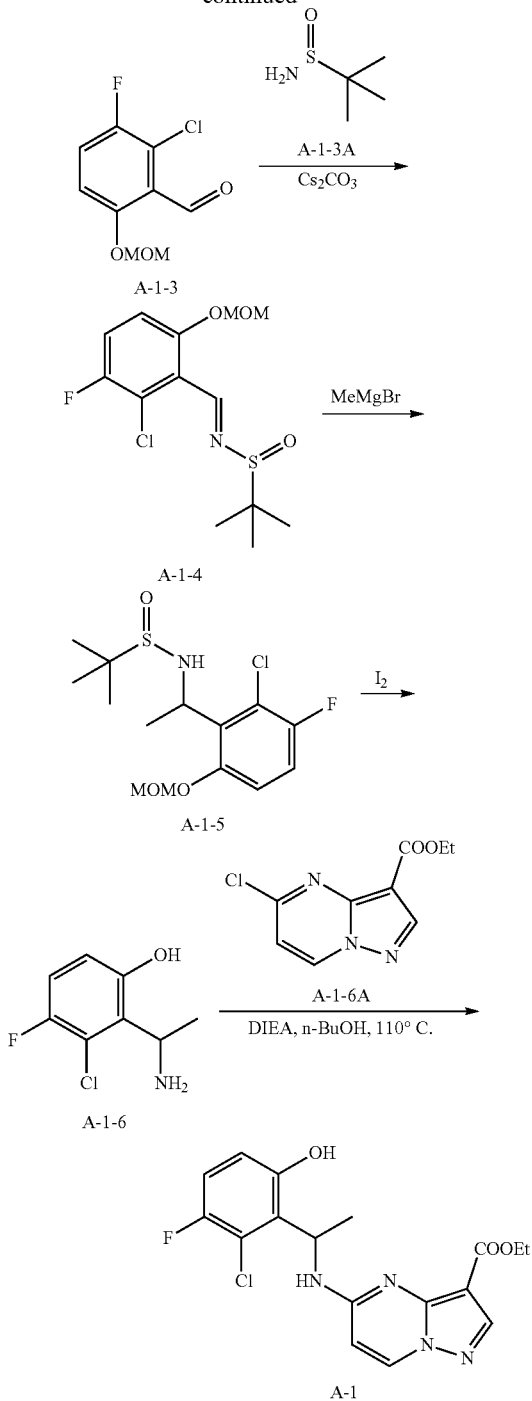

diluted with water (150 mL) and extracted with ethyl acetate (100 mL*3). The combined organic layers were washed with brine (150 mL), dried over anhydrous sodium sulfate, filtered and concentrated under reduced pressure to give A-1-2 (20.00 g, 76.89% yield) as a colorless oil. $^1$H NMR (400 MHz, CDCl$_3$) δ: 7.11 (dd, J=2.8, 6.0 Hz, 1H), 7.04 (t, J=8.8 Hz, 1H), 6.90 (td, J=3.2, 9.2 Hz, 1H), 5.12 (s, 2H), 3.47 (s, 3H).

Step 2. Preparation of 2-chloro-3-fluoro-6-(methoxymethoxy)benzaldehyde (A-1-3)

To a solution of A-1-2 (20.00 g, 104.93 mmol, 1.00 eq.) in THF (250.00 mL) was added n-BuLi (2.5 M, 125.92 mL, 3.00 eq.) at −65° C. under N$_2$. The mixture was stirred at −65° C. for 2 hours. The mixture was quenched by DMF (76.69 g, 1.05 mol, 80.73 mL, 10.00 eq.) and the mixture was stirred at −65° C. for 15 min under N$_2$. TLC (Petroleum ether:Ethyl acetate=3:1) showed the starting material was consumed completely and one new spot was found. The reaction mixture was diluted with water (300 mL) and extracted with ethyl acetate (150 mL*3). Then combined organic layers and dried over anhydrous sodium sulfate, filtered and concentrated under reduced pressure to give a residue. The residue was purified by column chromatography (SiO$_2$, Petroleum ether/Ethyl acetate=1/0 to 1/1) to give A-1-3 (4.80 g, 20.93% yield) as a colorless oil. $^1$H NMR (400 MHz, CDCl$_3$) δ: 10.48 (s, 1H), 7.28 (t, J=8.8 Hz, 1H), 7.15 (dd, J=4.0, 9.2 Hz, 1H), 5.25 (s, 2H), 3.51 (s, 3H).

Step 3. Preparation of (E)-N-(2-chloro-3-fluoro-6-(methoxymethoxy)benzylidene)-2-methylpropane-2-sulfinamide (A-1-4)

To a solution of A-1-3 (2.20 g, 10.06 mmol, 1.00 eq.) and A-1-3A (1.22 g, 10.06 mmol, 1.00 eq.) in THF (22.00 mL) was added cesium carbonate (6.56 g, 20.12 mmol, 2.00 eq.). The mixture was stirred at 25° C. for 4 hours. TLC (Petroleum ether/Ethyl acetate=3/1) showed starting material was consumed completely. The reaction mixture was diluted with water (50 mL) and extracted with ethyl acetate (30 mL*3). Then combined organic layers and dried over anhydrous sodium sulfate, filtered and concentrated under reduced pressure to give a residue. The residue was purified by column chromatography (SiO$_2$, Petroleum ether/Ethyl acetate=20/1 to 5/1) to give A-1-4 (1.20 g, 37.07% yield) as a colorless oil. $^1$H NMR (400 MHz, CDCl$_3$) δ: 8.95 (s, 1H), 7.27-7.18 (m, 1H), 7.18-7.11 (m, 1H), 5.28-5.18 (m, 3H), 3.55-3.44 (m, 4H), 1.32 (s, 9H)

Step 4. Preparation of N-(1-(2-chloro-3-fluoro-6-(methoxymethoxy)phenyl)ethyl)-2-methylpropane-2-sulfinamide (A-1-5)

To a solution of A-1-4 (2.20 g, 6.84 mmol, 1.00 eq.) in THF (22.00 mL) was added MeMgBr (3 M, 6.84 mL, 3.00 eq.) at −70° C. under N$_2$. The mixture was stirred at −70° C. for 3 hours. TLC (Petroleum ether/Ethyl acetate=1/1) indicated starting material was consumed completely and two new spot was found. The reaction mixture was quenched by water (40 mL), then diluted with water (40 mL) and extracted with ethyl acetate (70 mL*3). Then combined organic layers and dried over anhydrous sodium sulfate, filtered and concentrated under reduced pressure to give a residue. The residue was purified by column chromatography (SiO$_2$, Petroleum ether/Ethyl acetate=10/1 to 3/1) to give A-1-5 (1.40 g, 60.58% yield) as a colorless oil. $^1$H Step 1. Preparation of 2-chloro-1-fluoro-4-(methoxymethoxy)benzene (A-1-2)

To a solution of A-1-1 (20.00 g, 136.47 mmol, 1.00 eq.) and sodium hydride (6.55 g, 60% purity, 272.94 mmol, 2.00 eq.) in DMF (200.00 mL) was added MOMCl (21.97 g, 272.94 mmol, 20.73 mL, 2.00 eq.) at 0° C. under N$_2$. The mixture was stirred at 25° C. for 10 hours. TLC (Petroleum ether/Ethyl acetate=5/1) showed the starting material was consumed completely and one new spot was found. The reaction mixture was quenched by water (150 mL), and then NMR (400 MHz, CDCl₃) δ: 7.10-6.95 (m, 4H), 5.30-5.18 (m, 5H), 3.53 (d, J=7.2 Hz, 6H), 1.69 (d, J=7.0 Hz, 3H), 1.54 (d, J=7.2 Hz, 3H), 1.24-1.20 (m, 9H), 1.16 (s, 9H)

Step 5: Preparation of 2-(1-aminoethyl)-3-chloro-4-fluorophenol (A-1-6)

To a solution of A-1-5 (1.30 g, 3.85 mmol, 1.00 eq.) in THF (4.00 mL) and H₂O (1.00 mL) was added iodine (293.00 mg, 1.15 mmol, 0.30 eq.). The mixture was stirred at 60° C. for 3 hours. TLC (DCM/Methanol=20/1) indicated starting material was consumed completely and one new spot was found. The reaction mixture was diluted with water (20 mL) and extracted with ethyl acetate (15 mL*3). The combined organic layers were washed with water (10 mL*3), dried over anhydrous sodium sulfate, filtered and concentrated under reduced pressure to give A-1-6 (1.20 g, crude) as a light yellow solid.

Step 6. Preparation of ethyl ethyl 5-((1-(2-chloro-3-fluoro-6-hydroxyphenyl)ethyl)amino)pyrazolo[1,5-a]pyrimidine-3-carboxylate (A-1)

To a solution of A-1-6 (500.00 mg, 2.64 mmol, 1.10 eq.) and A-1-6A (541.51 mg, 2.40 mmol, 1.00 eq.) in n-BuOH (5.00 mL) was added DIEA (1.24 g, 9.60 mmol, 1.68 mL, 4.00 eq.). The mixture was stirred at 110° C. for 3 hours. TLC (DCM/Methanol=20/1) indicated starting material was consumed completely and one new spot was found. The reaction mixture was diluted with water (30 mL) and extracted with ethyl acetate (15 mL*3). The combined organic layers were washed with water (10 mL*3) and dried over anhydrous sodium sulfate, filtered and concentrated under reduced pressure to give a residue. The residue was purified by Prep-TLC (SiO₂, DCM/Methanol=20/1) to give A-1 (113.00 mg, 12.43% yield) as a light yellow solid.

General Method B.

Preparation of ethyl (R)-2-(1-aminoethyl)-6-chloro-4-fluorophenol (A-2-5)

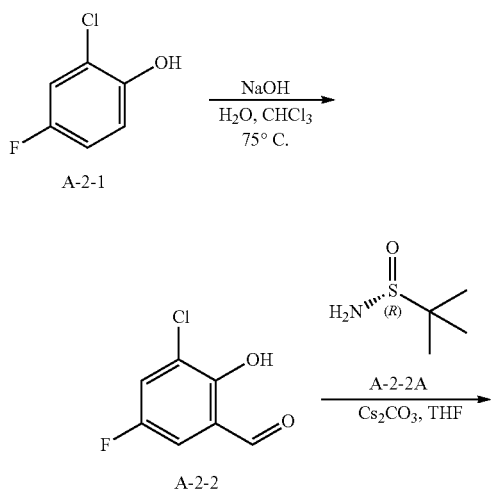

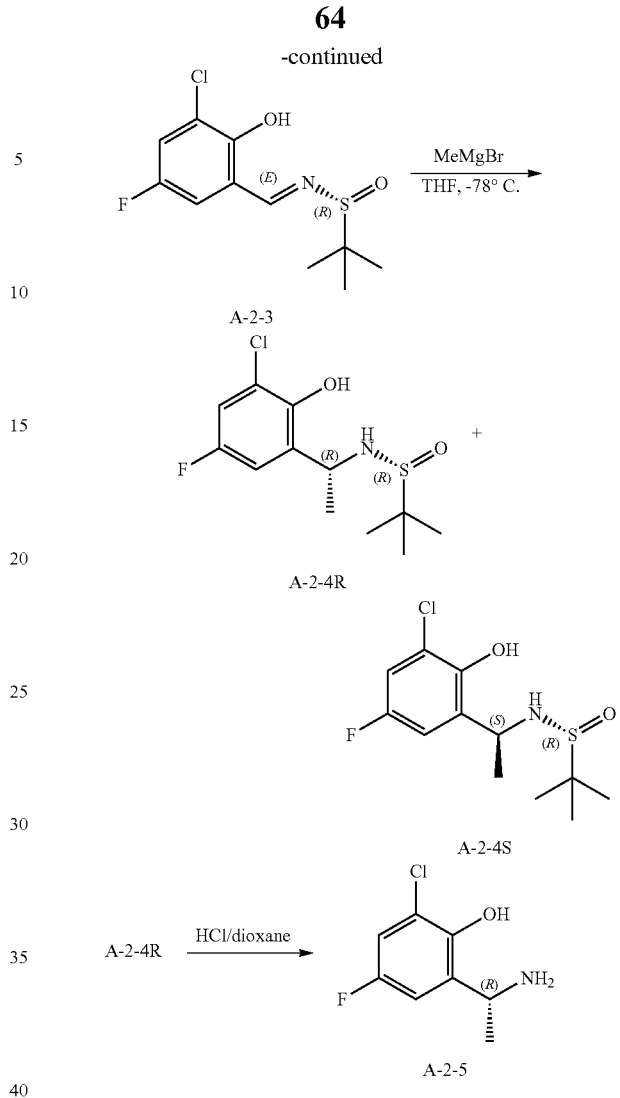

Step 1. To a solution of sodium hydroxide (50 g.) in chloroform/water (60 mL, v/v=1:1) was added A-2-1 (10 g, 0.068 mole). The mixture was refluxed for 2 hours. Chloroform (30 ml.) was added again and refluxed for another 2 hours. The reaction mixture was cooled to room temperature and crude product recovered as the sodium salt by filtration. The filter cake was taken into water and acidified with 1 N hydrochloric acid to PH=6 and then diluted by water (30 mL), extracted with ethyl acetate (45 mL). The combined organic layers were dried over anhydrous sodium sulfate, filtered and concentrated under reduced pressure to give A-2-2 (3.20 g, yield 27%) as a colorless oil. ¹H NMR (400 MHz, CDCl₃) δ 11.23 (s, 1H), 9.87 (s, 1H), 7.43 (dd, J=3.2, 8.0 Hz, 1H), 7.24 (dd, J=3.2, 7.2 Hz, 1H).

Step 2. To a solution of A-2-2 (3.20 g, 18.33 mmol, 1.00 eq.) and A-2-2A (2.22 g, 18.33 mmol, 1.00 eq.) in THF (32.00 mL) was added cesium carbonate (11.95 g, 36.66 mmol, 2.00 eq.). The mixture was stirred at 20° C. for 2 hours. Then the reaction mixture was quenched by added water (50 mL) and extracted with ethyl acetate (90 mL). The combined organic layers were dried over anhydrous sodium sulfate, filtered and concentrated under reduced pressure to give A-2-3 (5.10 g, crude) as a colorless oil. ¹H NMR (400 MHz, CDCl₃) δ 8.73 (s, 1H), 7.21 (ddd, J=3.2, 8.0, 16.0 Hz, 2H), 1.15 (s, 9H).

Step 3. To a solution of A-2-3 (5.10 g, 18.36 mmol, 1.00 eq.) in THF (17.00 mL) was added methyl magnesium bromide (3 M in THF, 15.30 mL, 2.50 eq.) drop-wise. The mixture was stirred at −75° C. for 2 hours. Then the reaction mixture was quenched by added water (30 mL) and extracted with ethyl acetate (60 mL). The combined organic layers were dried over anhydrous sodium sulfate, filtered and concentrated under reduced pressure to give a residue. The residue was purified by column chromatography (SiO$_2$, Petroleum ether/Ethyl acetate=10/1 to 1/1) to give A-2-4R (1.70 g, yield 31.52%) and A-2-4S (1.10 g, yield 20.39%) as yellow solid.

Step 4. A solution of A-2-4R (1.65 g, 5.62 mmol, 1.00 eq.) in HCl/dioxane (17.00 mL, 4 M) was stirred at 20° C. for 1 hour. Then the reaction mixture was diluted by water (30 mL) and extracted with ethyl acetate (50 mL). The combined organic layers were dried over anhydrous sodium sulfate, filtered and concentrated under reduced pressure to give A-2-5 (1.00 g, yield 93.84%) as a white solid. $^1$H NMR (400 MHz, DMSO-d$_6$) δ 9.85 (s, 1H), 8.57 (br s, 3H), 7.43-7.41 (m, 1H), 7.39 (s, 1H), 4.72-4.63 (m, 1H), 1.48 (d, J=6.8 Hz, 3H).

Preparation of (R)-ethyl 5-((1-(3-chloro-5-fluoro-2-hydroxyphenyl)ethyl)amino)pyrazolo[1,5-a]pyrimidine-3-carboxylate (A-2)

General Method A was followed for the preparation of A-2 using A-2-5 in step 6.

Preparation of (R)-ethyl 5-((1-(3-bromo-5-fluoro-2-hydroxyphenyl)ethyl)amino)pyrazolo[1,5-a]pyrimidine-3-carboxylate (A-3)

General Methods A and B were used to make A-3 starting with 3-bromo-5-fluoro-2-hydroxybenzaldehyde in step 2 of General Method B.
General Method C.

Preparation of ethyl 2,3-difluoro-6-(methoxymethoxy)benzaldehyde (A-4-3)

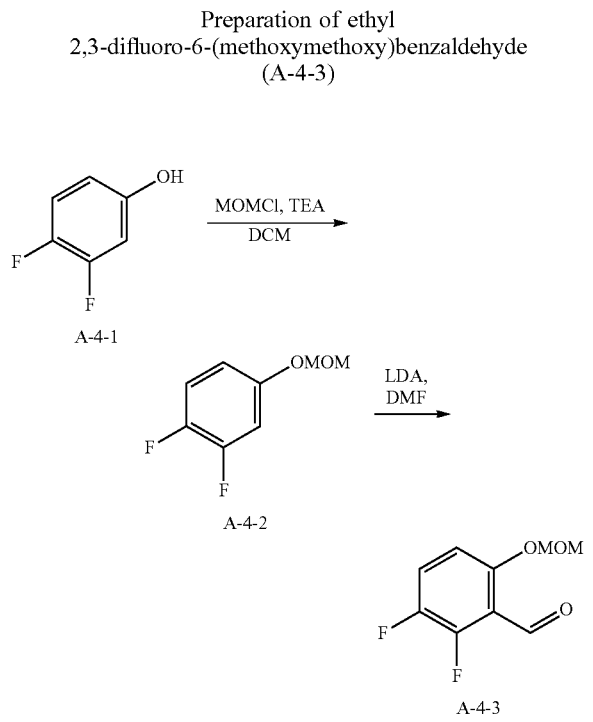

Step 1. To a solution of A-4-1 (17.50 g, 134.52 mmol, 1.00 eq.) in DMF (175.00 mL) was added sodium hydride (10.76 g, 269.04 mmol, 60% purity, 2.00 eq.) portion-wise under N$_2$ atmosphere. The mixture was stirred at 0° C. for 1 hour. Then the MOMCl (16.25 g, 201.78 mmol, 15.33 mL, 1.50 eq.) was added drop-wise and the mixture was stirred at 0° C. for another 1 hour. The reaction mixture was quenched by added water (200 mL) and extracted with ethyl acetate (300 mL). The combined organic layers were dried over anhydrous sodium sulfate, filtered and concentrated under reduced pressure to give a residue. The residue was purified by column chromatography (SiO$_2$, Petroleum ether/Ethyl acetate=10/1 to 1/1) to give A-4-2 (22.00 g, 93.92% yield) as a colorless oil. $^1$H NMR (400 MHz, CDCl$_3$) δ 7.06 (q, J=9.2 Hz, 1H), 6.92-6.87 (m, 1H), 6.76-6.74 (m, 1H), 5.12 (s, 2H), 3.48 (s, 3H).

Step 2. To a solution of A-4-2 (8.00 g, 45.94 mmol, 1.00 eq.) in THF (56.00 mL) was added LDA (2 M, 27.56 mL, 1.20 eq.). The mixture was stirred at −78° C. for 2 hours. Then the reaction mixture was diluted with water (80 mL) and extracted with ethyl acetate (120 mL×3). The combined organic layers were dried over anhydrous sodium sulfate, filtered and concentrated under reduced pressure to give the A-4-3 (5.00 g, crude) as colorless oil. $^1$H NMR (400 MHz, CDCl$_3$) δ 10.41 (s, 1H), 7.31 (q, J=9.2 Hz, 1H), 7.00-6.95 (m, 1H), 5.26 (s, 2H), 3.51 (s, 3H).

Preparation of (R)-ethyl 5-((1-(2,3-difluoro-6-hydroxyphenyl)ethyl)amino)pyrazolo[1,5-a]pyrimidine-3-carboxylate (A-4)

General Methods A and B were used to make A-4 starting with A-4-3 in step 2 of General Method B.
General Method D.

Preparation of 2,4-difluoro-6-((isopropylamino)methyl)phenol (A-5-3)

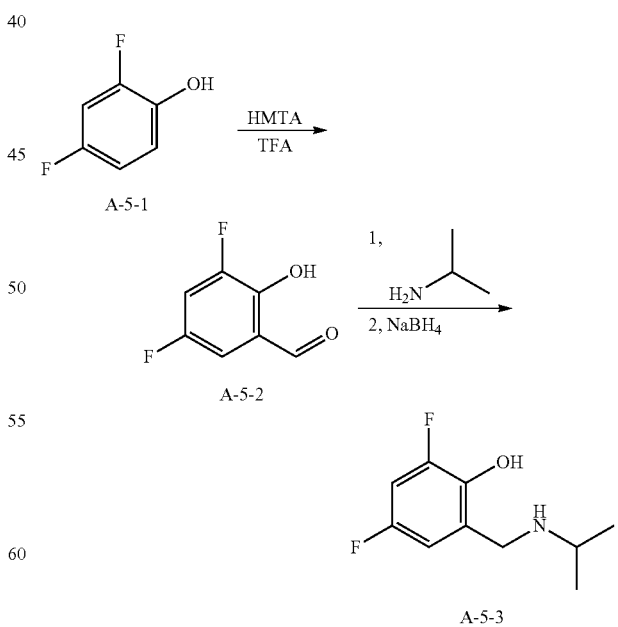

Step 1. A solution of HMTA (21.55 g, 153.74 mmol, 28.73 mL, 1.00 eq.) in TFA (350.00 mL) was stirred at 78° C. for 0.5 hour, then A-5-1 (20.00 g, 153.74 mmol, 1.00 eq.) in TFA (150.00 mL) was added drop-wise at 78° C. The resulting mixture was stirred at 78° C. for 1 hour. Then the reaction mixture was concentrated under reduced pressure to remove TFA. The residue was poured into ice-water (500 mL) and stirred overnight. Then the mixture was filtered and filter cake was concentrated to give A-5-2 (8.00 g, 32.91% yield) as a white solid. $^1$H NMR (400 MHz, CDCl$_3$) δ 10.71 (br s, 1H), 9.89 (d, J=2.0 Hz, 1H), 7.21-7.16 (m, 1H), 7.15-7.10 (m, 1H).

Step 2. To a solution of A-5-2 (2.00 g, 12.65 mmol, 1.00 eq.) and propan-2-amine (1.50 g, 25.30 mmol, 2.00 eq.) in THF (10.00 mL) was added anhydrous magnesium sulfate (8.43 mL, 25.30 mmol, 3 M, 2.00 eq.). After stirred at 20° C. for 16 hours, then sodium borohydride (478.56 mg, 12.65 mmol, 1.00 eq.) was added. The mixture was stirred at 20° C. for 2 hours. Then the reaction mixture was quenched by added water (1 mL) and diluted with water (30 mL) and extracted with ethyl acetate (50 mL×3). The combined organic layers were dried over anhydrous sodium sulfate, filtered and concentrated under reduced pressure to give A-5-3 (1.10 g, 29.60% yield) as colorless oil which used for the next step without further purification.

Preparation of ethyl 5-((3,5-difluoro-2-hydroxybenzyl)(isopropyl)amino)pyrazolo[1,5-a]pyrimidine-3-carboxylate (A-5)

General Method A was used to make A-5 starting with A-5-3 in step 6.

Preparation of ethyl 5-((3-chloro-5-fluoro-2-hydroxybenzyl)(isopropyl)amino)pyrazolo[1,5-a]pyrimidine-3-carboxylate (A-6)

General Methods A and D were used to make A-6 starting with A-2-2 in step 2 of General Methods D.
General Method E.

Preparation of 2-chloro-3-fluoro-6-(methoxymethoxy)benzaldehyde (A-7-3)

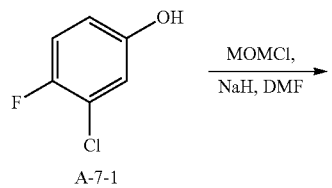

Step 1. To a solution of A-7-1 (51.00 g, 348.00 mmol, 1.00 eq.) in DMF (300.00 mL) was added sodium hydride (2.73 g, 68.24 mmol, 60% purity, 2.00 eq.) at 0° C. under N$_2$ protection. The mixture was stirred at 0° C. for 2 hours under N$_2$ protection. Then chloromethyl methyl ether (38.32 g, 475.97 mmol, 36.15 mL, 1.37 eq.) was added to the mixture at 0° C. and the mixture was stirred at 25° C. for 8 hours. Then the mixture was quenched by water (1000 mL) and extracted with ethyl acetate (300 mL×3). The organic layers were washed by brine (500 mL), dried over anhydrous sodium sulfate, concentrated to give A-7-2 (60.00 g, 314.80 mmol, 90.46% yield) as a colorless oil. $^1$H NMR (400 MHz, CDCl$_3$) δ: 7.11 (dd, J=3.2, 6.0 Hz, 1H), 7.07-7.01 (m, 1H), 6.94-6.86 (m, 1H), 5.12 (s, 2H), 3.48 (s, 3H).

Step 2. To a solution of A-7-2 (40.00 g, 209.86 mmol, 1.00 eq) in t-butyl methyl ether (350.00 mL) was added n-BuLi (20.17 g, 314.80 mmol, 2.5 M in hexane, 1.50 eq.) drop-wise at −65° C. under N$_2$ protection. The mixture was stirred at −65° C. for 2 hours. Then methyl formate (50.41 g, 839.45 mmol, 50.92 mL, 4.00 eq.) was added into the mixture at −65° C. under N$_2$ protection and the mixture was stirred at 20° C. for 15 hours. The mixture was quenched by water (200 mL) and extracted with ethyl acetate (200 mL×3). The organic layer was washed by brine (500 mL) and dried over anhydrous sodium sulfate. The residue was purified by column chromatography (SiO$_2$, Petroleum ether/Ethyl acetate=20/1 to 1:1) to give A-7-3 (10.00 g, 45.74 mmol, 21.80% yield) as a yellow oil. $^1$H NMR (400 MHz, CDCl$_3$) δ 10.49 (d, J=0.8 Hz, 1H), 7.32-7.28 (m, 1H), 7.16 (dd, J=4.0, 9.2 Hz, 1H), 5.26 (s, 2H), 3.52 (s, 3H).

Preparation of ethyl ethyl 5-((2-chloro-3-fluoro-6-hydroxybenzyl)(isopropyl)amino)pyrazolo[1,5-a]pyrimidine-3-carboxylate (A-7)

General Methods A and D were used to make A-7 starting with A-7-3 in step 2 of General Method D.

| Compd # | Structure | MS m/z | $^1$H NMR (400 MHz, CDCl$_3$) δ ppm |
|---|---|---|---|
| A-1 | 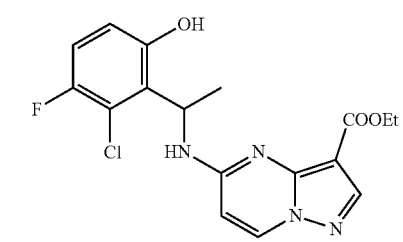 [SMILES: CCOC(=O)c1cnn2ccc(NC(C)c3c(O)ccc(F)c3Cl)nc12] | 379.0 | 8.26 (br. s., 1H), 8.23-8.17 (m, 2H), 7.01-6.93 (m, 2H), 6.19 (d, J = 7.6 Hz, 1H), 6.09-5.92 (m, 2H), 4.43 (d, J = 4.0, 7.2 Hz, 2H), 1.82 (d, J = 7.2 Hz, 3H), 1.41 (t, J = 7.2 Hz, 4H) |

-continued
| Compd # | Structure | MS m/z | ¹H NMR (400 MHz, CDCl₃) δ ppm |
|---|---|---|---|
| A-2 | 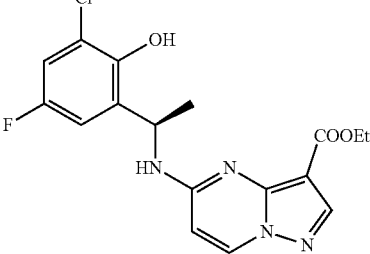 | 379.0 | 8.27 (s, 1H), 8.19 (d, J = 7.6 Hz, 1H), 7.01 (dd, J = 3.2, 7.6 Hz, 1H), 6.90 (dd, J = 3.2, 9.2 Hz, 1H), 6.14 (d, J = 7.6 Hz, 1H), 5.76-5.66 (m, 1H), 5.62 (br s, 1H), 4.49-4.43 (m, 2H), 1.62 (d, J = 6.8 Hz, 3H), 1.44 (t, J = 7.2 Hz, 3H) |
| A-3 | 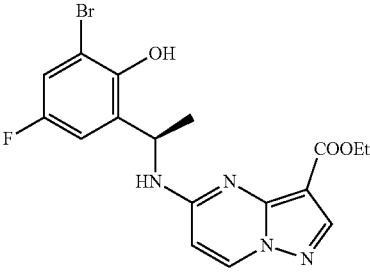 [SMILES: CCOC(=O)c1cnn2ccc(N[C@H](C)c3cc(F)cc(Br)c3O)nc12] | 423.0 | 8.94 (br s, 1H), 8.27 (s, 1H), 8.19 (d, J = 7.6 Hz, 1H), 7.17 (dd, J = 3.2, 7.6 Hz, 1H), 6.95 (dd, J = 3.2, 8.8 Hz, 1H), 6.12 (d, J = 7.6 Hz, 1H), 5.65 (br s, 2H), 4.48 (q, J = 7.2 Hz, 2H), 1.62 (d, J = 6.8 Hz, 3H), 1.46 (t, J = 7.2 Hz, 3H); |
| A-4 | 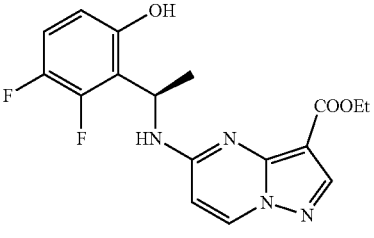 [SMILES: CCOC(=O)c1cnn2ccc(N[C@H](C)c3c(O)ccc(F)c3F)nc12] | 385.0 | 8.53 (br s, 1H), 8.23 (s, 1H), 8.21 (d, J = 7.2 Hz, 1H), 6.94 (q, J = 9.2 Hz, 1H), 6.78 (ddd, J = 2.0, 4.0, 9.2 Hz, 1H), 6.16 (d, J = 7.6 Hz, 1H), 5.80-5.66 (m, 2H), 4.44 (dq, J = 2.0, 7.2 Hz, 2H), 1.78 (dd, J = 2.0, 6.8 Hz, 3H), 1.41 (t, J = 7.2 Hz, 3H) |
| A-5 | 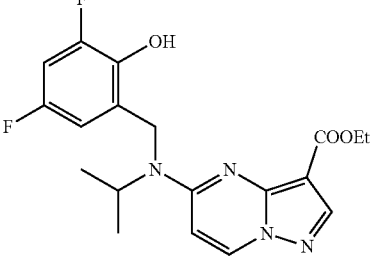 | 391.0 | 8.33-8.28 (m, 2H), 6.82-6.72 (m, 2H), 6.44 (br d, J = 8.0 Hz, 1H), 4.83 (s, 2H), 4.49-4.30 (m, 3H), 1.40-1.35 (m, 9H) |
| A-6 | 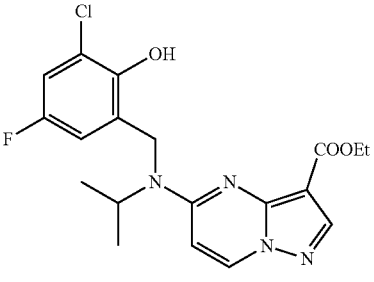 [SMILES: CCOC(=O)c1cnn2ccc(N(Cc3cc(F)cc(F)c3O)C(C)C)nc12] | 406.9 | 8.29 (d, J = 7.2 Hz, 1H), 7.04 (dd, J = 3.2, 8.0 Hz, 1H), 6.86 (dd, J = 2.8, 8.8 Hz, 1h), 6.37 (br d, J = 5.2 Hz, 1H), 4.80 (br s, 2H), 4.56 (br s, 1H), 4.37 (q, J = 7.2 Hz, 2H), 1.38-1.32 (m, 9H) |

| Compd # | Structure | MS m/z | $^1$H NMR (400 MHz, CDCl$_3$) δ ppm |
|---|---|---|---|
| A-7 | (structure) | 407.0 | 10.34 (s, 1h), 8.34 (d, J = 8.0 Hz, 1H), 8.32 (s, 1H), 7.02 (t, J = 8.8 Hz, 1H), 6.80 (dd, J = 4.8, 9.2 Hz, 1H), 6.55 (d, J = 8.0 Hz, 1H), 5.19 (s, 2H), 4.37 (q, J = 7.2 Hz, 2H), 4.27-4.20 (m, 1H), 1.37 (d, J = 7.2 Hz, 6H), 1.33 (t, J = 7.2 Hz, 3H) |

General Method F.

Preparation of (7S,13R)-9,11-difluoro-7,13-dimethyl-6,7,13,14-tetrahydro-1,15-ethenopyrazolo[4,3-f][1,4,8,10]benzoxatriazacyclotridecin-4(5H)-one (1)

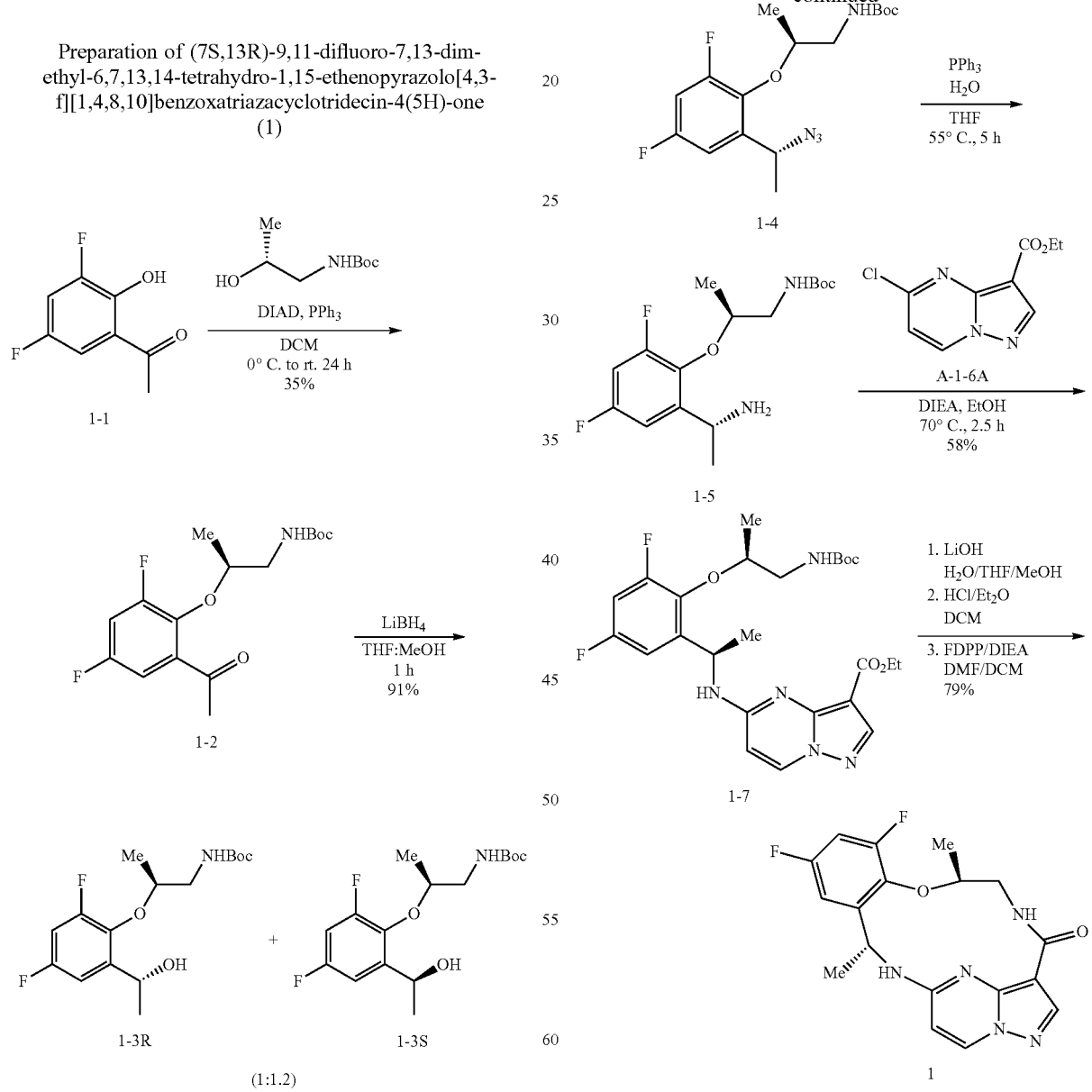

Step 1. To a solution of azeotrope dried phenol 1-1 (250 mg, 1.45 mmol) and (R)-tert-butyl (2-hydroxypropyl)carbamate (762 mg, 4.35 mmol) in dichloromethane (750 µL) was added PPh3 (1.14 g, 4.35 mmol). The mixture was stirred until completely dissolved then cooled to 0° C. and DIAD (879 mg, 4.35 mmol, 856 µL) was added dropwise with mixing. The mixture was warmed to room temperature and stirred for 24 hours then quenched by addition to water (75 mL) and extracted with DCM (3×50 mL). Combined extracts were dried with Na₂SO₄ and concentrated under reduced pressure. Flash chromatography (ISCO system, silica (24 g), 0-15% ethyl acetate in hexane) provided 1-2 (169.1 mg, 513 µmol, 35% yield).

Step 2. To a solution of 1-2 (169.1 mg, 513 µmol) in THF (3.0 mL) was added LiBH₄ (22.4 mg, 1.03 mmol) then MeOH (50 µL) and the mixture stirred for 1 hour. Reaction was quenched by addition of MeOH (1 mL) and water (1 mL) and stirred for 5 min then pH adjusted to acidic with 2 M HCl. The mixture was extracted with DCM (3×15 mL), dried with Na₂SO₄ and concentrated under reduced pressure. Flash chromatography (ISCO system, silica (12 g), 0-25% ethyl acetate in hexane) provided 1-3R (70.1 mg, 211 µmol, 41% yield) and 1-3S (85.5 mg, 258 µmol, 50% yield).

Step 3. To a solution of 1-3S (85.5 mg, 258 µmol) in toluene (600 µL) and DCM (200 µL) was added diphenyl phosphoryl azide (266 mg, 1.10 mmol, 209 uL) and DBU (177 mg, 1.16 mmol, 174 µL). The reaction mixture was stirred for 16 hours, quenched by addition to 0.2 M HCl (10 mL) then extracted with DCM (3×10 mL). Combined organic extracts were dried with Na₂SO₄ and concentrated under reduced pressure. Flash chromatography (ISCO system, silica (12 g), 0-25% ethyl acetate in hexane) provided 1-4 (81.0 mg, 227 µmol, 88% yield).

Step 4. To a solution of 1-4 (81.0 mg, 227 µmol) in THF (1.14 mL) was added PPh₃ (89 mg, 341 µmol) and the reaction mixture stirred for 5 hours. To this mixture was added H₂O (164 mg, 9.09 mmol, 164 µL) and stirring was continued overnight. The reaction mixture was heated to 55° C. for 5 hours, concentrated under reduced pressure and dried on high vacuum overnight to give crude 1-5.

Step 5. To a mixture of 1-5 (75 mg, 227 µmol) and A-1-6A (51 mg, 227 µmol) in EtOH (1.14 mL) was added Hünig's base (88 mg, 681 µmol, 119 uL). The mixture was stirred at 70° C. for 2.5 hours then concentrated under reduced pressure. Flash chromatography (ISCO system, silica (12 g), 0-60% ethyl acetate in hexane) provided 1-7 (69.3 mg, 133 µmol, 58% yield).

Step 6. To a solution of 1-7 (69.3 mg, 133 µmol) in MeOH (3 mL) and THF (1 mL) at ambient temperature was added aqueous LiOH solution (2.0 M, 1 mL). The mixture was heated at 70° C. for 3 hours, cooled to −20° C. then quenched with aqueous HCl solution (2.0 M, 1.1 mL) to acidic. The mixture was extracted with DCM (3×5 mL), dried with Na₂SO₄, concentrated under reduced pressure, and dried under high vacuum. The crude material was dissolved in DCM (3 mL) followed by addition of HCl in ether (2 M, 2 mL). The mixture was stirred ambient temperature for 3.5 hours, concentrated under reduced pressure, and dried under high vacuum. The crude material was dissolved in in DMF (1.0 mL) and DCM (4.0 mL) and Hünig's base (136 mg, 1.06 mmol, 184 µL) then FDPP (66 mg, 172 µmol) was added in one portion. The reaction was stirred for 1 hour then quenched with 2 M Na₂CO₃ solution (5 mL). Mixture was stirred for 5 min then extracted with DCM (4×10 mL). Combined extracts were dried with Na₂SO₄ and concentrated under reduced pressure. Flash chromatography (ISCO system, silica (12 g), 0-5% methanol in dichloromethane) provided 1 (39.2 mg, 105 µmol, 79% yield).

General Method G.

Preparation of (7S,13R)-12-chloro-11-fluoro-7,13-dimethyl-6,7,13,14-tetrahydro-1,15-ethenopyrazolo[4,3-f][1,4,8,10]benzoxatriazacyclotridecin-4(5H)-one (2)

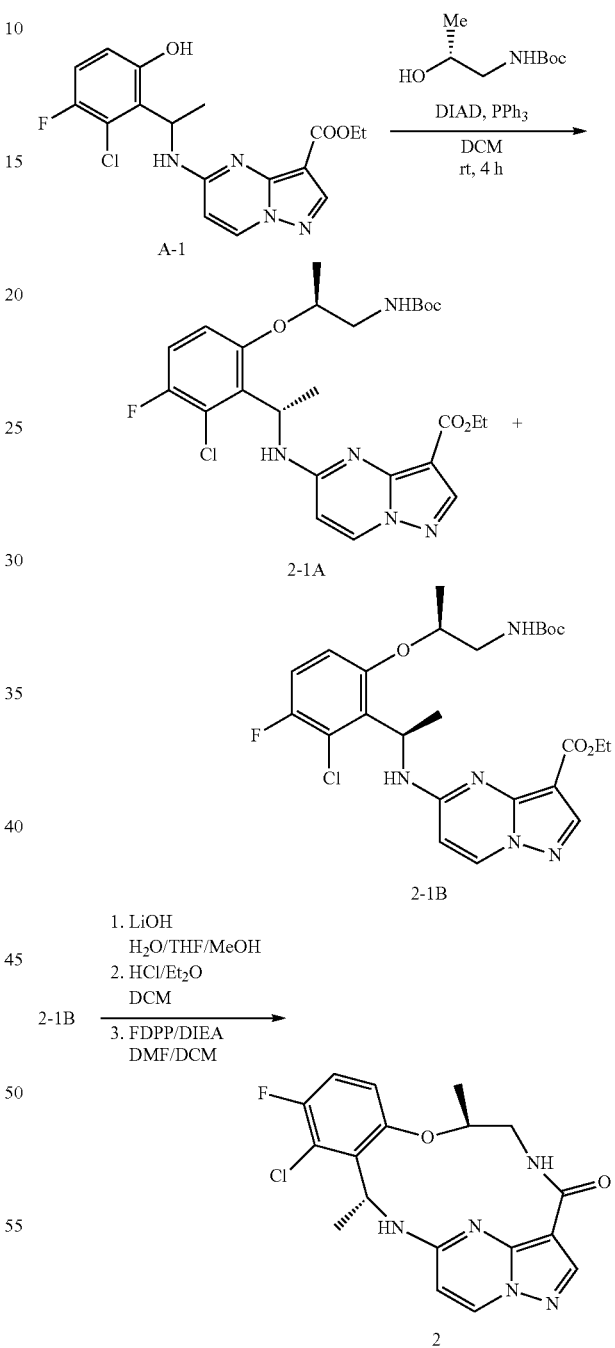

Step 1. Mixed A-1 (113.00 mg, 298.32 µmol) and (R)-tert-butyl (2-hydroxypropyl)carbamate (104.55 mg, 596.64 µmol) together and azeotrope dried from DCM:Toluene. Then r dissolved in DCM (200.00 uL) and added PPh3 (160.40 mg, 611.56 µmol) Mixture was stirred till everything completely dissolved. Added in DIAD (123.66 mg, 611.56 µmol, 120.06 uL) very slowly with mixing. Reaction was stirred for 4 hours then quenched by addition to water (4 mL) and extracted with DCM (3×3 mL). Combined extracts were dried with Na$_2$SO$_4$ and concentrated under reduced pressure. Flash chromatography (ISCO system, silica (12 g), 0-70% ethyl acetate in hexane) provided 2-1A (17.30 mg, 32.28 µmol, 10% yield) and 2-1B (80.60 mg, 150.37 µmol, 50% yield).

Step 2. 2-1B was converted to 2 following step 6 in General Method F.

General Method H.

Preparation of (7S,13R)-9,11-difluoro-7-(hydroxymethyl)-13-methyl-6,7,13,14-tetrahydro-1,15-ethenopyrazolo[4,3-f][1,4,8,10]benzoxatriazacyclotridecin-4(5H)-one (3)

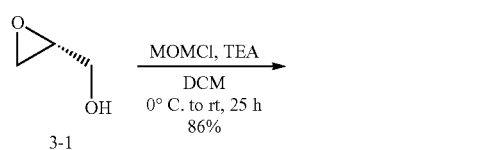
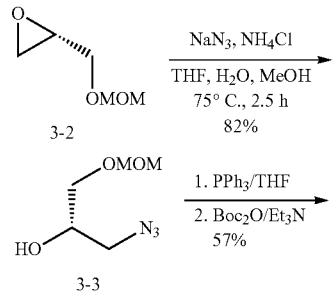
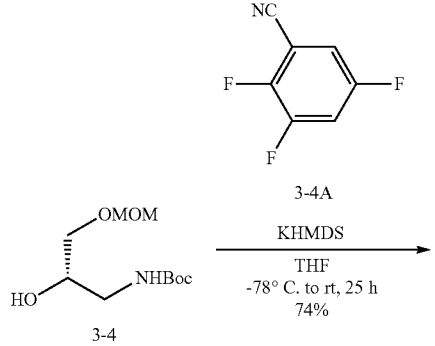
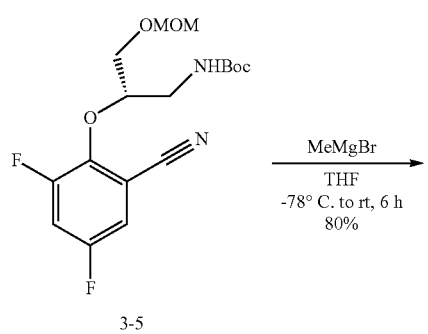
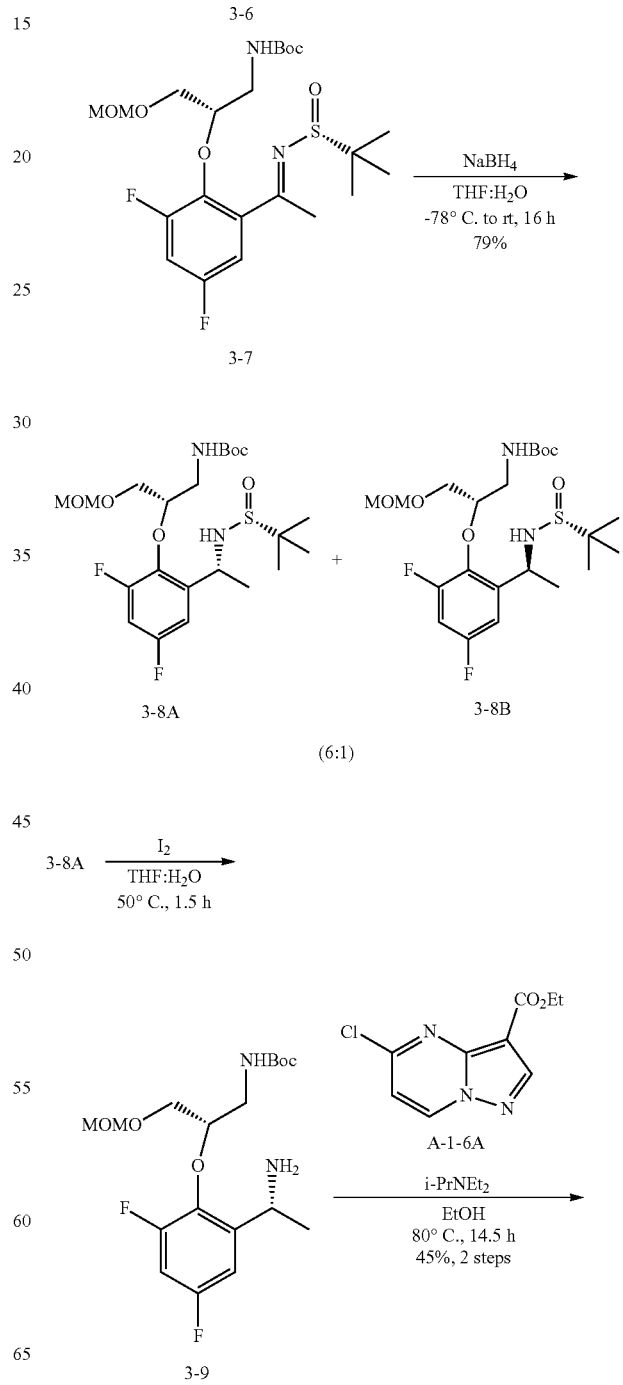

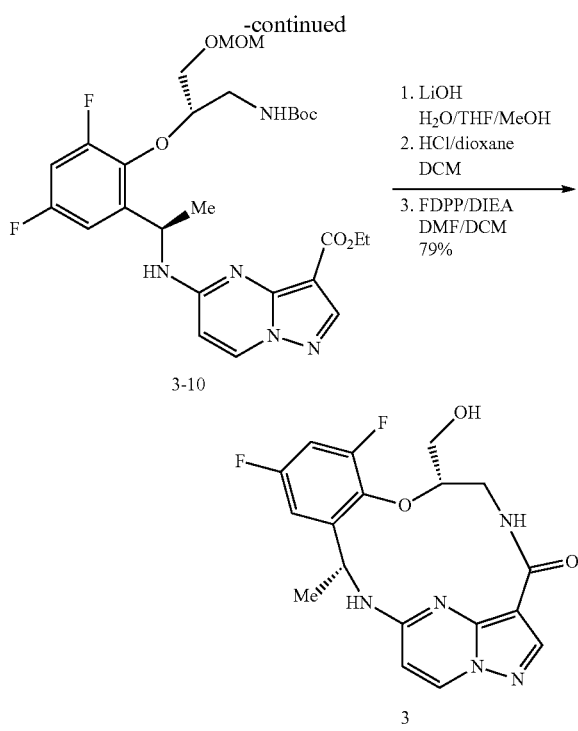

Step 1. To a solution of 3-1 (1.00 g, 13.5 mmol) and MOMCl (1.63 g, 20.3 mmol) in DCM (67 mL) at 0° C. was added Hünig's base (5.34 g, 41.3 mmol). The reaction was warmed to room temperature and stirred for 20 hour then quenched by addition to water (50 mL). The mixture was extracted with DCM (3×50 mL), dried with $Na_2SO_4$ and concentrated under reduced pressure. Flash chromatography (ISCO system, silica (24 g), 0-50% ethyl acetate in hexane) provided 3-2 (1.38 g, 11.7 mmol, 86% yield).

Step 2. A mixture of 3-2 (1.00 g, 8.47 mmol), $NaN_3$ (2.75 g, 42.3 mmol) and $NH_4Cl$ (1.04 g, 19.5 mmol) in $H_2O$ (3.14 mL), MeOH (22 mL) and THF (3.14 mL) was heated to 75° C. for 2.5 hours. The reaction was cooled and water (100 mL) added followed by extracted with ethyl acetate (3×50 mL), combined extracts were dried with brine (50 mL) and $Na_2SO_4$ then concentrated under reduced pressure. Flash chromatography (ISCO system, silica (24 g), 0-25% ethyl acetate in hexane) provided 3-3 (1.12 g, 6.95 mmol, 82% yield).

Step 3. To a solution of 3-3 (1.01 g, 6.27 mmol) in THF (21 mL) was added $PPh_3$ (2.47 g, 9.40 mmol), and the reaction solution was stirred at ambient temperature for 14 hours. To the reaction solution was added $H_2O$ (2.03 g, 112.86 mmol), and the mixture was stirred for 3 hours followed by addition of $Boc_2O$ (2.05 g, 9.40 mmol) and triethylamine (2.38 g, 23.56 mmol). The reaction was stirred at ambient temperature for 1 hour, quenched by addition to water (50 mL), extracted with DCM (3×50 mL), dried with $Na_2SO_4$, and concentrated under reduced pressure. Flash chromatography (ISCO system, silica (40 g), 25-40% ethyl acetate in hexane) provided the first fraction of 3-4 (850.6 mg, 3.62 mmol, 57% yield).

Step 4. To a solution of 3-4 (225 mg, 955 μmol) (azeotrope dried) and 3-4A (150.00 mg, 955 μmol) in THF (4.75 mL) at −78° C. was added KHMDS (1 M, 1.00 mL) dropwise. The reaction was warmed to room temperature and stirred for 25 hours. The reaction was quenched with saturated $NH_4Cl$ solution (10 mL) then extracted with DCM (3×10 mL). Combined extracts were dried with $Na_2SO_4$ and concentrated under reduced pressure. Flash chromatography (ISCO system, silica (12 g), 0-25% ethyl acetate in hexane) provided 3-5 (263.5 mg, 707 μmol, 74% yield).

Step 5. To a solution of 3-5 (263.5 mg, 707 μmol) in THF (4.0 mL) at −78° C. was added MeMgBr (3 M, 1.18 mL). The reaction mixture was warmed to room temperature, stirred for 6 hours then cooled back down to −78° C. and quenched with MeOH (3.95 g, 123 mmol, 5.0 mL) and water (5 mL). Mixture was stirred for 5 min then extracted with DCM (3×10 mL). Combined extracts were dried with $Na_2SO_4$ and concentrated under reduced pressure. Flash chromatography (ISCO system, silica (12 g), 0-50% ethyl acetate in hexane) provided 3-6 (220.5 mg, 566 μmol, 80% yield).

Step 6. To a solution of 3-6 (220.5 mg, 566 μmol), (R)-2-methylpropane-2-sulfinamide (137 mg, 1.13 mmol) and diglyme (75.98 mg, 566 μmol, 81 μL) in THF (566 μL) and MeTHF (566 μL) was added $Ti(OEt)_4$ (349 mg, 1.53 mmol, 320 μL). The mixture was heated to 60° C. for 18 hour. The reaction was cooled to room temperature and quenched by addition to water (20 mL). The mixture was extracted with DCM (3×15 mL), dried with $Na_2SO_4$ and concentrated under reduced pressure. Flash chromatography (ISCO system, silica (12 g), 0-40% ethyl acetate in hexane) provided 3-7 (92.0 mg, 187 μmol, 33% yield).

Step 7. To a solution of 3-7 (92.0 mg, 187 μmol) and $H_2O$ (11.8 mg, 654 μmol, 11.8 μL) in THF (1.27 mL) at −78° C. was added $NaBH_4$ (21.2 mg, 560 μmol). The reaction was slowly warmed to room temperature and stirred for 16 hours. The reaction cooled to −78 and quenched with excess MeOH then water and extracted with DCM (3×10 mL). Combined extracts were dried with $Na_2SO_4$ and concentrated under reduced pressure. Flash chromatography (ISCO system, silica (12 g), 0-100% ethyl acetate in hexane) provided 3-8A (63.4 mg, 128 μmol, 68.6% yield) and 3-8B (9.9 mg, 20 μmol, 10.7% yield).

Step 8. To a solution of 3-8A (63.40 mg, 128.19 μmol) in THF (535 μL) and $H_2O$ (107 μL) was added $I_2$ (6.5 mg, 25 μmol). The mixture was heated to 50° C. for 1.5 hours then cooled and concentrated under reduced pressure to give 3-9. Compound was dried on high vacuum and used as is.

3-9 was converted into 3 following the procedure of General Method F starting at step 5.

General Method I.

Preparation of (7S,13R)-12-chloro-11-fluoro-7-(hydroxymethyl)-13-methyl-6,7,13,14-tetrahydro-1,15-ethenopyrazolo[4,3-f][1,4,8,10]benzoxatriazacyclotridecin-4(5H)-one (4)

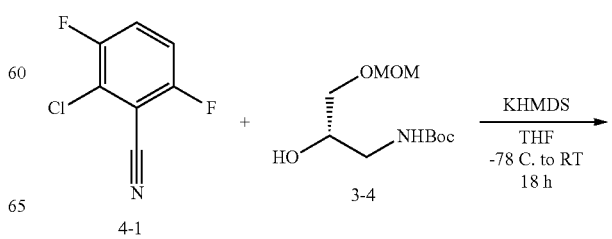

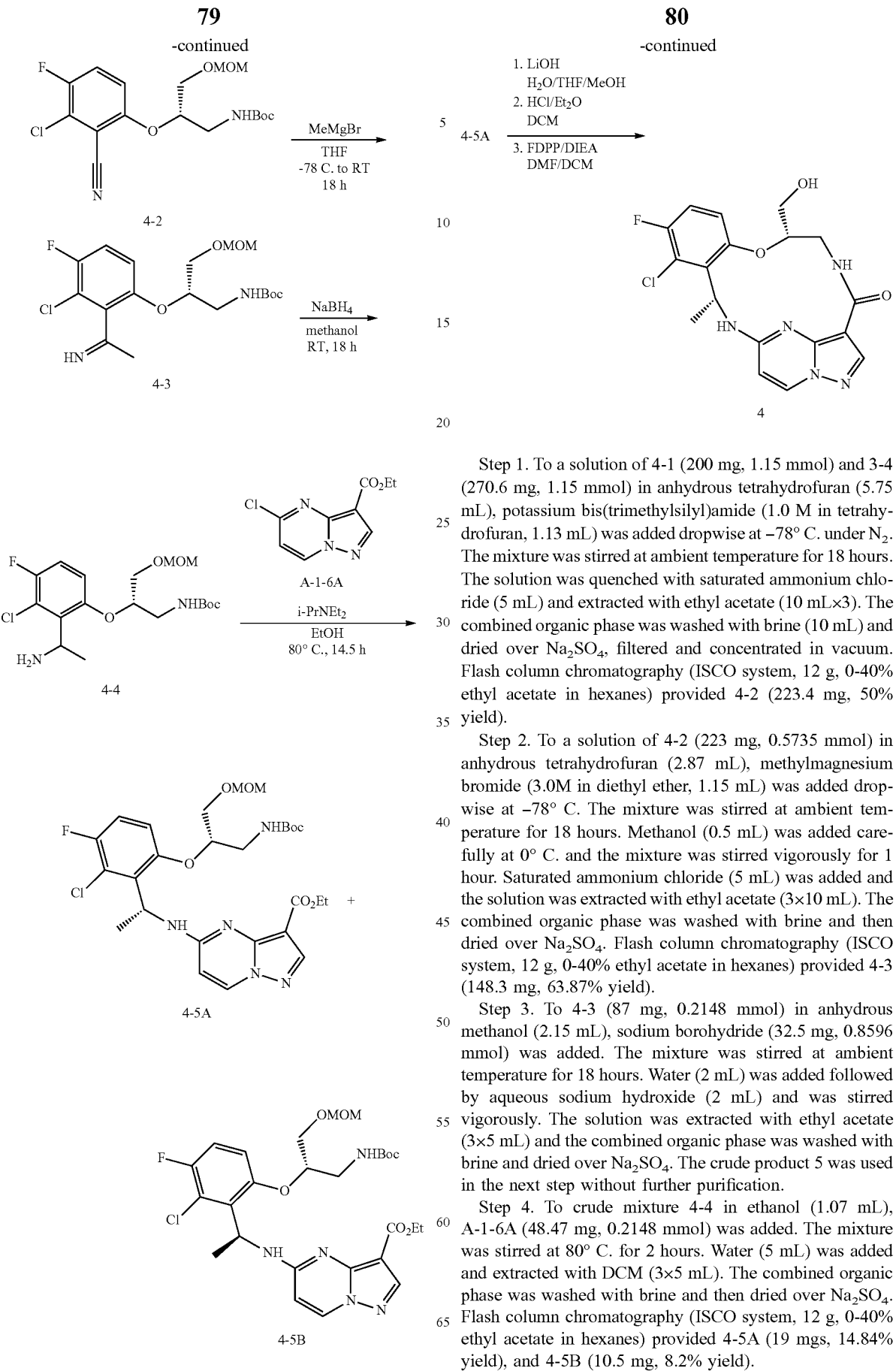

Step 1. To a solution of 4-1 (200 mg, 1.15 mmol) and 3-4 (270.6 mg, 1.15 mmol) in anhydrous tetrahydrofuran (5.75 mL), potassium bis(trimethylsilyl)amide (1.0 M in tetrahydrofuran, 1.13 mL) was added dropwise at −78° C. under N$_2$. The mixture was stirred at ambient temperature for 18 hours. The solution was quenched with saturated ammonium chloride (5 mL) and extracted with ethyl acetate (10 mL×3). The combined organic phase was washed with brine (10 mL) and dried over Na$_2$SO$_4$, filtered and concentrated in vacuum. Flash column chromatography (ISCO system, 12 g, 0-40% ethyl acetate in hexanes) provided 4-2 (223.4 mg, 50% yield).

Step 2. To a solution of 4-2 (223 mg, 0.5735 mmol) in anhydrous tetrahydrofuran (2.87 mL), methylmagnesium bromide (3.0M in diethyl ether, 1.15 mL) was added dropwise at −78° C. The mixture was stirred at ambient temperature for 18 hours. Methanol (0.5 mL) was added carefully at 0° C. and the mixture was stirred vigorously for 1 hour. Saturated ammonium chloride (5 mL) was added and the solution was extracted with ethyl acetate (3×10 mL). The combined organic phase was washed with brine and then dried over Na$_2$SO$_4$. Flash column chromatography (ISCO system, 12 g, 0-40% ethyl acetate in hexanes) provided 4-3 (148.3 mg, 63.87% yield).

Step 3. To 4-3 (87 mg, 0.2148 mmol) in anhydrous methanol (2.15 mL), sodium borohydride (32.5 mg, 0.8596 mmol) was added. The mixture was stirred at ambient temperature for 18 hours. Water (2 mL) was added followed by aqueous sodium hydroxide (2 mL) and was stirred vigorously. The solution was extracted with ethyl acetate (3×5 mL) and the combined organic phase was washed with brine and dried over Na$_2$SO$_4$. The crude product 5 was used in the next step without further purification.

Step 4. To crude mixture 4-4 in ethanol (1.07 mL), A-1-6A (48.47 mg, 0.2148 mmol) was added. The mixture was stirred at 80° C. for 2 hours. Water (5 mL) was added and extracted with DCM (3×5 mL). The combined organic phase was washed with brine and then dried over Na$_2$SO$_4$. Flash column chromatography (ISCO system, 12 g, 0-40% ethyl acetate in hexanes) provided 4-5A (19 mgs, 14.84% yield), and 4-5B (10.5 mg, 8.2% yield).

Step 5. 4-5b was converted to 4 following step 6 in General Method F.

General Method J.

Preparation of (13R)-9-bromo-11-fluoro-13-methyl-6,7,13,14-tetrahydro-1,15-ethenopyrazolo[4,3-f][1,4,8,10]benzoxatriazacyclotridecin-4(5H)-one (5)

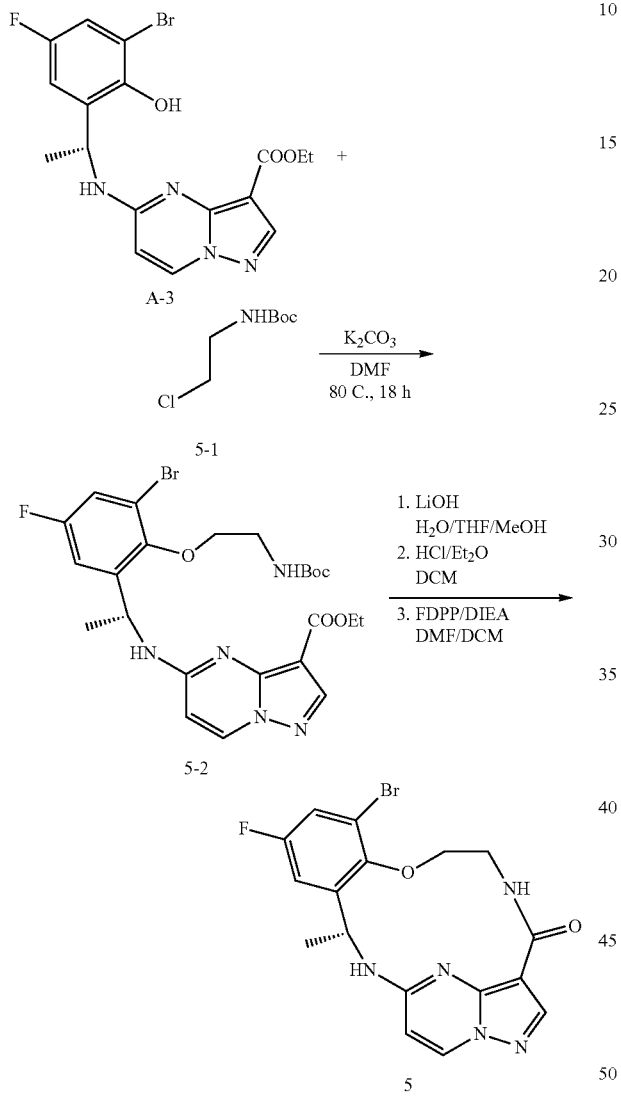

Step 1. To A-3 (200.00 mg, 472.55 µmol) in DMF (2.36 mL) at ambient temperature, $K_2CO_3$ (261.24 mg, 1.89 mmol) was added followed by 5-1 (254.67 mg, 1.42 mmol, 238.01 µL). The mixture was heated to 80° C. and stirred for 18 hours. DCM (5 mL) was added at ambient temperature and the solution was stirred for 10 minutes before being filtered. Flash column chromatography (ISCO, 12 g, 30-80% ethyl acetate in hexanes) provided 5-2 (218.10 mg, 385 µmol, 81% yield).

Step 2. 5-2 was converted to 5 following step 6 in General Method F.

Compound 6 was prepared using General Methods J and F using A-2.

Compound 7 and 8 were prepared using General Methods G and F using A-3 and A-2 respectively.

Compound 9 and 10 were prepared using General Methods J and F using A-5 and A-6 respectively.

Compound 11 was prepared using General Methods G and F using A-4.

Compound 12 was prepared using General Methods J and F starting with A-5 and tert-butyl (3-chloropropyl)carbamate in step 1 of General Method J.

Compound 13 was prepared using General Methods J and F using A-7.

Compound 14 was prepared using General Methods G and F using A-7.

General Method K.

Preparation of (13R)-11-fluoro-13-methyl-9-[(propan-2-yl)oxy]-6,7,13,14-tetrahydro-1,15-ethenopyrazolo[4,3-f][1,4,8,10]benzoxatriazacyclotridecin-4(5H)-one (15)

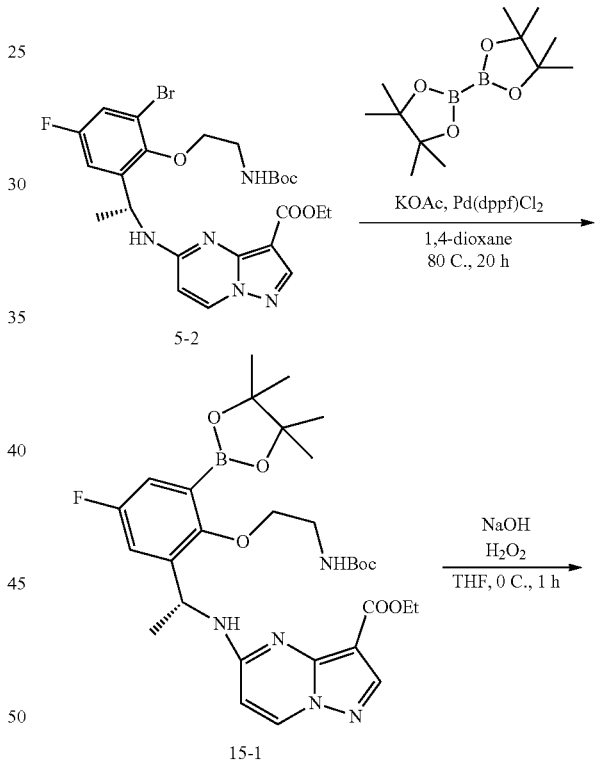

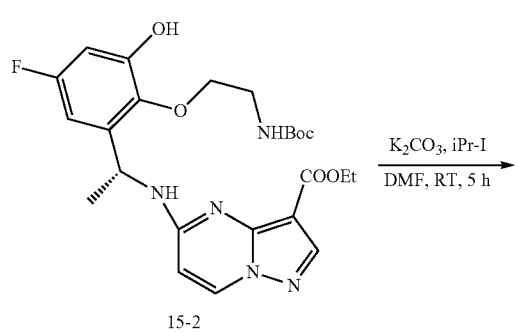

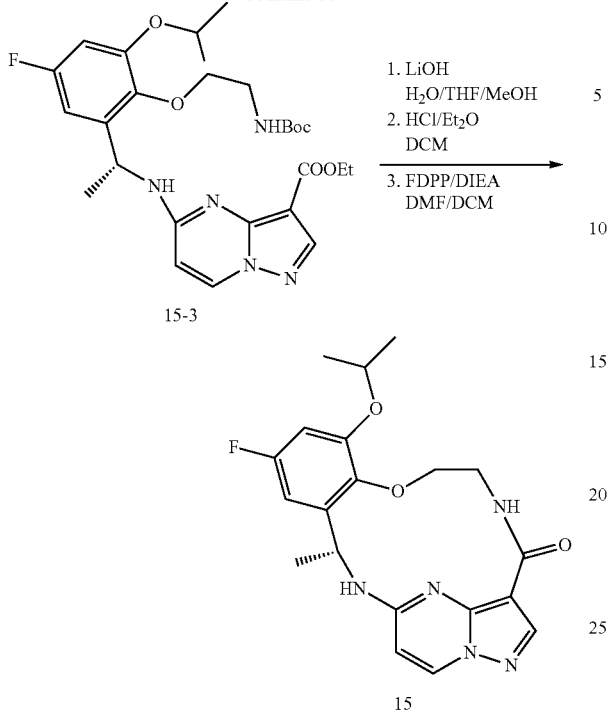

General Method L.

Preparation of (13R)-11-fluoro-9-hydroxy-13-methyl-6,7,13,14-tetrahydro-1,15-ethenopyrazolo[4,3-f][1,4,8,10]benzoxatriazacyclotridecin-4(5H)-one (17)

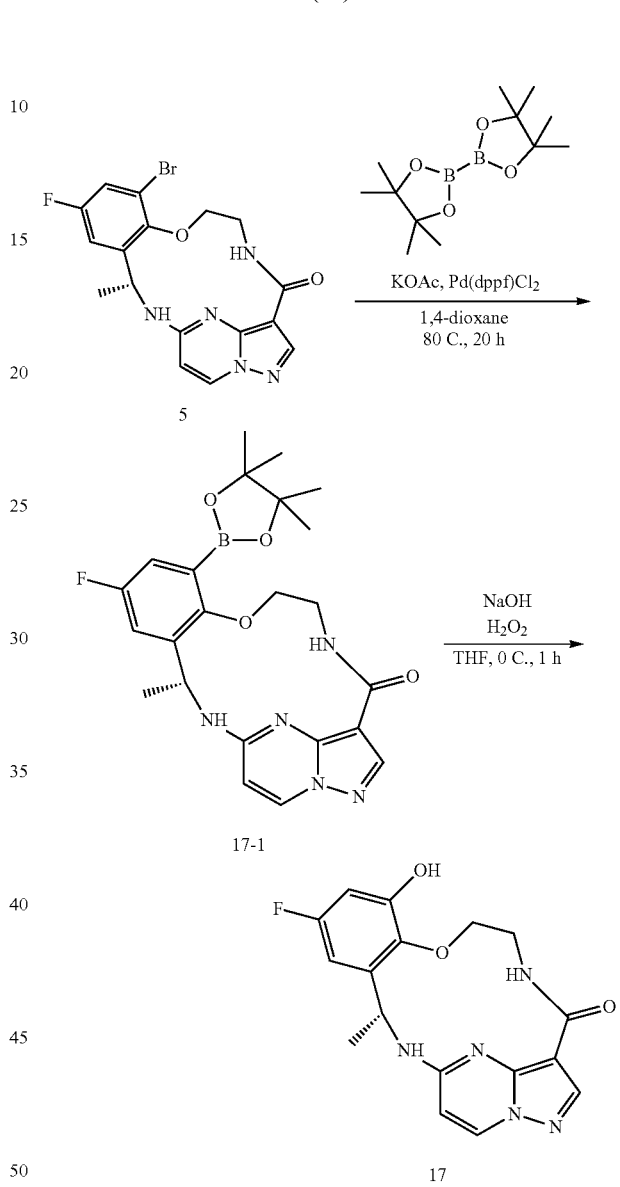

Step 1. To 5-2 (50.00 mg, 88.27 μmol) in dioxane (882.70 μL) was added Bis(pinacol)diboron (44.83 mg, 176.54 μmol) under argon. The mixture was flushed with argon and Pd(dppf)Cl$_2$ (4.41 μmol) was added. The vessel was sealed and heated to 80° C. and stirred for 20 hours. Cooled to ambient temperature, diluted with water (5 mL) and extracted with DCM (3×5 mL). Combined organic phase was washed with brine and dried over Na$_2$SO$_4$. Flash column chromatography (ISCO, 12 g, 20 to 60% ethyl acetate in hexanes) to provide 15-1 (46.80 mg, 76.29 μmol, 86.42% yield).

Step 2. To 15-1 (46.80 mg, 76.29 μmol) in THF (2.00 mL) at 0° C., aqueous NaOH (1 M, 80.00 μL) was added followed by H$_2$O$_2$ (2.59 mg, 76.29 μmol, 80.00 μL, 30%). Stir for 30 minutes and then diluted with ethyl acetate (5 mL) and water (5 mL). Aqueous layer was extracted again with ethyl acetate (2×5 mL). The combined organic phase was washed with brine and dried over Na$_2$SO$_4$. Flash column chromatography (ISCO, 12 g, 30 to 80% ethyl acetate in hexanes) to afford 15-2 (26.80 mg, 53.23 μmol, 69.77% yield).

Step 3. To 15-2 (13.40 mg, 26.61 μmol) in DMF (268.10 μL) was added K$_2$CO$_3$ (11.03 mg, 79.83 μmol) followed by 2-Iodopropane (6.79 mg, 39.92 μmol, 3.99 μL). Stirred at ambient temperature for 5 hours and then quenched with methanol (0.1 mL). Water (2 mL) was added and extracted with DCM (3×2 mL). The combined organic layer was washed with brine and dried over sodium sulfate. Flash column chromatography (ISCO, 12 g, 20-60% ethyl acetate in hexanes) provided 15-3 (9.60 mg, 17.60 μmol, 66.12% yield).

Step 4. 15-3 was converted to 15 using General Method F.

Compound 16 was prepared using General Methods K and F using methyl iodide and 15-2.

Step 1. To 5 (20.00 mg, 47.59 μmol) in 1,4-dioxane (882.70 μL) was added Bis(pinacol)diboron (24.17 mg, 95.18 μmol) under argon. The reaction mixture was flushed with argon and Pd(dppf)Cl$_2$ (2.38 μmol) was added. The vessel was sealed and heated to 80° C. for 18 hours. Cooled to ambient temperature and diluted with water (5 mL). Extracted with DCM (3×5 mL) and the combined organic phase was washed with brine and dried over sodium sulfate. Flash column chromatography (ISCO, 12 g, 20 to 60% ethyl acetate in hexanes) to provide 17-1 contaminated with de-brominated 5.

Step 2. To crude 17-1 (21.96 mg, 47.00 μmol) in tetrahydrofuran (1.50 mL) at 0° C. was added aqueous NaOH (1 M, 47.00 μL) followed by H$_2$O$_2$ (1.60 mg, 47.00 μmol, 30%). The solution was stirred for 1 hour. Diluted with water (5 mL) and extracted with DCM (3×5 mL). Combined organic phase was washed with brine and dried over sodium sulfate. Flash column chromatography (ISCO, 12 g, Methanol in DCM, 0 to 10%) to afford 17 (2.26 mg, 6.32 μmol, 13.46% yield).

General Method M.

Preparation of (7S,13R)-11-fluoro-7,13-dimethyl-9-(1-methyl-1H-pyrazol-4-yl)-6,7,13,14-tetrahydro-1,15-ethenopyrazolo[4,3-f][1,4,8,10]benzoxatriazacyclotridecin-4(5H)-one (18)

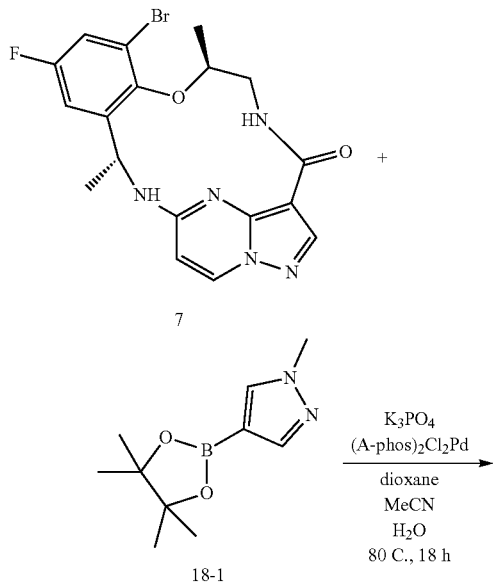

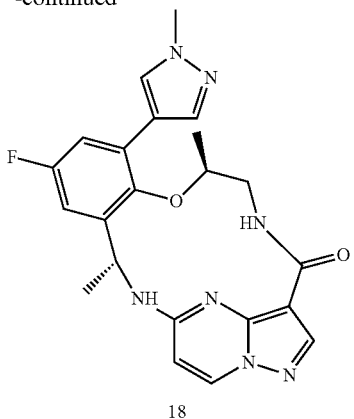

Step 1. To 7 (22.45 mg, 51.70 μmol) and 18-1 (13.98 mg, 67.21 μmol) combined in 1,4-dioxane (214.14 uL) and MeCN (214.14 uL), argon was bubbled through the solution as $K_3PO_4$ (2 M, 51.70 uL) was added. Catalyst, (A-phos)$_2Cl_2$Pd (1.83 mg, 2.59 μmol) was added under argon at room temperature. The reaction vessel was purged with argon, sealed, heated to 80° C. and stirred for 5 hours. Mixture was cooled to ambient temperature and water (5 mL) was added. Extracted with DCM (3×5 mL), the combined organic phase was washed with brine and then dried over $Na_2SO_4$. Flash column chromatography (ISCO, 12 g, 0% to 10% methanol in dcm) provided 18 (14.46 mg, 33.2 μmol, 64% yield).

Compounds 19 and 20 were prepared using General Method M starting with 5 and 7 respectively.

| Compd # | Structure | MS m/z | $^1$H NMR (500 MHz, DMSO-d$_6$) δ ppm |
|---|---|---|---|
| 1 | 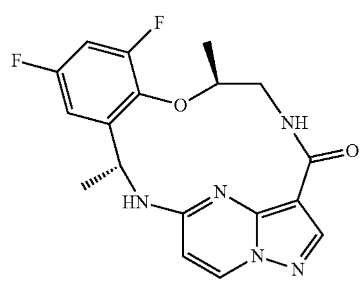 [SMILES: C[C@H]1CNC(=O)c2cnn3ccc(nc23)N[C@H](C)c2cc(F)cc(F)c2O1] | 374.2 | 9.81 (t, J = 5.44 Hz, 1 H), 8.91 (d, J = 5.73 Hz, 1 H), 8.64 (d, J = 7.45 Hz, 1 H), 8.06 (s, 1 H), 7.14 (ddd, J = 13.75, 8.31, 3.15 Hz, 1 H), 6.94-7.01 (m, 1 H), 6.42 (d, J = 8.02 Hz, 1 H), 5.40-5.50 (m, 1 H), 4.79 (tt, J = 6.16, 3.29 Hz, 1 H), 3.67 (ddd, J = 14.32, 5.73, 3.44 Hz, 1 H), 3.28-3.33 (m, 1 H), 1.44-1.54 (m, 3 H), 1.38 (d, J = 6.87 Hz, 3 H) |
| 2 | 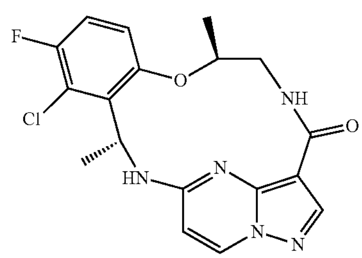 [SMILES: C[C@H]1CNC(=O)c2cnn3ccc(nc23)N[C@H](C)c2c(ccc(F)c2Cl)O1] | 390.2 | 9.63-9.73 (m, 1 H), 8.84 (d, J = 6.87 Hz, 1 H), 8.58 (d, J = 8.02 Hz, 1 H), 8.03 (s, 1 H), 7.18-7.28 (m, 1 H), 7.07-7.16 (m, 1 H), 6.48 (d, J = 7.45 Hz, 1 H), 5.84-5.95 (m, 1 H), 4.69-4.79 (m, 1 H), 3.82 (ddd, J = 13.75, 5.73, 4.58 Hz, 1 H), 3.25 (ddd, J = 13.75, 6.01, 4.30 Hz, 1 H), 1.62 (d, J = 7.45 Hz, 3 H), 1.46 (d, J = 5.73 Hz, 3 H) |

| Compd # | Structure | MS m/z | $^1$H NMR (500 MHz, DMSO-$d_6$) δ ppm |
|---|---|---|---|
| 3 | 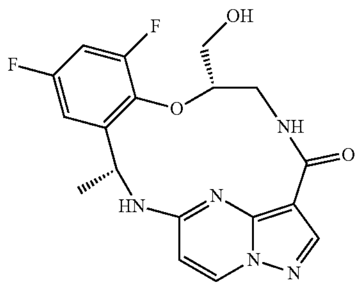 [SMILES: C[C@H]1Nc2ccn3ncc(c3n2)C(=O)NC[C@@H](CO)Oc2c(F)cc(F)cc21] | 390.2 | 1.40 (d, J = 6.87 Hz, 3 H), 3.46 (br d, J = 2.29 Hz, 2 H), 3.63 (br s, 1 H), 3.76-3.86 (m, 1 H), 4.68 (br d, J = 4.58 Hz, 1 H), 4.95 (br s, 1 H), 5.47-5.60 (m, 1 H), 6.43 (d, J = 8.02 Hz, 1 H), 6.98 (br d, J = 8.59 Hz, 1 H), 7.17 (ddd, J = 12.03, 8.59, 3.44 Hz, 1 H), 8.06 (s, 1 H), 8.65 (d, J = 8.02 Hz, 1 H), 8.84 (d, J = 5.73 Hz, 1 H), 9.38 (br t, J = 4.30 Hz, 1 H) |
| 4 | 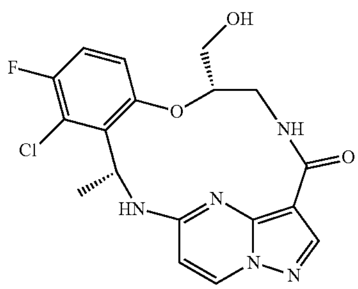 [SMILES: C[C@H]1Nc2ccn3ncc(c3n2)C(=O)NC[C@@H](CO)Oc2ccc(F)c(Cl)c21] | 406.2 | 1.61 (d, J = 7.45 Hz, 3 H), 3.68-3.83 (m, 1 H), 3.93 (s, 1 H), 4.65 (dq, J = 10.31, 5.16 Hz, 1 H), 5.29 (t, J = 5.16 Hz, 1 H), 5.71-5.79 (m, 1 H), 6.48 (d, J = 7.45 Hz, 1 H), 7.15 (t, J = 8.88 Hz, 1 H), 7.39 (dd, J = 9.45, 4.30 Hz, 1 H), 8.02 (s, 1 H), 8.59 (d, J = 7.45 Hz, 1 H), 8.84 (d, J = 5.73 Hz, 1 H), 9.30 (br d, J = 6.87 Hz, 1 H) |
| 5 | 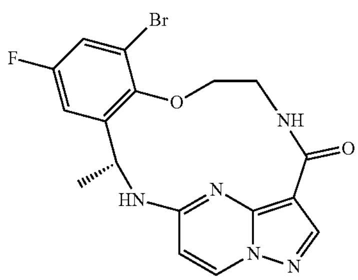 [SMILES: C[C@H]1Nc2ccn3ncc(c3n2)C(=O)NCCOc2c(Br)cc(F)cc21] | 420.2 | 1.36 (d, J = 6.87 Hz, 3 H), 3.47 (ddt, J = 11.81, 8.66, 2.94, 2.94 Hz, 1 H), 3.77 (dddd, J = 14.75, 7.30, 4.87, 2.86 Hz, 1 H), 4.22 (ddd, J = 11.03, 8.45, 2.86 Hz, 1 H), 5.03 (ddd, J = 10.88, 4.87, 2.58 Hz, 1 H), 5.60 (td, J = 6.73, 1.43 Hz, 1 H), 6.43 (d, J = 8.02 Hz, 1 H), 7.19 (dd, J = 8.88, 3.15 Hz, 1 H), 7.42 (dd, J = 7.73, 3.15 Hz, 1 H), 8.07 (s, 1 H), 8.66 (d, J = 7.45 Hz, 1 H), 8.96 (d, J = 6.30 Hz, 1 H), 10.07 (dd, J = 7.45, 2.86 Hz, 1 H) |
| 6 | 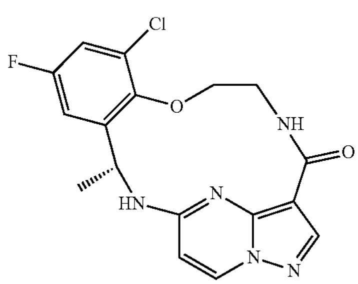 [SMILES: C[C@H]1Nc2ccn3ncc(c3n2)C(=O)NCCOc2c(Cl)cc(F)cc21] | 376.2 | 1.36 (d, J = 6.87 Hz, 3 H), 3.40-3.50 (m, 1 H), 3.77 (dddd, J = 14.75, 7.59, 4.58, 2.86 Hz, 1 H), 4.18 (ddd, J = 11.03, 8.74, 2.58 Hz, 1 H), 4.96-5.04 (m, 1 H), 5.57-5.66 (m, 1 H), 6.43 (d, J = 8.02 Hz, 1 H), 7.16 (dd, J = 9.17, 3.44 Hz, 1 H), 7.26-7.31 (m, 1 H), 8.07 (s, 1 H), 8.66 (d, J = 7.45 Hz, 1 H), 8.95 (d, J = 6.30 Hz, 1 H), 10.06 (dd, J = 7.45, 2.86 Hz, 1 H) |
| 7 | 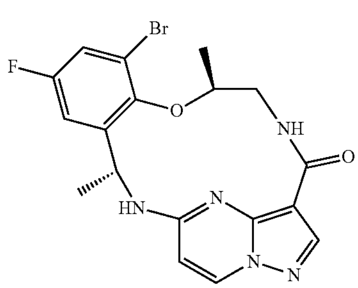 [SMILES: C[C@H]1CNC(=O)c2cnn3ccc(nc23)N[C@H](C)c2cc(F)cc(Br)c2O1] | 434.2 | 1.35 (d, J = 6.87 Hz, 3 H), 1.47 (d, J = 6.30 Hz, 3 H), 3.39 (dd, J = 14.32, 3.44 Hz, 1 H), 3.9 (ddd, J = 14.75, 8.74, 2.29 Hz, 1 H), 5.30-5.39 (m, 1 H), 5.64 (dt, J = 5.73, 2.86 Hz, 1 H), 6.49 (d, J = 8.02 Hz, 1 H), 7.09 (dd, J = 8.88, 3.15 Hz, 1 H), 7.34-7.40 (m, 1 H), 8.05 (s, 1 H), 8.67 (d, J = 8.02 Hz, 1 H), 8.89 (d, J = 4.58 Hz, 1 H), 9.48 (d, J = 8.59 Hz, 1 H) |

| Compd # | Structure | MS m/z | $^1$H NMR (500 MHz, DMSO-$d_6$) δ ppm |
|---|---|---|---|
| 8 | 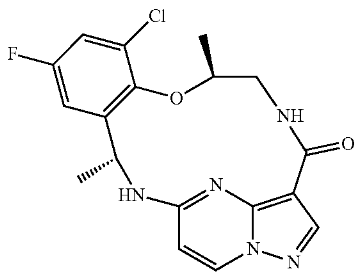 [SMILES: C[C@H]1CNC(=O)c2cnn3ccc(nc23)N[C@H](C)c2cc(F)cc(Cl)c2O1] | 390.2 | 1.35 (d, J = 6.87 Hz, 3 H), 1.47 (d, J = 6.30 Hz, 3 H), 3.36-3.43 (m, 1 H), 3.66 (ddd, J = 14.89, 8.59, 2.29 Hz, 1 H), 5.31-5.41 (m, 1 H), 5.52 (dt, J = 6.59, 3.01 Hz, 1 H), 6.48 (d, J = 7.45 Hz, 1 H), 7.06 (dd, J = 8.88, 3.15 Hz, 1 H), 7.24 (dd, J = 8.02, 3.44 Hz, 1 H), 8.05 (s, 1 H), 8.67 (d, J = 8.02 Hz, 1 H), 8.89 (d, J = 4.58 Hz, 1 H), 9.51 (d, J = 7.45 Hz, 1 H) |
| 9 | 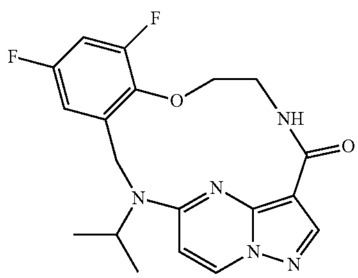 [SMILES: CC(C)N1Cc2cc(F)cc(F)c2OCCNC(=O)c2cnn3ccc1nc23] | 388.2 | 1.21 (d, J = 6.87 Hz, 3 H), 1.49 (d, J = 6.30 Hz, 3 H), 3.41-3.52 (m, 1 H), 3.59-3.70 (m, 1 H), 4.23 (d, J = 16.04 Hz, 1 H), 4.46-4.54 (m, 1 H), 4.55-4.62 (m, 1 H), 4.66 (dt, J = 13.17, 6.59 Hz, 1 H), 5.07-5.15 (m, 1 H), 6.88 (dd, J = 8.59, 2.29 Hz, 1 H), 7.04 (d, J = 8.02 Hz, 1 H), 7.14-7.22 (m, 1 H), 8.11 (s, 1 H), 8.81 (d, J = 8.02 Hz, 1 H), 9.22 (dd, J = 6.30, 4.01 Hz, 1 H) |
| 10 | 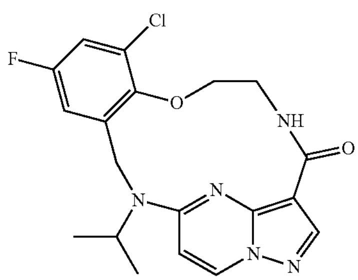 | 404.2 | 1.18 (d, J = 6.30 Hz, 3 H) 1.42 (d, J = 6.30 Hz, 3 H) 3.32-3.39 (m, 1 H) 3.60-3.69 (m, 1 H) 4.26 (d, J = 16.04 Hz, 1 H) 4.55-4.68 (m, 2 H) 4.78 (dt, J = 11.89, 3.51 Hz, 1 H) 5.01-5.08 (m, 1 H) 6.95-7.05 (m, 2 H) 7.25 (dd, J = 7.73, 3.15 Hz, 1 H) 8.06 (s, 1 H) 8.79 (d, J = 8.02 Hz, 1 H) 9.31 (dd, J = 6.59, 3.15 Hz, 1 H) |
| 11 | 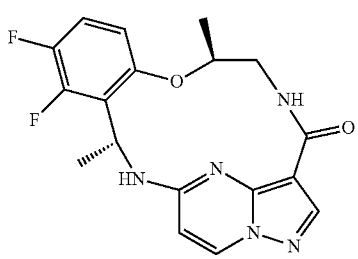 [SMILES: C[C@H]1CNC(=O)c2cnn3ccc(nc23)N[C@H](C)c2c(ccc(F)c2F)O1] | 374.2 | 1.45 (d, J = 6.30 Hz, 3 H), 1.59 (d, J = 7.45 Hz, 3 H), 3.16 (ddd, J = 13.60, 8.45, 2.58 Hz, 1 H), 3.91 (ddd, J = 13.17, 8.02, 4.01 Hz, 1 H), 4.56 (ddd, J = 8.16, 5.87, 4.30 Hz, 1 H), 5.63 (quin, J = 7.02 Hz, 1 H), 6.44 (d, J = 7.45 Hz, 1 H), 6.87 (dd, J = 9.74, 2.29 Hz, 1 H), 7.22 (q, J = 9.36 Hz, 1 H), 8.04 (s, 1 H), 8.58 (d, J = 7.45 Hz, 1 H), 8.84 (d, J = 6.87 Hz, 1 H), 9.80 (dd, J = 7.45, 2.29 Hz, 1 H) |
| 12 | 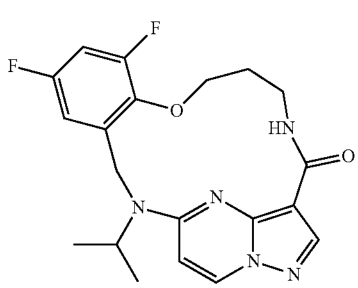 [SMILES: CC(C)N1Cc2cc(F)cc(F)c2OCCCNC(=O)c2cnn3ccc1nc23] | 402.2 | 1.23 (br s, 3 H), 1.46 (br s, 3 H), 1.98-2.03 (m, 2 H), 3.35-3.43 (m, 1 H), 3.62-3.83 (m, 1 H), 4.16-4.29 (m, 1 H), 4.47-4.58 (m, 1 H), 4.63 (dt, J = 13.32, 6.80 Hz, 2 H), 5.16-5.32 (m, 1 H), 6.80-6.87 (m, 1 H), 6.98 (d, J = 8.02 Hz, 1 H), 7.12 (ddd, J = 13.46, 8.59, 3.15 Hz, 1 H), 8.08-8.14 (m, 2 H), 8.75 (d, J = 8.02 Hz, 1 H) |

| Compd # | Structure | MS m/z | $^1$H NMR (500 MHz, DMSO-$d_6$) δ ppm |
|---|---|---|---|
| 13 | 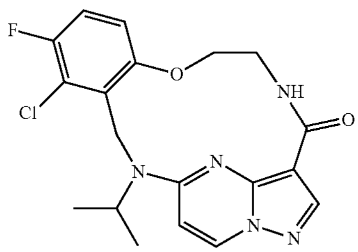 [SMILES: CC(C)N1Cc2c(ccc(F)c2Cl)OCCNC(=O)c2cnn3ccc1nc23] | 404.2 | 1.28 (d, J = 6.87 Hz, 3 H), 1.58 (d, J = 6.30 Hz, 3 H), 3.46-3.54 (m, 1 H), 3.67 (tdd, J = 10.81, 10.81, 5.30, 2.86 Hz, 1 H), 4.30 (d, J = 14.89 Hz, 1 H), 4.51 (td, J = 11.46, 5.73 Hz, 1 H), 4.58 (quin, J = 6.59 Hz, 1 H), 4.67-4.74 (m, 1 H), 5.24 (dd, J = 15.18, 1.43 Hz, 1 H), 6.97 (d, J = 8.02 Hz, 1 H), 7.16-7.23 (m, 2 H), 8.08 (s, 1 H), 8.70-8.76 (m, 2 H) |
| 14 | 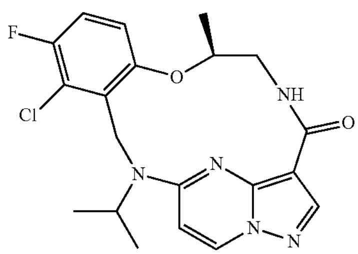 [SMILES: CC(C)N1Cc2c(ccc(F)c2Cl)O[C@@H](C)CNC(=O)c2cnn3ccc1nc23] | 418.3 | 1.29 (d, J = 6.30 Hz, 3 H), 1.46 (d, J = 6.30 Hz, 3 H), 1.58 (d, J = 6.87 Hz, 3 H), 3.28-3.32 (m, 1 H), 3.73-3.83 (m, 1 H), 4.30 (d, J = 14.89 Hz, 1 H), 4.56 (quin, J = 6.73 Hz, 1 H), 4.92-5.00 (m, 1 H), 5.25 (dd, J = 14.89, 1.72 Hz, 1 H), 6.96 (d, J = 8.02 Hz, 1 H), 7.11-7.25 (m, 2 H), 8.08 (s, 1 H), 8.74 (d, J = 8.02 Hz, 1 H), 8.83 (dd, J = 6.30, 3.44 Hz, 1 H) |
| 15 | 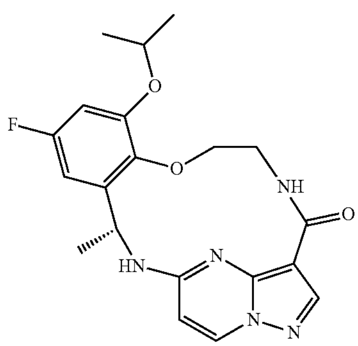 [SMILES: CC(C)Oc1cc(F)cc2c1OCCNC(=O)c1cnn3ccc(nc13)N[C@@H]2C] | 400.2 | 1.29 (dd, J = 7.16, 6.01 Hz, 6 H), 1.34 (d, J = 6.87 Hz, 3 H), 3.34-3.40 (m, 1 H), 3.70 (dddd, J = 14.46, 7.30, 4.58, 2.86 Hz, 1 H), 4.01 (ddd, J = 11.17, 8.88, 2.86 Hz, 1 H), 4.60 (dt, J = 12.03, 6.01 Hz, 1 H), 4.72-4.81 (m, 1 H), 5.57-5.66 (m, 1 H), 6.39 (d, J = 7.45 Hz, 1 H), 6.67 (dd, J = 9.17, 2.86 Hz, 1 H), 6.81 (dd, J = 10.60, 3.15 Hz, 1 H), 8.05 (s, 1 H), 8.59-8.64 (m, 1 H), 8.87 (d, J = 6.87 Hz, 1 H), 10.02 (dd, J = 7.45, 2.86 Hz, 1 H) |
| 16 | 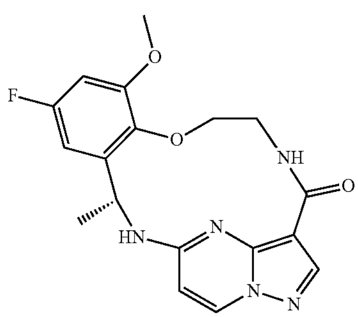 [SMILES: COc1cc(F)cc2c1OCCNC(=O)c1cnn3ccc(nc13)N[C@@H]2C] | 372.2 | 1.35 (d, J = 6.87 Hz, 3 H), 3.37 (br d, J = 2.86 Hz, 1 H), 3.63-3.72 (m, 1 H), 3.79 (s, 3 H), 4.03 (ddd, J = 11.03, 8.45, 2.86 Hz, 1 H), 4.71-4.78 (m, 1 H), 5.56-5.67 (m, 1 H), 6.40 (d, J = 8.02 Hz, 1 H), 6.71 (dd, J = 9.17, 2.86 Hz, 1 H), 6.83 (dd, J = 10.31, 2.86 Hz, 1 H), 8.05 (s, 1 H), 8.62 (d, J = 8.02 Hz, 1 H), 8.87 (d, J = 6.87 Hz, 1 H), 9.99 (dd, J = 7.16, 3.15 Hz, 1 H) |
| 17 | 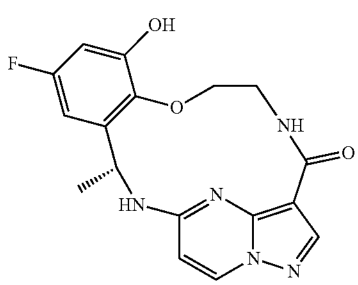 [SMILES: C[C@H]1Nc2ccn3ncc(c3n2)C(=O)NCCOc2c(O)cc(F)cc21] | 358.1 | 1.34 (d, J = 6.87 Hz, 3 H), 3.34-3.41 (m, 1 H), 3.63-3.76 (m, 1 H), 4.08-4.17 (m, 1 H), 4.70-4.80 (m, 1 H), 5.56-5.66 (m, 1 H), 6.39 (d, J = 7.45 Hz, 1 H), 6.50 (dd, J = 9.74, 3.44 Hz, 1 H), 6.56 (dd, J = 9.16, 3.44 Hz, 1 H), 8.05 (s, 1 H), 8.61 (d, J = 7.45 Hz, 1 H), 8.83 (d, J = 6.87 Hz, 1 H), 9.99 (dd, J = 7.45, 3.44 Hz, 1 H), 10.04 (s, 1 H) |

-continued

| Compd # | Structure | MS m/z | $^1$H NMR (500 MHz, DMSO-$d_6$) δ ppm |
|---|---|---|---|
| 18 | 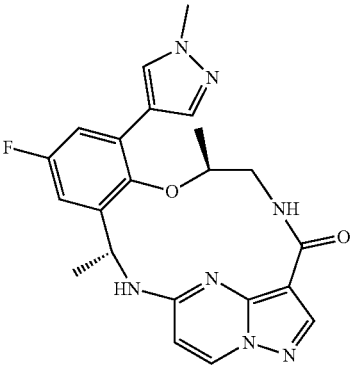 [SMILES: C[C@H]1CNC(=O)c2cnn3ccc(nc23)N[C@H](C)c2cc(F)cc(-c3cnn(C)c3)c2O1] | 436.2 | 1.31 (d, J = 6.30 Hz, 3 H), 1.41 (d, J = 6.87 Hz, 3 H), 2.92 (dd, J = 14.32, 3.44 Hz, 1 H), 3.23-3.29 (m, 1 H), 3.90 (s, 3 H), 4.60 (dt, J = 6.30, 1.72 Hz, 1 H), 5.38-5.43 (m, 1 H), 6.50 (d, J = 8.02 Hz, 1 H), 6.86-6.89 (m, 1 H), 6.93 (dd, J = 9.16, 3.44 Hz, 1 H), 7.65 (s, 1 H), 8.00 (d, J = 6.30 Hz, 2 H), 8.65-8.67 (m, 1 H), 8.84 (d, J = 4.58 Hz, 1 H), 9.37 (d, J = 9.17 Hz, 1 H) |
| 19 | 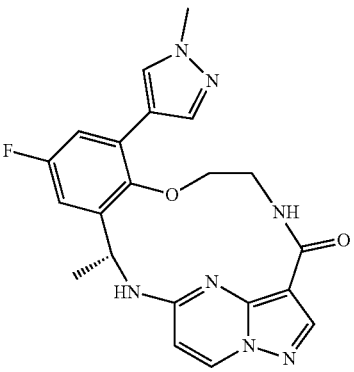 [SMILES: C[C@H]1Nc2ccn3ncc(c3n2)C(=O)NCCOc2c(-c3cnn(C)c3)cc(F)cc21] | 422.2 | 1.42 (d, J = 6.87 Hz, 3 H), 3.15-3.25 (m, 1 H), 3.36-3.44 (m, 1 H), 3.47-3.57 (m, 1 H), 3.88 (s, 3 H), 4.19-4.27 (m, 1 H), 5.63-5.71 (m, 1 H), 6.44 (d, J = 7.45 Hz, 1 H), 6.93 (dd, J = 8.59, 3.44 Hz, 1 H), 7.06 (dd, J = 9.17, 3.44 Hz, 1 H), 7.59 (s, 1 H), 7.92 (s, 1 H), 8.04 (s, 1 H), 8.64 (d, J = 8.02 Hz, 1 H), 8.94 (d, J = 6.87 Hz, 1 H), 10.08 (dd, J = 8.02, 2.29 Hz, 1 H) |
| 20 | 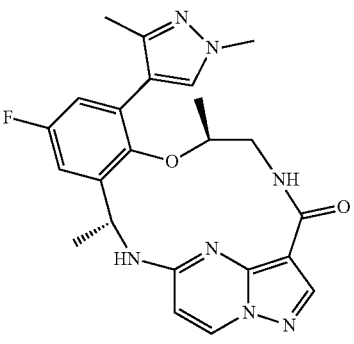 | 450.2 | 1.28 (d, J = 6.30 Hz, 3 H), 1.40 (d, J = 6.87 Hz, 3 H), 2.04 (s, 3 H), 2.92 (dd, J = 14.03, 3.72 Hz, 1 H), 3.21-3.28 (m, 1 H), 3.82 (s, 3 H), 4.17-4.29 (m, 1 H), 5.36-5.49 (m, 1 H), 6.50 (d, J = 7.45 Hz, 1 H), 6.74 (dd, J = 8.88, 3.15 Hz, 1 H), 6.93-6.99 (m, 1 H), 7.86 (s, 1 H), 8.02 (s, 1 H), 8.66 (d, J = 8.02 Hz, 1 H), 8.86 (d, J = 4.58 Hz, 1 H), 9.40 (d, J = 9.17 Hz, 1 H) |

Biologic Assays

The Compounds were tested against BTK kinase using the Eurofins standard KinaseProfiler™ assays and following the relevant standard operating procedures. Protein kinases were assayed in a radiometric format. Full details of the assay for each kinase are available on the Eurofins website, or in the accompanying protocol document. All compounds were prepared to a working stock of 50× final assay concentration in 100% DMSO. Where appropriate, more concentrated stocks were diluted manually to 50× using 100% DMSO. Compounds supplied as powders were reconstituted to a 10 mM stock in 100% DMSO before further dilution to 50×. The required volume of the 50× stock of test compound was added to the assay well, before a reaction mix containing the enzyme and substrate was added. The reaction was initiated by the addition of ATP at the selected 10 μM concentration. There was no pre-incubation of the compound with the enzyme/substrate mix prior to ATP addition.

For IC50 determinations, data are analysed using XLFit version 5.3 (ID Business Solutions). Sigmoidal dose-response (variable slope) curves are fit based on the mean result for each test concentration using non-linear regression analysis. Where the top and/or bottom of the curve fall >10% out with 100 and 0, respectively, either or both of these limits may be constrained at 100 and 0, provided that the QC criterion on $R^2$ is met.

The BTK biochemical kinase assay was also performed at Reaction Biology Corporation (www.reactionbiology.com, Malvern, Pa.) following the procedures described in the reference (Anastassiadis T, et al *Nat Biotechnol.* 2011, 29, 1039). Specific kinase/substrate pairs along with required cofactors were prepared in reaction buffer; 20 mM Hepes pH 7.5, 10 mM MgCl2, 1 mM EGTA, 0.02% Brij35, 0.02 mg/ml BSA, 0.1 mM Na3VO4, 2 mM DTT, 1% DMSO (for specific details of individual kinase reaction components see Supplementary Table 2). Compounds were delivered into the reaction, followed ~20 minutes later by addition of a mixture of ATP (Sigma, St. Louis Mo.) and $^{33}$P ATP (Perkin Elmer, Waltham Mass.) to a final concentration of 10 μM. Reactions were carried out at room temperature for 120 min, followed by spotting of the reactions onto P81 ion exchange filter paper (Whatman Inc., Piscataway, N.J.). Unbound phosphate was removed by extensive washing of filters in 0.75% phosphoric acid. After subtraction of background derived from control reactions containing inactive enzyme, kinase activity data was expressed as the percent remaining kinase activity in test samples compared to vehicle (dimethyl sulfoxide) reactions. IC$_{50}$ values and curve fits were obtained using Prism (GraphPad Software).

Cell Proliferation Assays.

Colorectal cell lines KM 12 (harboring endogenous TPM3-TRKA fusion gene) cells were cultured in DMEM medium, supplemented with 10% fetal bovine serum and 100 U/mL of penicillin/streptomycin. 5000 cells were seeded in 384 well white plate for 24 hours before compounds treatment. Cell proliferation was measured using CellTiter-Glo luciferase-based ATP detection assay (Promega) following the manufactures's protocol after 72 hours incubation. IC$_{50}$ determinations were performed using GraphPad Prism software (GraphPad, Inc., San Diego, Calif.).

Alternatively: Colorectal cell line KM12 (harboring endogenous TPM3-TRKA fusion gene) cells were cultured in DMEM medium, supplemented with 10% fetal bovine serum and 100 U/mL of penicillin/streptomycin. Essential thrombocythemia cell line SET-2 cells (harboring endogenous JAK2 V618F point mutation) were cultured in RPMI medium, supplemented with 10% fetal bovine serum and 100 U/mL of penicillin/streptomycin. 5000 cells were seeded in 384 well white plate for 24 hours before compounds treatment. Cell proliferation was measured using CellTiter-Glo luciferase-based ATP detection assay (Promega) following the manufactures's protocol after 72 hours incubation. IC$_{50}$ determinations were performed using GraphPad Prism software (GraphPad, Inc., San Diego, Calif.).

Data for compounds tested in BTK biochemical assays and cell proliferation assays are presented in Table 1.

TABLE 1

| Compound | Cell Proliferation | | BTK IC$_{50}$ (nM) |
|---|---|---|---|
| | TRKA KM12 Cell IC$_{50}$ (nM) | JAK2 SET2 Cell IC$_{50}$ (nM) | |
| 1 | 0.2 | 119.6 | 2.47 |
| 2 | 5.1 | 3000 | 2.53 |
| 3 | 21.5 | 15.5 | |
| 4 | 45.4 | 3000 | |
| 5 | 5.0 | 200 | 60 |
| 6 | 4.2 | 78.2 | 64.4 |
| 7 | 0.2 | 6.7 | |
| 8 | 0.2 | 83.7 | 3.97 |
| 9 | 5.2 | 132.2 | 22.25 |
| 10 | 0.1 | 1479 | 179 |
| 11 | 0.2 | 3.9 | 14.25 |
| 12 | 0.2 | 5000 | 9.67 |
| 13 | 300 | 10000 | 5.54 |
| 14 | 0.2 | 1500 | 0.536 |
| 15 | 2 | 500 | 154 |
| 16 | 13.9 | 300 | 450 |
| 17 | 15.4 | 600 | 48 |
| 18 | 23.5 | 600 | 60 |
| 19 | 53.4 | 1000 | 476 |
| 20 | 6.4 | | 238 |

What is claimed is:

1. A method of treating cancer, pain, neurological diseases, autoimmune diseases, or inflammation comprising administering to a subject in need of such treatment an effective amount of at least one compound of the formula Ic

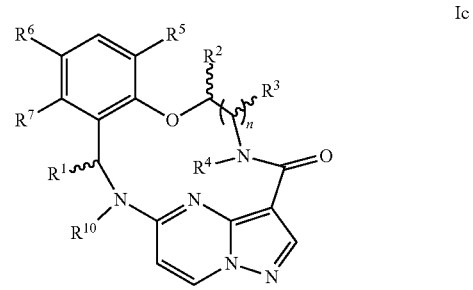

or a pharmaceutically acceptable salt thereof,
wherein
R$^1$ is H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^8$ or —C(O)NR$^8$R$^9$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl;

each R$^2$ and R$^3$ is independently H, deuterium, C$_1$-C$_6$ alkyl, C$_2$-C$_6$ alkenyl, C$_2$-C$_6$ alkynyl, C$_3$-C$_6$ cycloalkyl, C$_6$-C$_{10}$ aryl, —C(O)OR$^8$ or —C(O)NR$^8$R$^9$; wherein each hydrogen atom in C$_1$-C$_6$ alkyl, C$_2$-C$_6$ alkenyl, C$_2$-C$_6$ alkynyl, C$_3$-C$_6$ cycloalkyl and C$_6$-C$_{10}$ aryl is independently optionally substituted by deuterium, halogen, —OH, —CN, —OC$_1$-C$_6$ alkyl, —NH$_2$, —NH(C$_1$-C$_6$ alkyl), —N(C$_1$-C$_6$ alkyl)$_2$, —NHC(O)C$_1$-C$_6$ alkyl, —N(C$_1$-C$_6$ alkyl)C(O)C$_1$-C$_6$ alkyl, —NHC(O)NH$_2$, —NHC(O)NHC$_1$-C$_6$ alkyl, —N(C$_1$-C$_6$ alkyl)C(O)NH$_2$, —N(C$_1$-C$_6$ alkyl)C(O)NHC$_1$-C$_6$ alkyl, —NHC(O)N(C$_1$-C$_6$ alkyl)$_2$, —N(C$_1$-C$_6$ alkyl)C(O)N(C$_1$-C$_6$ alkyl)$_2$, —NHC(O)OC$_1$-C$_6$ alkyl, —N(C$_1$-C$_6$ alkyl)C(O)OC$_1$-C$_6$ alkyl, —NHS(O)(C$_1$-C$_6$ alkyl), —NHS(O)$_2$(C$_1$-C$_6$ alkyl), —N(C$_1$-C$_6$ alkyl)S(O)(C$_1$-C$_6$ alkyl), —N(C$_1$-C$_6$ alkyl)S(O)$_2$(C$_1$-C$_6$ alkyl), —NHS(O)NH$_2$, —NHS(O)$_2$NH$_2$, —N(C$_1$-C$_6$ alkyl)S(O)NH$_2$, —N(C$_1$-C$_6$ alkyl)S(O)$_2$NH$_2$, —NHS(O)NH(C$_1$-C$_6$ alkyl), —NHS(O)$_2$NH(C$_1$-C$_6$ alkyl), —NHS(O)N(C$_1$-C$_6$ alkyl)$_2$, —NHS(O)$_2$N(C$_1$-C$_6$ alkyl)$_2$, —N(C$_1$-C$_6$ alkyl)S(O)NH(C$_1$-C$_6$ alkyl), —N(C$_1$-C$_6$ alkyl)S(O)$_2$NH(C$_1$-C$_6$ alkyl), —N(C$_1$-C$_6$ alkyl)S(O)N(C$_1$-C$_6$ alkyl)$_2$, —N(C$_1$-C$_6$ alkyl)S(O)$_2$N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, —SC$_1$-C$_6$ alkyl, —S(O)C$_1$-C$_6$ alkyl, —S(O)$_2$C$_1$-C$_6$ alkyl, —S(O)NH(C$_1$-C$_6$ alkyl), —S(O)$_2$NH(C$_1$-C$_6$ alkyl), —S(O)N(C$_1$-C$_6$ alkyl)$_2$, —S(O)$_2$N(C$_1$-C$_6$ alkyl)$_2$, —P(C$_1$-C$_6$ alkyl)$_2$, —P(O)(C$_1$-C$_6$ alkyl)$_2$, C$_3$-C$_6$ cycloalkyl, or 3- to 7-membered heterocycloalkyl; or R$^2$ and R$^3$ taken together with the carbon atoms to which they are attached optionally form a C$_5$-C$_7$ cycloalkyl or a 5- to 7-membered heterocycloalkyl;

R$^4$ is H, C$_1$-C$_6$ alkyl or 3- to 7-membered heterocycloalkyl, wherein each hydrogen atom in C$_1$-C$_6$ alkyl or 3- to 7-membered heterocycloalkyl is independently optionally substituted by halogen, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, —C(O)OC$_1$-C$_6$ alkyl, —C(O)NH$_2$, —C(O)NH(C$_1$-C$_6$ alkyl), —C(O)N(C$_1$-C$_6$ alkyl)$_2$, C$_3$-C$_6$ cycloalkyl, or monocyclic 5- to 7-membered heterocycloalkyl;

R$^5$ is selected from the group consisting of fluoro, chloro, bromo, C$_1$-C$_6$ alkyl, —OH, —CN, —OC$_1$-C$_6$ alkyl, —NHC$_1$-C$_6$ alkyl, —N(C$_1$-C$_6$ alkyl)$_2$, C$_3$-C$_6$ cycloalkyl, 3- to 7-membered heterocycloalkyl, —O—(C$_3$-C$_6$ cycloalkyl), —O-(3- to 7-membered heterocycloalkyl), 5- to 7-membered heteroaryl, C$_6$-C$_{10}$ aryl, and CF$_3$; wherein each hydrogen atom in C$_1$-C$_6$ alkyl, —OC$_1$-C$_6$ alkyl, —NHC$_1$-C$_6$ alkyl, —N(C$_1$-C$_6$ alkyl)$_2$, C$_3$-C$_6$ cycloalkyl, 3- to 7-membered -heterocycloalkyl, —O—(C$_3$-C$_6$ cycloalkyl), —O-(3- to 7-membered heterocycloalkyl), 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, NH(C$_1$-C$_6$ alkyl), —N(C$_1$-C$_6$ alkyl)$_2$, C$_3$-C$_7$ cycloalkyl, 3- to 7-membered heterocycloalkyl, C$_6$-C$_{10}$ aryl, 5- to 7-membered heteroaryl, —CO$_2$H, —C(O)OC$_1$-C$_6$ alkyl, —C(O)NH$_2$, —C(O)NH(C$_1$-C$_6$ alkyl) and —C(O)N(C$_1$-C$_6$ alkyl)$_2$;

R$^6$ is selected from the group consisting of H, fluoro, chloro, bromo, C$_1$-C$_6$ alkyl —OH, —CN, —OC$_1$-C$_6$ alkyl, —NHC$_1$-C$_6$ alkyl, —N(C$_1$-C$_6$ alkyl)$_2$, 5- to 7-membered heteroaryl, C$_6$-C$_{10}$ aryl, and -CF$_3$; wherein each hydrogen atom in C$_1$-C$_6$ alkyl, 5- to 7-membered heteroaryl and C$_6$-C$_{10}$ aryl is independently optionally substituted by fluoro, chloro, bromo, —OH, —CN, —OC$_1$-C$_6$ alkyl, —NH$_2$, —NH(C$_1$-C$_6$ alkyl), —N(C$_1$-C$_6$ alkyl)$_2$, —CO$_2$H, C(O)OC$_1$-C$_6$ alkyl, —C(O)NH$_2$, —C(O)NH(C$_1$-C$_6$ alkyl) and —C(O)N(C$_1$-C$_6$ alkyl)$_2$;

R$^7$ is H;

each R$^8$ and R$^9$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl C$_6$-C$_{10}$ aryl or heteroaryl;

R$^{10}$ is independently H, deuterium, C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl: wherein each hydrogen atom in C$_1$-C$_6$ alkyl, C$_2$-C$_6$ alkenyl, C$_2$-C$_6$ alkynyl, C$_3$-C$_6$ cycloalkyl, 3- to 7-membered heterocycloalkyl, C$_6$-C$_{10}$ aryl, or mono- or bicyclic heteroaryl is independently optionally substituted by deuterium, halogen, C$_1$-C$_6$ alkyl, C$_1$-C$_6$ haloalkyl or —OR$^8$; and n is 1 or 2;

and wherein the disease is mediated by Bruton's tyrosine kinase (BTK).

2. The method of claim 1, wherein R$^6$ is fluoro.

3. The method of claim 2, wherein R$^5$ is fluoro, chloro, bromo, —OH, methoxy, ethoxy, iso-propoxy, or n-propoxy.

4. The method of claim 1, wherein R$^3$ is H.

5. The method of claim 1, wherein R$^4$ is H.

6. The method of claim 1, wherein R$^1$ and R$^2$ are each independently H or C$_1$-C$_6$ alkyl, wherein each hydrogen atom in C$_1$-C$_6$ alkyl is independently optionally substituted with deuterium, halogen, or —OH.

7. The method of claim 1, wherein R$^{10}$ is H.

8. The method of claim 2, wherein R$^5$ is selected from the group consisting of fluoro, chloro, bromo, —OH, —CN, —CF$_3$, C$_1$-C$_6$ alkyl, —OC$_1$-C$_6$ alkyl, and 5- to 7-membered heteroaryl.

9. The method of claim 8, wherein R$^3$ is H.

10. The method of claim 9, wherein R$^4$ is H.

11. The method of claim 10, wherein R$^1$ and R$^2$ are each independently H or C$_1$-C$_6$ alkyl, wherein each hydrogen atom in C$_1$-C$_6$ alkyl is independently optionally substituted with deuterium, halogen, or —OH.

12. The method of claim 11, wherein R$^{10}$ is H.

13. A method of treating cancer, pain, neurological diseases, autoimmune diseases, or inflammation comprising administering to a subject in need of such treatment an effective amount of at least one compound selected from the group consisting of

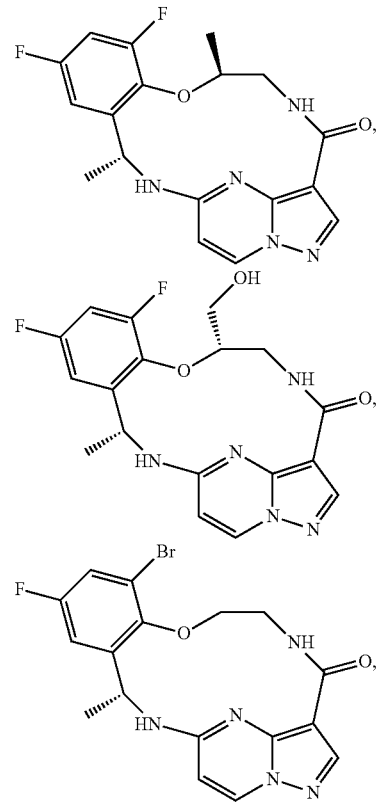

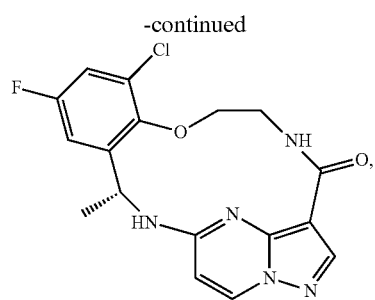
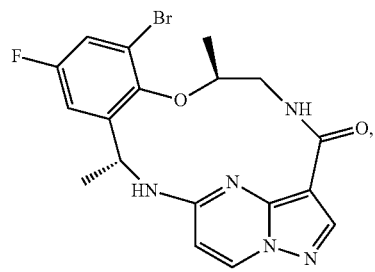
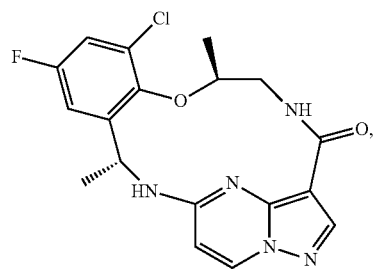
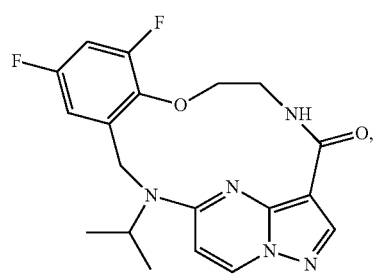
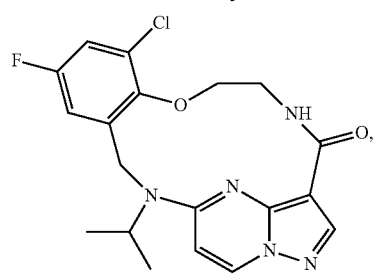
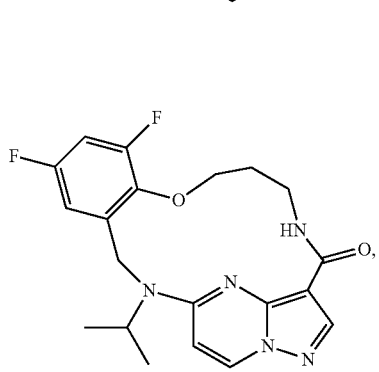
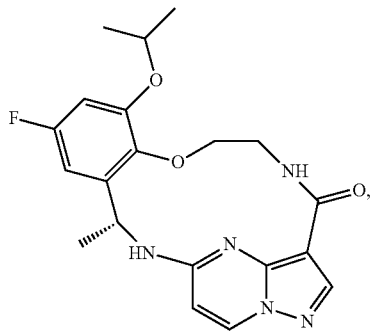
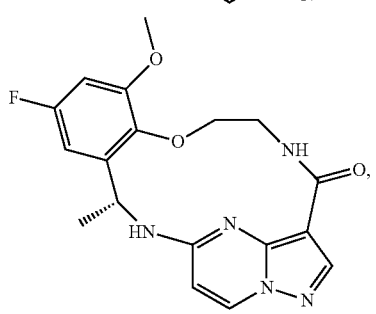
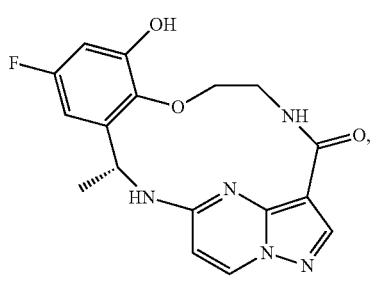
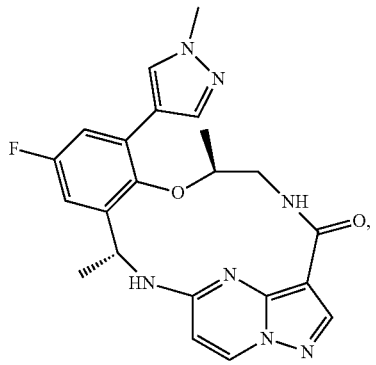
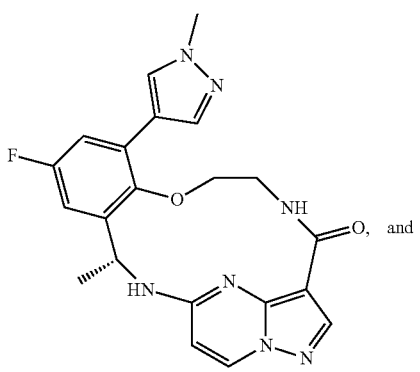

-continued

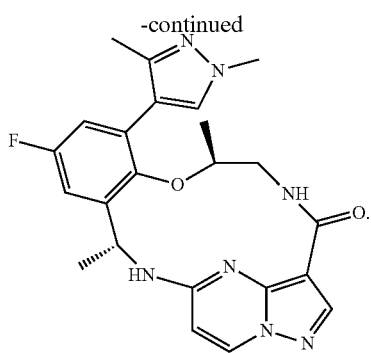

14. The method of claim 1, wherein the disease is cancer.

15. The method of claim 14, wherein the cancer is mediated by a genetically altered BTK.

16. The method of claim 15, wherein the genetically altered BTK comprises at least one resistance mutation.

17. The method of claim 16, wherein the at least one resistance mutation is C481S.

18. The method of claim 14, wherein the cancer is selected from the group consisting of NSCLC, triple negative breast cancer, leukemia, myeloproliferative neoplasms, chronic lymphocytic leukemia, mantle cell leukemia and pancreas adenocarcinoma lung cancer, colon cancer, breast cancer, prostate cancer, hepatocellular carcinoma, renal cell carcinoma, gastric and esophago-gastric cancers, glioblastoma, head and neck cancers, inflammatory myofibroblastic tumors, and anaplastic large cell lymphoma.

19. The method of claim 18, wherein the cancer is NSCLC.

* * * * *